United States Patent
Agnew et al.

(10) Patent No.: US 12,071,487 B2
(45) Date of Patent: Aug. 27, 2024

(54) SITE-SPECIFIC CROSSLINKING OF ANTIBODIES

(71) Applicant: Life Technologies Corporation, Carlsbad, CA (US)

(72) Inventors: Brian Agnew, Eugene, OR (US); Robert Aggeler, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 903 days.

(21) Appl. No.: 16/306,610

(22) PCT Filed: Jun. 16, 2017

(86) PCT No.: PCT/US2017/037871
§ 371 (c)(1),
(2) Date: Dec. 3, 2018

(87) PCT Pub. No.: WO2017/218891
PCT Pub. Date: Dec. 21, 2017

(65) Prior Publication Data
US 2019/0177438 A1 Jun. 13, 2019

Related U.S. Application Data

(60) Provisional application No. 62/351,350, filed on Jun. 17, 2016.

(51) Int. Cl.
*G01N 33/68* (2006.01)
*A61K 9/00* (2006.01)
(Continued)

(52) U.S. Cl.
CPC .......... *C07K 16/468* (2013.01); *A61K 9/0021* (2013.01); *A61K 47/60* (2017.08);
(Continued)

(58) Field of Classification Search
None
See application file for complete search history.

(56) References Cited

U.S. PATENT DOCUMENTS

| 8,236,949 B2 | 8/2012 | Fox et al. |
| 2007/0190597 A1 | 8/2007 | Agnew et al. |

(Continued)

FOREIGN PATENT DOCUMENTS

| WO | 2014065661 | * 5/2014 |
| WO | WO-2014066733 A2 | 5/2014 |

(Continued)

OTHER PUBLICATIONS

Luo et al., PNAS, val. 112, No. 41, Sep. 28, 2015 (Sep. 28, 2015), pp. 12806-12811 (Year: 2015).*

(Continued)

*Primary Examiner* — Karl J Puttlitz

(57) ABSTRACT

Methods are provided for making bispecific antibodies and antibody conjugates comprising site-specifically cross-linking two or more antibodies, antibody fragments or Fc-fusion proteins. Also provided are compositions and uses for the bispecific antibodies and antibody conjugates. The bispecific antibodies may be used to treat a disease or condition. Also provided are methods for site-specifically conjugating a liposome, an mRNA or an siRNA to an antibody, and uses of the antibody-conjugated liposome, mRNA or siRNA.

10 Claims, 24 Drawing Sheets

(51) Int. Cl.
*A61K 47/60* (2017.01)
*A61K 47/68* (2017.01)
*A61K 47/69* (2017.01)
*C07K 16/46* (2006.01)
*C12N 9/24* (2006.01)
*C12N 15/113* (2010.01)
*C12P 21/00* (2006.01)

(52) U.S. Cl.
CPC ...... *A61K 47/6879* (2017.08); *A61K 47/6881* (2017.08); *A61K 47/6913* (2017.08); *C12N 9/2402* (2013.01); *C12N 15/113* (2013.01); *C12P 21/005* (2013.01); *C12Y 302/01018* (2013.01); *C12Y 302/01023* (2013.01); *C12Y 302/01096* (2013.01); *G01N 33/6854* (2013.01); *C07K 2317/10* (2013.01); *C07K 2317/31* (2013.01); *C07K 2317/41* (2013.01); *C07K 2317/52* (2013.01); *C07K 2317/54* (2013.01); *C07K 2317/622* (2013.01); *C07K 2319/30* (2013.01); *C12N 2310/14* (2013.01); *C12N 2310/3513* (2013.01)

(56) References Cited

U.S. PATENT DOCUMENTS

2015/0307620 A1* 10/2015 Vella ............... C07K 16/2878
424/178.1
2017/0356014 A1 12/2017 Kwon et al.

FOREIGN PATENT DOCUMENTS

| WO | WO-2014153002 A1 | 9/2014 |
| WO | 2015175357 | * 11/2015 |
| WO | WO-2015175357 A1 | 11/2015 |

OTHER PUBLICATIONS

Wagner et al., PNAS, val. 111, No. 47, Nov. 10, 2014 (Nov. 10, 2014), pp. 16820-16825 (Year: 2014).*
Huang et al., J. Am. Chem. Soc. 2012, 134, 12308-12318 (Year: 2012).*
Zeglis et al., Bioconjug Chem. Jun. 19, 2013; 24(6): 1057-1067 (Year: 2013).*
H Luo et al: "Noninvasive brain cancer imaging with a bispecific antibody fragment, generated via click chemistry", PNAS, val. 112, No. 41, Sep. 28, 2015 (Sep. 28, 2015), pp. 12806-12811, XP55297009.
Hu Qi-Ying et al: "Towards the next generation of biomedicines by site-selective conjugation", Chemical Society Reviews, val. 45, No. 6, 2016, pp. 1691-1719.
International Preliminary Report on Patentability for International Application No. PCT/US2017/37871 mailed Dec. 18, 2018, 11 pages.
International Search Report and Written Opinion for Application No. PCT/US2017/37871, mailed Oct. 27, 2017, 17 pages.
K Wagner et al: "Bispecific antibody generated with sortase and click chemistry has broad antiinfluenza virus activity", PNAS, val. 111, No. 47, Nov. 10, 2014 (Nov. 10, 2014), pp. 16820-16825, XP5520541.
P K Qasba: "Glycans of Antibodies as a Specific Site for Drug Conjugation Using Glycosyltransferases", Bioconjugate Chemistry, val. 26, No. 11, Nov. 18, 2015 (Nov. 18, 2015), pp. 2170-2175, XP055398267.
Zeglis B.M, et al., "Enzyme-Mediated Methodology for the Site-Specific Radiolabeling of Antibodies Based on Catalyst-Free Click Chemistry", Bioconjugate Chemistry, vol. 24, No. 6, Jun. 19, 2013 (Jun. 19, 2013), pp. 1057-1067.
Agnew et al., "SiteClick site-specific antibody labeling: A universal approach for the robust and reproducible production of ADCs, radioimmuno-PET imaging probes, and bispecific antibodies," World ADC, San Diego, CA, Oct. 10-13, 2016.
Agnew et al., "Establishment of a highly efficient, site-specific and directional antibody crosslinking method for the rapid production and screening of bispecific antibodies," PEGS: The Essential Protein Engineering Summit, Boston, MA, May 1-5, 2017.
Agnew et al., "A novel highly-efficient, site-specific, and directional antibody crosslinking method for the rapid production of bispecific antibodies and the attachment of "armed" protein scaffolds for ADC production," Antibody Engineering and Therapeutics, San Diego, CA, Dec. 12-15, 2017.
Agnew et al., "Streamlined bispecific antibody production using automated chemoenzymatic site-specific crosslinking," PEGS: The Essential Protein Engineering Summit, Boston, MA, April 30-May 3, 2018.
Agnew et al., "Site-specific glycan-conjugated NISTmAb antibody drug conjugate mimetics: synthesis, characterization, and utility," *Anal. Bioanal. Chem.* 413:4989-5001, 2021.
Spasevska, An outlook on biospecific antibodies: Methods of production and therapeutic benefits, *Biosciences Master Reviews*, Jan. 2014.

* cited by examiner

EndoS Cleaved

EndoS Cleaved

Non-cleaved, using existing terminal GlcNAc residues

SITE-SPECIFIC CROSSLINKING OF ANTIBODIES

CROSS-REFERENCE

This application is a National Stage 371 of PCT/US2017/37871, filed Jun. 16, 2017, which claims the benefit under 35 U.S.C. § 119(e) of U.S. Provisional Application No. 62/351,350, filed Jun. 17, 2016. The entire contents of the aforementioned application(s) are incorporated by reference herein.

FIELD OF THE INVENTION

The present invention relates to the field of site-specific crosslinking of antibodies, antibody fragments and/or Fc-fusion proteins to create bispecific antibodies or antibody conjugates.

BRIEF SUMMARY OF THE INVENTION

Provided herein are methods, compositions and kits for use in the directional, site-specific crosslinking of antibodies, antibody fragments comprising terminal GlcNAc residues, and/or Fc-fusion proteins to create bispecific antibodies and antibody conjugates. Also provided herein are methods, compositions and kits for use in the site-specific and directional conjugation of antibodies, antibody fragments comprising terminal GlcNAc residues, and/or Fc-fusion proteins to modified liposomes, modified mRNA or modified siRNA. The methods, compositions and kits provided herein do not require genetic engineering of the antibodies and allow for the directed site-specific crosslinking of antibodies, antibody fragments thereof, and/or Fc-fusion proteins providing full antigen binding avidity towards at least two different antigens.

Certain embodiments provide methods of crosslinking glycoproteins, the methods comprising:
  a) providing a first glycoprotein comprising a terminal GlcNAc residue;
  b) providing a first modified sugar comprising a first chemical handle;
  c) contacting the first glycoprotein with the first modified sugar and a glycosyl transferase enzyme, wherein the glycosyl transferase enzyme catalyzes the attachment of the first modified sugar to the terminal GlcNAc residue of the first glycoprotein thereby forming a first modified glycoprotein;
  d) providing a first activating molecule comprising a first crosslinking group, a first reactive group and optionally a linker;
  e) contacting the first modified glycoprotein with the first activating molecule, wherein the first activating molecule attaches to the first glycoprotein at the first chemical handle, thereby forming a first activated glycoprotein;
  f) providing a second glycoprotein comprising a terminal GlcNAc residue;
  g) providing a second modified sugar comprising a second chemical handle;
  h) contacting the second glycoprotein with the second modified sugar and the glycosyl transferase enzyme, wherein the glycosyl transferase enzyme catalyzes the attachment of the second modified sugar to the terminal GlcNAc residue of the second glycoprotein thereby forming a second modified glycoprotein;
  i) providing a second activating molecule comprising a second crosslinking group, a second reactive group and optionally a linker;
  j) contacting the second modified glycoprotein with the second activating molecule, wherein the second activating molecule attaches to the second modified glycoprotein at the second chemical handle, thereby forming a second activated glycoprotein; and
  k) contacting the first activated glycoprotein with the second activated glycoprotein, wherein the first crosslinking group of the first activated glycoprotein reacts with the second crosslinking group of the second activated glycoprotein, thereby forming the crosslinked glycoprotein.

In certain embodiments, the first and/or second glycoprotein is an antibody, an antibody fragment, or an Fc-fusion protein. In certain embodiments, the first glycoprotein is an antibody and the second glycoprotein is an antibody. In certain embodiments, the first glycoprotein is an antibody and the second glycoprotein is an antibody fragment. In certain embodiments, the first glycoprotein is an antibody and the second glycoprotein is an Fc-fusion protein. In certain embodiments, the first glycoprotein is an antibody fragment and the second glycoprotein is an antibody. In certain embodiments, the first glycoprotein is an antibody fragment and the second glycoprotein is an antibody fragment. In certain embodiments, the first glycoprotein is an antibody fragment and the second glycoprotein is an Fc-fusion protein. In certain embodiments, the first glycoprotein is an Fc-fusion protein and the second glycoprotein is an antibody. In certain embodiments, the first glycoprotein is an Fc-fusion protein and the second glycoprotein is an antibody fragment. In certain embodiments, the first glycoprotein is an Fc-fusion protein and the second glycoprotein is an Fc-fusion protein. In certain embodiments, the antibody fragment is an Fc protein. In certain embodiments, the Fc protein is an Fc protein scaffold.

In certain embodiments, the first glycoprotein and the second glycoprotein contain a single crosslink. In certain embodiments, the first glycoprotein and the second glycoprotein contain two crosslinks.

In certain embodiments, the terminal GlcNAc residue on the first glycoprotein and/or second glycoprotein is attached to an asparagine (Asn). In certain embodiments, the asparagine is located on the Fc region of an antibody or antibody fragment. In certain embodiments, the asparagine on the Fc region is at amino acid position 287 (Asn287).

Certain embodiments provide methods of crosslinking antibodies, antibody fragments comprising a terminal GlcNAc residue, and/or Fc-fusion proteins to produce a bispecific antibody or antibody conjugate, the methods comprising:
  a) providing:
    i) a first antibody comprising a terminal GlcNAc residue,
    ii) a first antibody fragment comprising a terminal GlcNAc residue, or
    iii) a first Fc-fusion protein comprising a terminal GlcNAc residue;
  b) providing a first modified sugar comprising a first chemical handle;
  c) contacting the first antibody, first antibody fragment or first Fc-fusion protein with the first modified sugar and a glycosyl transferase enzyme, wherein the glycosyl transferase enzyme catalyzes the attachment of the first modified sugar to the terminal GlcNAc residue of the first antibody, first antibody fragment, or first Fc-fusion protein thereby forming a first modified antibody, a first modified antibody fragment, or a first modified Fc-fusion protein;

d) providing a first activating molecule comprising a first crosslinking group, a first reactive group, and optionally a linker;

e) contacting the first modified antibody, first modified antibody fragment, or first modified Fc-fusion protein with the first activating molecule, wherein the first activating molecule attaches to the first modified antibody, first modified antibody fragment, or first Fc-fusion protein at the first chemical handle, thereby forming a first activated antibody, first activated antibody fragment or first activated Fc-fusion protein;

f) providing:
iv) a second antibody comprising a terminal GlcNAc residue,
v) a second antibody fragment comprising a terminal GlcNAc residue, or
vi) a second Fc-fusion protein comprising a terminal GlcNAc residue;

g) providing a second modified sugar comprising a second chemical handle;

h) contacting the second antibody, second antibody fragment or second Fc-fusion protein with the second modified sugar and the glycosyl transferase enzyme, wherein the glycosyl transferase enzyme catalyzes the attachment of the second modified sugar to the terminal GlcNAc residue of the second antibody thereby forming a second modified antibody, a second modified antibody fragment, or a second modified Fc-fusion protein;

i) providing a second activating molecule comprising a second crosslinking group, a second reactive group and optionally, a linker;

j) contacting the second modified antibody, second modified antibody fragment, or second modified Fc-fusion protein with the second activating molecule, wherein the second activating molecule attaches to the second modified antibody, second modified antibody fragment, or second modified Fc-fusion protein at the second chemical handle, thereby forming a second activated antibody, a second activated antibody fragment, or a second modified Fc-fusion protein; and k) contacting the first activated antibody, first activated antibody fragment, or first activated Fc-fusion protein with the second activated antibody, second activated antibody fragment, or second activated Fc-fusion protein, wherein the first crosslinking group of the first activated antibody, first activated antibody fragment, or first activated Fc-fusion protein reacts with the second crosslinking group of the second activated antibody, second activated antibody fragment, or second activated Fc-fusion protein, thereby forming the bispecific antibody or antibody conjugate.

In certain embodiments, the first antibody fragment or the second antibody fragment is an Fc protein. In certain embodiments, the Fc protein is an Fc protein scaffold and the antibody conjugate is an antibody-Fc protein scaffold conjugate.

In certain embodiments, the first antibody, first antibody fragment, or first Fc-fusion protein and the second antibody, second antibody fragment or second Fc-fusion protein contain a single crosslink. In certain embodiments, the first antibody, first antibody fragment or first Fc-fusion protein and the second antibody, second antibody fragment or second Fc-fusion protein contain two crosslinks.

In certain embodiments, the terminal GlcNAc residue on the first antibody, first antibody fragment or first Fc-fusion protein and/or second antibody, second antibody fragment or second Fc-fusion protein is attached to an asparagine. In certain embodiments, the asparagine is located on the Fc region of an antibody or antibody fragment. In certain embodiments, the asparagine on the Fc region is at amino acid position 287 (Asn287).

In certain embodiments, methods are provided for making bispecific antibodies or antibody conjugates, the methods comprising:

a) providing a first activated antibody, first activated antibody fragment, or first activated Fc-fusion protein comprising a first activating molecule comprising a first crosslinking group, a first reactive group and optionally, a linker;

b) providing a second activated antibody, second activated antibody fragment, or second activated Fc-fusion protein comprising a second activating molecule comprising a second crosslinking group, a second reactive group and optionally, a linker; and c) contacting the first activated antibody, first activated antibody fragment, or first activated Fc-fusion protein with the second activated antibody, second activated antibody fragment, or second activated Fc-fusion protein, wherein the first crosslinking group of the first activated antibody, first activated antibody fragment, or first activated Fc-fusion protein reacts with the second crosslinking group of the second activated antibody, second activated antibody fragment, or second activated Fc-fusion protein, thereby forming the bispecific antibody or antibody conjugate.

In certain embodiments, the first activated antibody fragment or the second activated antibody fragment is an Fc protein. In certain embodiments, the Fc protein is an Fc protein scaffold and the antibody conjugate is an antibody-Fc protein scaffold conjugate.

In certain embodiments, the first antibody, first antibody fragment, or first Fc-fusion protein and the second antibody, second antibody fragment or second Fc-fusion protein contain a single crosslink. In certain embodiments, the first antibody, first antibody fragment or first Fc-fusion protein and the second antibody, second antibody fragment or second Fc-fusion protein contain two crosslinks.

In certain embodiments, the terminal GlcNAc residue on the first antibody, first antibody fragment or first Fc-fusion protein and/or second antibody, second antibody fragment or second Fc-fusion protein is attached to an asparagine. In certain embodiments, the asparagine is located on the Fc region of an antibody or antibody fragment. In certain embodiments, the asparagine on the Fc region is at amino acid position 287 (Asn287).

In certain embodiments, the first antibody, first antibody fragment, or first Fc-fusion protein and the second antibody, second antibody fragment, or second Fc-fusion protein are the same. In certain embodiments, the first antibody, first antibody fragment or first Fc-fusion protein and the second antibody, second antibody fragment, or second Fc-fusion protein are different. In certain embodiments, a first antibody is provided in step (a) and a second antibody is provided in step (f). In certain embodiments, an antibody is provided in step (a) and an antibody fragment is provided in step (f). In certain embodiments, an antibody is provided in step (a) and an Fc-fusion protein is provided in step (f). In certain embodiments, an antibody fragment is provided in step (a) and an antibody is provided in step (f). In certain embodiments, a first antibody fragment is provided in step (a) and a second antibody fragment is provided in step (f). In certain embodiments, an antibody fragment is provided in step (a) and an Fc-fusion protein is provided in step (f). In certain embodiments, an Fc-fusion protein is provided in step (a) and an antibody is provided in step (f). In certain embodiments, an Fc-fusion protein is provided in step (a) and an antibody fragment is provided in step (f). In certain embodiments, a first Fc-fusion protein is provided in step (a) and a second Fc-fusion protein is provided in step (f).

In certain embodiments, two or more antibodies, antibody fragments comprising a terminal GlcNAc residue, or Fc-fusion proteins can be crosslinked to form a bispecific antibody. In certain embodiments, three or more antibodies, antibody fragments comprising a terminal GlcNAc residue, or Fc-fusion proteins can be crosslinked to form a bispecific antibody. In certain embodiments, four or more antibodies, antibody fragments comprising a terminal GlcNAc residue, or Fc-fusion proteins can be crosslinked to form a bispecific antibody.

In certain embodiments, methods are provided for cross-linking two or more portions of the same antibody, antibody fragment comprising a terminal GlcNAc reside, or Fc fusion protein, the methods comprising:
 a) providing:
  i) an antibody comprising a terminal GlcNAc residue,
  ii) an antibody fragment comprising a terminal GlcNAc residue, or
  iii) a Fc-fusion protein comprising a terminal GlcNAc residue;
 b) providing at least one modified sugar comprising a chemical handle;
 c) contacting the antibody, antibody fragment or Fc-fusion protein with the at least one modified sugar and a glycosyl transferase enzyme, wherein the glycosyl transferase enzyme catalyzes the attachment of the at least one modified sugar to the terminal GlcNAc residue of the antibody, antibody fragment, or Fc-fusion protein thereby forming a modified antibody, a modified antibody fragment, or a modified Fc-fusion protein;
 d) providing a first activating molecule comprising a first crosslinking group, a first reactive group, and optionally, a linker, and a second activating molecule comprising a second crosslinking group, a second reactive group and optionally, a linker; and
 e) contacting the modified antibody, modified antibody fragment, or modified Fc-fusion protein with the first activating molecule and the second activating molecule, wherein the first activating molecule and the second activating molecule attach to the modified antibody, modified antibody fragment, or modified Fc-fusion protein at the chemical handle, thereby forming an activated antibody, an activated antibody fragment, or a modified Fc-fusion protein;
 wherein the first crosslinking group reacts with the second crosslinking group thereby forming the crosslinked antibody.

In certain embodiments, the first modified sugar comprising a first chemical handle and the second modified sugar comprising a second chemical handle are different. In certain embodiments, the first modified sugar comprising a first chemical handle and the second modified sugar comprising a second chemical handle are the same. In certain embodiments, the first and second chemical handles are the same. In certain embodiments, the first and second chemical handles are different. In certain embodiments, the chemical handle is selected from an alkyne-reactive group, an azide-reactive group, a Diels-Alder diene, a Diels-Alder dienophile, a straight chain or branched $C_1$-$C_{12}$ carbon chain bearing a carbonyl group, a —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), or —$ONH_2$ (aminooxy), wherein each $R^1$, $R^2$, and $R^3$ is independently H or alkyl having 1-6 carbons. In certain embodiments, the chemical handle of the first modified sugar and/or the second modified sugar comprises an azide group, an alkyne group, a cycloalkene group, a ketone group, an oxime group or a nitrile oxide group. In certain embodiments, the first modified sugar and/or the second modified sugar is UDP-GalNAz, UDP-GalKyne, UDP-Gal-Cyclopropene, UDP-GalKetone, UDP-Gal-Oxime or UDP-Gal-Nitrile oxide. In certain preferred embodiments, the first and/or second modified sugar comprising a chemical handle is UDP-GalNAz.

In certain embodiments, the chemical handle comprises an azide group, and the reactive group comprises a terminal triarylphosphine, terminal alkyne, or activated alkyne group; or the chemical handle comprises a terminal triarylphosphine, terminal alkyne or activated alkyne group, and the reactive group comprises an azide group. In certain embodiments, the activated alkyne comprises a dibenzocyclooctyne group.

In certain embodiments, the chemical handle comprises an oxime group or a nitrile oxide group and the reactive group comprises an activated alkyne group. In certain embodiments, the chemical handle comprises an activated alkyne group and the reactive group comprises an oxime group or a nitrile oxide group. In certain embodiments, the activated alkyne comprises a dibenzocyclooctyne group.

In certain embodiments, the chemical handle comprises a Diels-Alder diene and the reactive group comprises a Diels-Alder dienophile; or the chemical handle comprises a Diels-Alder dienophile and the reactive group comprises a Diels-Alder diene.

In certain embodiments, the chemical handle comprises a straight chain or branched $C_1$-$C_{12}$ carbon chain bearing a carbonyl group, and the reactive group comprises a —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), or —$ONH_2$ (aminooxy), wherein each $R^1$, $R^2$, and $R^3$ is independently H or alkyl having 1-6 carbons.

In certain embodiments, the chemical handle comprises a cycloalkene and the reactive group comprises a tetrazine.

In certain embodiments, the first reactive group of the first activating molecule is selected from a dibenzocyclooctyne, a difluorocyclooctyne, an aza-dibenzocyclooctyne, or a cyclononyne. In certain embodiments, the first reactive group is 4-dibenzocyclooctynol.

In certain embodiments, the first crosslinking group of the first activating molecule is a cycloalkene or a tetrazine. In certain embodiments, the first crosslinking group of the first activating molecule is a trans-cyclooctene (TCO), a cyclopropene, or a tetrazine.

In certain embodiments, the second reactive group of the second activating molecule is selected from a dibenzocyclooctyne, a difluorocyclooctyne, an aza-dibenzocyclooctyne, or a cyclononyne. In certain embodiments, the second reactive group is 4-dibenzocyclooctynol. In certain embodiments, the second crosslinking group of the second activating molecule is a trans-cyclooctene (TCO), a cyclopropene, or a tetrazine.

In certain embodiments, the first crosslinking group comprises a trans-cyclooctene or a cyclopropene and the second crosslinking group comprises a tetrazine. In certain embodiments, the first crosslinking group comprises a tetrazine and the second crosslinking group comprises a trans-cyclooctene or a cyclopropene.

In certain embodiments, the first activating molecule or second activating molecule comprises a linker. In certain embodiments, the first activating molecule and second activating molecule comprises a linker. In certain embodiments, the linker of the first and second activating molecule is the same. In certain embodiments, linker of the first and second activating molecule is different. In certain embodiments, the linker comprises one or more polyethylene glycol (PEG) groups. In certain embodiments, the linker comprises 1 to 300 PEG groups. In certain embodiments, the linker comprises 1 to 250 PEG groups. In certain embodiments, the linker comprises 1 to 200 PEG groups. In certain embodiments, the linker comprises 1 to 150 PEG groups. In certain embodiments, the linker comprises 1 to 100 PEG groups. In certain embodiments, the linker comprises 1 to 75 PEG groups. In certain embodiments, the linker comprises 1 to 50 PEG groups. In certain embodiments, the linker comprises 1 to 40 PEG groups. In certain embodiments, the linker comprises 1 to 30 PEG groups. In certain embodiments, the linker comprises 1 to 25 PEG groups. In certain embodiment, the linker comprises 1 to 20 PEG groups. In certain embodiments, the linker comprises 1 to 15 PEG groups. In certain embodiments, the linker comprises 1 to 10 PEG groups. In certain embodiments, the linker comprises 1 to 5 PEG groups. In certain embodiments, the linker comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45 46, 47, 48, 49 or 50 PEG groups.

In certain embodiments, the galactosyl transferase enzyme is a mutant galactosyl transferase enzyme. In certain preferred embodiments, the mutant galactosyl transferase enzyme is a Y289L mutant galactosyl transferase enzyme.

In certain embodiments, step (c) is performed in a solution substantially free of proteases.

In certain embodiments, the first antibody comprising a terminal GlcNAc residue or the second antibody comprising a terminal GlcNAc residue is obtained by β-galactosidase enzymatic activity. In certain embodiments, the first antibody fragment comprising a terminal GlcNAc residue or the second antibody fragment comprising a terminal GlcNAc residue is obtained by β-galactosidase enzymatic activity. In certain embodiments, the first Fc-fusion protein comprising a terminal GlcNAc residue or the second Fc-fusion protein comprising a terminal GlcNAc residue is obtained by β-galactosidase enzymatic activity.

In certain embodiments, the first antibody comprising a terminal GlcNAc residue and the second antibody comprising a terminal GlcNAc residue are obtained by β-galactosidase enzymatic activity. In certain embodiments, the first antibody fragment comprising a terminal GlcNAc residue and the second antibody fragment comprising a terminal GlcNAc residue are obtained by β-galactosidase enzymatic activity. In certain embodiments, the first Fc-fusion protein comprising a terminal GlcNAc residue and the second Fc-fusion protein comprising a terminal GlcNAc residue are obtained by β-galactosidase enzymatic activity.

In certain embodiments, the first antibody comprising a terminal GlcNAc residue or the second antibody comprising a terminal GlcNAc residue is obtained by endoglycosidase enzymatic activity. In certain embodiments, the first antibody fragment comprising a terminal GlcNAc residue or the second antibody fragment comprising a terminal GlcNAc residue is obtained by endoglycosidase enzymatic activity. In certain embodiments, the first Fc-fusion protein comprising a terminal GlcNAc residue or the second Fc-fusion protein comprising a terminal GlcNAc residue is obtained by endoglycosidase enzymatic activity.

In certain embodiments, the first antibody comprising a terminal GlcNAc residue and the second antibody comprising a terminal GlcNAc residue are obtained by endoglycosidase enzymatic activity. In certain embodiments, the first antibody fragment comprising a terminal GlcNAc residue and the second antibody fragment comprising a terminal GlcNAc residue are obtained by endoglycosidase enzymatic activity. In certain embodiments, the first Fc-fusion protein comprising a terminal GlcNAc residue and the second Fc-fusion protein comprising a terminal GlcNAc residue are obtained by endoglycosidase enzymatic activity.

In certain embodiments, the first antibody comprising a terminal GlcNAc residue is obtained by β-galactosidase enzymatic activity and the second antibody comprising a terminal GlcNAc residue is obtained by endoglycosidase enzymatic activity. In certain embodiments, the first antibody fragment comprising a terminal GlcNAc residue is obtained by β-galactosidase enzymatic activity and the second antibody fragment comprising a terminal GlcNAc residue is obtained by endoglycosidase enzymatic activity. In certain embodiments, the first Fc-fusion protein comprising a terminal GlcNAc residue is obtained by β-galactosidase enzymatic activity and the second Fc-fusion protein comprising a terminal GlcNAc residue is obtained by endoglycosidase enzymatic activity.

In certain embodiments, the first antibody comprising a terminal GlcNAc residue is obtained by endoglycosidase enzymatic activity and the second antibody comprising a terminal GlcNAc residue is obtained by β-galactosidase enzymatic activity. In certain embodiments, the first antibody fragment comprising a terminal GlcNAc residue is obtained by endoglycosidase enzymatic activity and the second antibody fragment comprising a terminal GlcNAc residue is obtained by β-galactosidase enzymatic activity. In certain embodiments, the first Fc-fusion protein comprising a terminal GlcNAc residue is obtained by endoglycosidase enzymatic activity and the second Fc-fusion protein comprising a terminal GlcNAc residue is obtained by β-galactosidase enzymatic activity In certain embodiments, the first antibody, first antibody fragment or first Fc-fusion protein is treated by β-galactosidase or endoglycosidase enzymatic activity and the second antibody, second antibody fragment, or second Fc-fusion protein is not treated by β-galactosidase or endoglycosidase enzymatic activity. In certain embodiments, the first antibody, first antibody fragment or Fc fusion protein is not treated by β-galactosidase or endoglycosidase enzymatic activity, and the second antibody, second antibody fragment, or second Fc-fusion protein is treated by β-galactosidase or endoglycosidase enzymatic activity. In certain embodiments, neither the first antibody, first antibody fragment or first Fc-fusion protein, nor the second antibody, second antibody fragment or second Fc-fusion protein is treated by β-galactosidase or endoglycosidase enzyme activity.

In certain embodiments, the method further comprises prior to step (a),
  providing a first antibody, a first antibody fragment, or a first Fc-fusion protein comprising an oligosaccharide having a GlcNAc-GlcNAc linkage;
  providing an enzyme to cleave the oligosaccharide at the GlcNAc-GlcNAc linkage; and
  contacting the first antibody, first antibody fragment, or first Fc-fusion protein comprising an oligosaccharide having a GlcNAc-GlcNAc linkage with the enzyme to provide the first antibody comprising a terminal GlcNAc residue, the first antibody fragment comprising a terminal GlcNAc residue or the first Fc-fusion protein comprising a terminal GlcNAc residue.

In certain embodiments, the method further comprises prior to step (f),
  providing a second antibody, a second antibody fragment, or a second Fc-fusion protein comprising an oligosaccharide having a GlcNAc-GlcNAc linkage;
  providing an enzyme to cleave the oligosaccharide at the GlcNAc-GlcNAc linkage; and
  contacting the second antibody, second antibody fragment, or second Fc-fusion protein comprising an oligosaccharide having a GlcNAc-GlcNAc linkage with the enzyme to provide the second antibody comprising a terminal GlcNAc residue, the second antibody fragment comprising a terminal GlcNAc residue, or the second Fc-fusion protein comprising a terminal GlcNAc residue.

Certain embodiments provide a method of making a bispecific antibody or antibody conjugate, the method comprising:
  a) providing a first antibody, a first antibody fragment, or a first Fc-fusion protein comprising an oligosaccharide having a GlcNAc-GlcNAc linkage;
  b) contacting the first antibody, first antibody fragment, or first Fc-fusion protein comprising an oligosaccharide having a GlcNAc-GlcNAc linkage with an endoglycosidase enzyme to provide a first antibody comprising a terminal GlcNAc residue, a first antibody fragment comprising a terminal GlcNAc residue or a first Fc-fusion protein comprising a terminal GlcNAc residue;
  c) providing a first UDP-GalNAZ;
  d) contacting the first antibody, first antibody fragment or first Fc-fusion protein with the first UDP-GalNAz and a glycosyl transferase enzyme, wherein the glycosyl transferase enzyme catalyzes the attachment of the first GalNAz group of the UDP-GalNAz to the terminal GlcNAc residue of the first antibody, antibody fragment or Fc-fusion protein, thereby forming a first modified antibody, a first modified antibody fragment, or a first modified Fc-fusion protein;
  e) providing a DIBO-PEG$_n$-TCO activating molecule, wherein n is 0-300;
  f) contacting the first modified antibody, first modified antibody fragment, or first modified Fc-fusion protein with the DIBO-PEG$_n$-TCO, wherein the DIBO group of the DIBO-PEG$_n$-TCO molecule attaches to the azide group of the first modified antibody, first modified antibody fragment, or first modified Fc fusion protein, thereby forming a first activated antibody, first activated antibody fragment or first activated Fc-fusion protein;
  g) providing a second antibody, a second antibody fragment, or a second Fc-fusion protein comprising an oligosaccharide having a GlcNAc-GlcNAc linkage;
  h) contacting the second antibody, second antibody fragment, or second Fc-fusion protein comprising an oligosaccharide having a GlcNAc-GlcNAc linkage with an endoglycosidase enzyme to provide a second antibody comprising a terminal GlcNAc residue, a second antibody fragment comprising a terminal GlcNAc residue or a second Fc-fusion protein comprising a terminal GlcNAc residue;
  i) providing a second UDP-GalNAz;
  j) contacting the second antibody, second antibody fragment or second Fc-fusion protein with the second UDP-GalNAz and the glycosyl transferase enzyme, wherein the glycosyl transferase enzyme catalyzes the attachment of the second GalNAz group of the second UDP-GalNAz to the terminal GlcNAc residue of the second antibody thereby forming a second modified antibody, a second modified antibody fragment, or a second modified Fc-fusion protein;
  k) providing a DIBO-PEG$_n$-Tetrazine activating molecule, wherein n is 0-300;
  l) contacting the second modified antibody, second modified antibody fragment, or second modified Fc-fusion protein with the DIBO-PEG$_n$-Tetrazine activating molecule, wherein the DIBO group of the DIBO-PEGn-Tetrazine activating molecule attaches to the azide group of the second modified antibody, second modified antibody fragment, or second modified Fc-fusion protein, thereby forming a second activated antibody, a second activated antibody fragment, or a second activated Fc-fusion protein; and
  m) contacting the first activated antibody, first activated antibody fragment, or first activated Fc-fusion protein with the second activated antibody, second activated antibody fragment, or second activated Fc-fusion protein, wherein the TCO group of the first activated antibody, first activated antibody fragment, or first activated Fc-fusion protein reacts with the Tetrazine group of the second activated antibody, second activated antibody fragment, or second activated Fc-fusion protein, thereby forming the bispecific antibody or antibody conjugate.

In certain embodiments, the enzyme is an endoglycosidase. In certain embodiments, the endoglycosidase is endoglycosidase S. In certain preferred embodiments, the endoglycosidase is endoglycosidase S2.

In certain embodiments, the method further comprises prior to step (a),
  providing a first antibody, a first antibody fragment, or a first Fc-fusion protein comprising an oligosaccharide having a NeuAc-Gal-GlcNAc linkage;
  providing an enzyme to cleave the oligosaccharide at the NeuAc-Gal-GlcNAc linkage; and
  contacting the first antibody, first antibody fragment, or first Fc-fusion protein comprising an oligosaccharide having a NeuAc-Gal-GlcNAc linkage with the enzyme to provide a first antibody, first antibody fragment, or first Fc-fusion protein comprising an oligosaccharide having a Gal-GlcNAc linkage.

In certain embodiments, the enzyme is a sialidase.

In certain embodiments, the method further comprises the steps of
  providing an enzyme to cleave the oligosaccharide at the Gal-GlcNAc linkage; and
  contacting the first antibody, first antibody fragment, or first Fc-fusion protein comprising an oligosaccharide having a Gal-GlcNAc linkage with the enzyme to provide the first antibody comprising a terminal GlcNAc residue, the first antibody fragment comprising a terminal GlcNAc residue, or the first Fc-fusion protein comprising a terminal GlcNAc residue.

In certain embodiments, the enzyme is a β-galactosidase.

In certain embodiments, the method further comprises prior to step (f),
providing a second antibody, a second antibody fragment, or a second Fc-fusion protein comprising an oligosaccharide having a NeuAc-Gal-GlcNAc linkage;
providing an enzyme to cleave the oligosaccharide at the NeuAc-Gal-GlcNAc linkage; and
contacting the second antibody, second antibody fragment, or second Fc-fusion protein comprising an oligosaccharide having a NeuAc-Gal-GlcNAc linkage with the enzyme to provide a second antibody, second antibody fragment, or second Fc-fusion protein comprising an oligosaccharide having a Gal-GlcNAc linkage.

In certain embodiments, the enzyme is a sialidase.

In certain embodiments, the method further comprises the steps of
providing an enzyme to cleave the oligosaccharide at the Gal-GlcNAc linkage; and
contacting the second antibody, second antibody fragment, or second Fc-fusion protein comprising an oligosaccharide having a Gal-GlcNAc linkage with the enzyme to provide the second antibody comprising a terminal GlcNAc residue, the second antibody fragment comprising a terminal GlcNAc residue, or the second Fc-fusion protein comprising a terminal GlcNAc residue.

In certain embodiments, the enzyme is a β-galactosidase.

In certain embodiments, the method further comprises prior to step (a),
providing a first antibody, first antibody fragment or a first Fc-fusion protein comprising an oligosaccharide having a Gal-GlcNAc linkage;
providing an enzyme to cleave the oligosaccharide at the Gal-GlcNAc linkage; and
contacting the first antibody, first antibody fragment or a first Fc-fusion protein comprising an oligosaccharide having a Gal-GlcNAc linkage with the enzyme to provide the first antibody comprising a terminal GlcNAc residue, the first antibody fragment comprising a terminal GlcNAc residue or the first Fc-fusion protein comprising a terminal GlcNAc residue.

In certain embodiments, the method further comprises prior to step (f),
providing a second antibody, second antibody fragment or second Fc-fusion protein comprising an oligosaccharide having a Gal-GlcNAc linkage;
providing an enzyme to cleave the oligosaccharide at the Gal-GlcNAc linkage; and
contacting the second antibody, second antibody fragment or second Fc-fusion protein comprising an oligosaccharide having a Gal-GlcNAc linkage with the enzyme to provide the second antibody comprising a terminal GlcNAc residue, the second antibody fragment comprising a terminal GlcNAc residue, or the second Fc-fusion protein comprising a terminal GlcNAc residue.

In certain embodiments, the enzyme is a β-galactosidase.

In certain embodiments of any of the methods described herein,
(i) steps (a) through (e) are performed before steps (f) through (j);
(ii) steps (a) through (e) are performed after steps (f) through (j); or
(iii) steps (a) through (e) are performed concurrently with steps (f) through (j).

In certain embodiments, the bispecific antibodies and/or antibody conjugates provided herein are obtained from contacting a first activated antibody, a first activated antibody fragment or a first activated Fc-fusion protein comprising a first crosslinking group with a second activated antibody, a second activated antibody fragment, or a second activated Fc-fusion protein comprising a second crosslinking group, wherein the first crosslinking group of the first activated antibody, first activated antibody fragment, or first activated Fc-fusion protein reacts with the second crosslinking group of the second activated antibody, second activated antibody fragment, or second activated Fc-fusion protein, thereby forming the bispecific antibody or antibody conjugate. In certain embodiments, the first activated antibody fragment or the second activated antibody fragment is an Fc protein. In certain embodiments, the Fc protein is an Fc protein scaffold and the antibody conjugate is an antibody-Fc protein scaffold conjugate.

In certain embodiments, the first antibody, first antibody fragment, or first Fc-fusion protein and the second antibody, second antibody fragment or second Fc-fusion protein contain a single crosslink. In certain embodiments, the first antibody, first antibody fragment or first Fc-fusion protein and the second antibody, second antibody fragment or second Fc-fusion protein contain two crosslinks.

In certain embodiments, the terminal GlcNAc residue on the first antibody, first antibody fragment or first Fc-fusion protein and/or second antibody, second antibody fragment or second Fc-fusion protein is attached to an asparagine. In certain embodiments, the asparagine is located on the Fc region of an antibody or antibody fragment. In certain embodiments, the asparagine on the Fc region is at amino acid position 287 (Asn287).

In certain embodiments, the bispecific antibodies or antibody conjugates are at least 50% pure. In certain embodiments, the bispecific antibodies or antibody conjugates are at least 60% pure. In certain embodiments, the bispecific antibodies or antibody conjugates are at least 70% pure. In certain embodiments, the bispecific antibodies or antibody conjugates are at least 80% pure. In certain embodiments, the bispecific antibodies or antibody conjugates are at least 90% pure. In certain embodiments, the bispecific antibodies or antibody conjugates are at least 91%, at least 92%, at least 93%, at least 94% or at least 95% pure. In certain embodiments, the purity of the bispecific antibodies or antibody conjugates is compared to multiply crosslinked higher molecular weight antibody or antibody conjugate species.

In certain embodiments, the bispecific antibodies and/or antibody conjugates provided herein are obtained by any of the methods described herein. In certain embodiments, the bispecific antibodies and/or antibody conjugates provided herein are obtained by combining a first antibody with a second antibody. In certain embodiments, the bispecific antibodies and/or antibody conjugates provided herein are obtained by combining a first antibody with a second antibody fragment comprising a terminal GlcNAc residue. In certain embodiments, the bispecific antibodies and/or antibody conjugates provided herein are obtained by combining a first antibody with a second Fc-fusion protein. In certain embodiments, the second antibody fragment is an Fc protein. In certain embodiments, the Fc protein is an Fc protein scaffold and the antibody conjugate is an antibody-Fc protein scaffold conjugate.

In certain embodiments, bispecific antibodies and/or antibody conjugates are provided that are obtained by combining a first antibody fragment comprising a terminal GlcNAc residue with a second antibody. In certain embodiments, bispecific antibodies and/or antibody conjugates are provided that are obtained by combining a first antibody fragment comprising a terminal GlcNAc residue with a second antibody fragment comprising a terminal GlcNAc residue. In certain embodiments, bispecific antibodies and/or antibody conjugates are provided that are obtained by combining a first antibody fragment comprising a terminal GlcNAc residue with a second Fc-fusion protein. In certain embodiments, the first or second antibody fragment is an Fc protein. In certain embodiments, the Fc protein is an Fc protein scaffold and the antibody conjugate is an antibody-Fc protein scaffold conjugate.

In certain embodiments, bispecific antibodies and/or antibody conjugates are provided that are obtained by combining a first Fc-fusion protein with a second antibody. In certain embodiments, bispecific antibodies and/or antibody conjugates are provided that are obtained by combining a first Fc-fusion protein with a second antibody fragment comprising a terminal GlcNAc residue. In certain embodiments, bispecific antibodies and/or antibody conjugates are provided that are obtained by combining a first Fc-fusion protein with a second Fc-fusion protein. In certain embodiments, the first or second antibody fragment is an Fc protein. In certain embodiments, the Fc protein is an Fc protein scaffold and the antibody conjugate is an antibody-Fc protein scaffold conjugate.

In certain embodiments, the first antibody, first antibody fragment or first Fc-fusion protein and the second antibody, second antibody fragment, or second Fc-fusion protein are the same. In certain embodiments, the first antibody, first antibody fragment, or first Fc-fusion protein and the second antibody, second antibody fragment, or second Fc-fusion protein are different. In certain embodiments, one antibody is crosslinked to itself. In certain embodiments, two antibodies, antibody fragments, and/or Fc-fusion proteins are crosslinked to form a bispecific antibody. In certain embodiments, three antibodies, antibody fragments, and/or Fc-fusion proteins are crosslinked to form a bispecific antibody. In certain embodiments, four antibodies, antibody fragments, and/or Fc-fusion proteins are crosslinked to form a bispecific antibody. In certain embodiments, one, two, three, four, or more antibodies, antibody fragments, and/or Fc-fusion proteins are crosslinked to form a bispecific antibody.

In certain embodiments, a method for screening bispecific antibodies and/or antibody conjugates is provided, the method comprising:
a) providing:
  i) a first antibody comprising a terminal GlcNAc residue,
  ii) a first antibody fragment comprising a terminal GlcNAc residue, or
  iii) a first Fc-fusion protein comprising a terminal GlcNAc residue;
b) providing a first modified sugar comprising a first chemical handle;
c) contacting the first antibody, first antibody fragment or first Fc-fusion protein with the first modified sugar and a glycosyl transferase enzyme, wherein the glycosyl transferase enzyme catalyzes the attachment of the first modified sugar to the terminal GlcNAc residue of the first antibody, first antibody fragment, or first Fc-fusion protein thereby forming a first modified antibody, a first modified antibody fragment, or a first modified Fc-fusion protein;
d) providing a first activating molecule comprising a first crosslinking group, a first reactive group, and optionally a linker;
e) contacting the first modified antibody, first modified antibody fragment, or first modified Fc-fusion protein with the first activating molecule, wherein the first activating molecule attaches to the first modified antibody, first modified antibody fragment, or first Fc-fusion protein at the first chemical handle, thereby forming a first activated antibody, first activated antibody fragment or first activated Fc-fusion protein;
f) providing:
  iv) a second antibody comprising a terminal GlcNAc residue,
  v) a second antibody fragment comprising a terminal GlcNAc residue, or
  vi) a second Fc-fusion protein comprising a terminal GlcNAc residue;
g) providing a second modified sugar comprising a second chemical handle;
h) contacting the second antibody, second antibody fragment or second Fc-fusion protein with the second modified sugar and the glycosyl transferase enzyme, wherein the glycosyl transferase enzyme catalyzes the attachment of the second modified sugar to the terminal GlcNAc residue of the second antibody thereby forming a second modified antibody, a second modified antibody fragment, or a second modified Fc-fusion protein;
i) providing a second activating molecule comprising a second crosslinking group, a second reactive group and optionally, a linker;
j) contacting the second modified antibody, second modified antibody fragment, or second modified Fc-fusion protein with the second activating molecule, wherein the second activating molecule attaches to the second modified antibody, second modified antibody fragment, or second modified Fc-fusion protein at the second chemical handle, thereby forming a second activated antibody, a second activated antibody fragment, or a second modified Fc-fusion protein;
k) contacting the first activated antibody, first activated antibody fragment, or first activated Fc-fusion protein with the second activated antibody, second activated antibody fragment, or second activated Fc-fusion protein, wherein the first crosslinking group of the first activated antibody, first activated antibody fragment, or first activated Fc-fusion protein reacts with the second crosslinking group of the second activated antibody, second activated antibody fragment, or second activated Fc-fusion protein, thereby forming the bispecific antibody or antibody conjugate; and
l) analyzing the bispecific antibody or antibody conjugate for functionality.

In certain embodiments, methods are provided for making bispecific antibodies or antibody conjugates, the methods comprising:
a) providing a first activated antibody, first activated antibody fragment, or first activated Fc-fusion protein comprising a first activating molecule comprising a first crosslinking group, a first reactive group and optionally, a linker;
b) providing a second activated antibody, second activated antibody fragment, or second activated Fc-fusion protein comprising a second activating molecule comprising a second crosslinking group, a second reactive group and optionally, a linker;

c) contacting the first activated antibody, first activated antibody fragment, or first activated Fc-fusion protein with the second activated antibody, second activated antibody fragment, or second activated Fc-fusion protein, wherein the first crosslinking group of the first activated antibody, first activated antibody fragment, or first activated Fc-fusion protein reacts with the second crosslinking group of the second activated antibody, second activated antibody fragment, or second activated Fc-fusion protein, thereby forming the bispecific antibody or antibody conjugate; and d) analyzing the bispecific antibody or antibody conjugate for functionality.

In certain embodiments, the bispecific antibodies or antibody conjugates are analyzed by gel electrophoresis. In certain embodiments, the bispecific antibodies or antibody conjugates are analyzed by fluorescence microscopy. In certain embodiments, the bispecific antibodies or antibody conjugates are analyzed by mass spectroscopy.

In certain embodiments, kits are provided, wherein the kits comprise:

a first modified sugar comprising a first chemical handle;

a second modified sugar comprising a second chemical handle;

a first activating molecule comprising a first crosslinking group, a first reactive group and optionally, a linker;

a second activating molecule comprising a second crosslinking group, a second reactive group and optionally, a linker;

a galactosyl transferase enzyme; and instructions for use in any of the methods described herein.

In certain embodiments, the kits further comprise a β-galactosidase enzyme. In certain embodiments, the kits further comprise an endoglycosidase enzyme. In certain embodiments, the endoglycosidase enzyme is endoglycosidase S. In certain preferred embodiments, the endoglycosidase enzyme is endoglycosidase S2.

In certain embodiments, the first modified sugar comprising a first chemical handle and the second modified sugar comprising a second chemical handle are different. In certain embodiments, the first modified sugar comprising a first chemical handle and the second modified sugar comprising a second chemical handle are the same. In certain embodiments, the first and second chemical handles are the same. In certain embodiments, the first and second chemical handles are different. In certain embodiments, the chemical handle is selected from an alkyne-reactive group, an azide-reactive group, a Diels-Alder diene, a Diels-Alder dienophile, a straight chain or branched $C_1$-$C_{12}$ carbon chain bearing a carbonyl group, a —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), or —$ONH_2$ (aminooxy), wherein each $R^1$, $R^2$, and $R^3$ is independently H or alkyl having 1-6 carbons. In certain embodiments, the chemical handle of the first modified sugar and/or the second modified sugar comprises an azide group, an alkyne group, a ketone group, an oxime group or a nitrile oxide group. In certain embodiments, the first modified sugar and/or the second modified sugar is UDP-GalNAz, UDP-GalKyne, UDP-Gal-Cyclopropene, UDP-GalKetone, UDP-Gal-Oxime or UDP-Gal-Nitrile oxide. In certain embodiments, the first and/or second modified sugar comprising a chemical handle is UDP-GalNAz.

In certain embodiments, the chemical handle comprises an azide group and the reactive group comprises a terminal triarylphosphine, terminal alkyne, or activated alkyne group; or the chemical handle comprises a terminal triarylphosphine, terminal alkyne or activated alkyne group, and the reactive group comprises an azide group. In certain embodiments, the activated alkyne comprises a dibenzocyclooctyne group.

In certain embodiments, the chemical handle comprises an oxime group or a nitrile oxide group and the reactive group comprises an activated alkyne group. In certain embodiments, the chemical handle comprises an activated alkyne group and the reactive group comprises an oxime group or a nitrile oxide group. In certain embodiments, the activated alkyne comprises a dibenzocyclooctyne group.

In certain embodiments, the chemical handle comprises a Diels-Alder diene and the reactive group comprises a Diels-Alder dienophile; or the chemical handle comprises a Diels-Alder dienophile and the reactive group comprises a Diels-Alder diene.

In certain embodiments, the chemical handle comprises a straight chain or branched $C_1$-$C_{12}$ carbon chain bearing a carbonyl group, and the reactive group comprises a —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), or —$ONH_2$ (aminooxy), wherein each $R^1$, $R^2$, and $R^3$ is independently H or alkyl having 1-6 carbons.

In certain embodiments, the chemical handle comprises a cycloalkene and the reactive group comprises a tetrazine.

In certain embodiments, the first reactive group of the first activating molecule is selected from a dibenzocyclooctyne, a difluorocyclooctyne, an aza-dibenzocyclooctyne, or a cyclononyne. In certain embodiments, the first reactive group is 4-dibenzocyclooctynol.

In certain embodiments, the first crosslinking group of the first activating molecule is a cycloalkene or a tetrazine. In certain embodiments, the first crosslinking group of the first activating molecule is a trans-cyclooctene (TCO), a cyclopropene, or a tetrazine.

In certain embodiments, the first activating molecule comprises a trans-cyclooctene and a dibenzocyclooctyne.

In certain embodiments, the second reactive group of the second activating molecule is selected from a dibenzocyclooctyne, a difluorocyclooctyne, an aza-dibenzocyclooctyne, or a cyclononyne. In certain embodiments, the second reactive group is 4-dibenzocyclooctynol. In certain embodiments, the second crosslinking group of the second activating molecule is a trans-cyclooctene (TCO), a cyclopropene, or a tetrazine.

In certain embodiments, the first crosslinking group comprises a trans-cyclooctene or a cyclopropene and the second crosslinking group comprises a tetrazine. In certain embodiments, the first crosslinking group comprises a tetrazine and the second crosslinking group comprises a trans-cyclooctene or a cyclopropene.

In certain embodiments, the first or second activating molecule comprises a linker. In certain embodiments, the first and second activating molecule comprises a linker. In certain embodiments, the linkers of the first and second activating molecule are the same. In certain embodiments, the linkers of the first and second activating molecule are different. In certain embodiments, the linker comprises one or more polyethylene glycol (PEG) groups. In certain embodiments, the linker comprises 1 to 300 PEG groups. In certain embodiments, the linker comprises 1 to 250 PEG groups. In certain embodiments, the linker comprises 1 to 200 PEG groups. In certain embodiments, the linker comprises 1 to 150 PEG groups. In certain embodiments, the linker comprises 1 to 100 PEG groups. In certain embodiments, the linker comprises 1 to 75 PEG groups. In certain embodiments, the linker comprises 1 to 50 PEG groups. In certain embodiments, the linker comprises 1 to 40 PEG groups. In certain embodiments, the linker comprises 1 to 30 PEG groups. In certain embodiments, the linker comprises 1 to 25 PEG groups. In certain embodiment, the linker comprises 1 to 20 PEG groups. In certain embodiments, the linker comprises 1 to 15 PEG groups. In certain embodiments, the linker comprises 1 to 10 PEG groups. In certain embodiments, the linker comprises 1 to 5 PEG groups. In certain embodiments, the linker comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45 46, 47, 48, 49 or 50 PEG groups.

Certain embodiments provide pharmaceutical compositions comprising the bispecific antibodies or antibody conjugates disclosed herein. In certain embodiments, the pharmaceutical compositions further comprise a pharmaceutically acceptable carrier, pharmaceutically acceptable excipient or a pharmaceutically acceptable diluent.

Certain embodiments provide methods for producing an antibody-conjugated liposome, the methods comprising:
a) providing an activated antibody, activated antibody fragment, or activated Fc-fusion protein comprising a crosslinking group, a reactive group and optionally, a linker;
b) providing a liposome comprising at least one tetrazine-, trans-cyclooctene (TCO)- or cyclopropene-modified fatty acid; and
c) contacting the activated antibody, activated antibody fragment or activated Fc-fusion protein with the liposome, wherein the crosslinking group of the activated antibody, activated antibody fragment or activated Fc-fusion protein reacts with the tetrazine-modified fatty acid, the cyclopropene-modified fatty acid or the TCO-modified fatty acid of the liposome, thereby forming the antibody-conjugated liposome.

In certain embodiments, methods of producing an antibody-conjugated liposome are provided, the methods comprising:
a) providing
   i) an antibody comprising a terminal GlcNAc residue,
   ii) an antibody fragment comprising a terminal GlcNAc residue, or
   iii) an Fc-fusion protein comprising a terminal GlcNAc residue;
b) providing a modified sugar comprising a chemical handle;
c) contacting the antibody, antibody fragment or Fc-fusion protein with the modified sugar and a glycosyl transferase enzyme, wherein the glycosyl transferase enzyme catalyzes the attachment of the modified sugar to the terminal GlcNAc residue of the antibody to provide a modified antibody, a modified antibody fragment or a modified Fc-fusion protein;
d) providing an activating molecule comprising a crosslinking group, a reactive group and optionally a linker;
e) contacting the modified antibody, modified antibody fragment, or modified Fc-fusion protein with the activating molecule, wherein the activating molecule attaches to the modified antibody, modified antibody fragment or modified Fc-fusion protein at the chemical handle, thereby forming an activated antibody, an activated antibody fragment, or an activated Fc-fusion protein;
f) providing a liposome comprising at least one trans-cyclooctene (TCO)-modified fatty acid, cyclopropene-modified fatty acid or tetrazine-modified fatty acid; and
g) contacting the activated antibody, activated antibody fragment, or activated Fc-fusion protein with the liposome, wherein the crosslinking group of the activated antibody, activated antibody fragment, or activated Fc-fusion protein reacts with the trans-cyclooctene (TCO)-modified fatty acid, cyclopropene-modified fatty acid or tetrazine-modified fatty acid of the liposome, thereby forming the antibody-conjugated liposome.

In certain embodiments methods are provided for producing an antibody-conjugated liposome, the methods comprising:
a) providing
   i) an antibody comprising a terminal GlcNAc residue,
   ii) an antibody fragment comprising a terminal GlcNAc residue, or
   iii) an Fc-fusion protein comprising a terminal GlcNAc residue;
b) providing a modified sugar comprising a chemical handle;
c) contacting the antibody, antibody fragment or Fc-fusion protein with the modified sugar and a glycosyl transferase enzyme, wherein the glycosyl transferase enzyme catalyzes the attachment of the modified sugar to the terminal GlcNAc residue of the antibody to provide a modified antibody, a modified antibody fragment or a modified Fc-fusion protein;
d) providing fatty acid comprising a reactive group;
e) contacting the modified antibody, modified antibody fragment, or modified Fc-fusion protein with the fatty acid comprising a reactive group, wherein the reactive group attaches to the modified antibody, modified antibody fragment or modified Fc-fusion protein at the chemical handle, thereby forming a fatty acid-activated antibody, a fatty acid-activated antibody fragment, or a fatty acid-activated Fc-fusion protein;
f) providing a liposome; and
g) contacting the fatty acid-activated antibody, fatty acid-activated antibody fragment, or fatty acid-activated Fc-fusion protein with the liposome, wherein the fatty acid of the fatty acid-activated antibody, fatty acid-activated antibody fragment, or fatty acid-activated Fc-fusion protein is embedded into the liposome, thereby forming the antibody-conjugated liposome.

In certain embodiments, the modified sugar comprising a chemical handle is selected from an alkyne-reactive group, an azide-reactive group, a Diels-Alder diene, a Diels-Alder dienophile, a straight chain or branched $C_1$-$C_{12}$ carbon chain bearing a carbonyl group, a —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), or —$ONH_2$ (aminooxy), wherein each $R^1$, $R^2$, and $R^3$ is independently H or alkyl having 1-6 carbons. In certain embodiments, the chemical handle comprises an azide group, an alkyne group, a ketone group, an oxime group or a nitrile oxide group. In certain embodiments, the first modified sugar and/or the second modified sugar is UDP-GalNAz, UDP-GalKyne, UDP-Gal-Cyclopropene, UDP-GalKetone, UDP-Gal-Oxime or UDP-Gal-Nitrile oxide. In certain embodiments, the first and/or second modified sugar comprising a chemical handle is UDP-GalNAz.

In certain embodiments, the chemical handle comprises an azide group, and the reactive group comprises a terminal triarylphosphine, terminal alkyne, or activated alkyne group; or the chemical handle comprises a terminal triarylphosphine, terminal alkyne or activated alkyne group, and the reactive group comprises an azide group. In certain embodiments, the activated alkyne comprises a dibenzocyclooctyne group.

In certain embodiments, the chemical handle comprises an oxime group or a nitrile oxide group and the reactive group comprises an activated alkyne. In certain embodiments, the chemical handle comprises an activated alkyne and the reactive group comprises an oxime group or a nitrile oxide group.

In certain embodiments, the activated alkyne group is a dibenzocyclooctyne group.

In certain embodiments, the chemical handle comprises a Diels-Alder diene and the reactive group comprises a Diels-Alder dienophile; or the chemical handle comprises a Diels-Alder dienophile and the reactive group comprises a Diels-Alder diene.

In certain embodiments, the chemical handle comprises a straight chain or branched $C_1$-$C_{12}$ carbon chain bearing a carbonyl group, and the reactive group comprises a —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), or —$ONH_2$ (aminooxy), wherein each $R^1$, $R^2$, and $R^3$ is independently H or alkyl having 1-6 carbons.

In certain embodiments, the chemical handle comprises a cycloalkene and the reactive group comprises a tetrazine.

In certain embodiments, the first crosslinking group of the first activating molecule is a cycloalkene or a tetrazine. In certain embodiments, the crosslinking group is a trans-cyclooctene (TCO), a cyclopropene, or a tetrazine.

In certain embodiments, the glycosyl transferase enzyme is a mutant galactosyl transferase enzyme. In certain preferred embodiments, the mutant galactosyl transferase enzyme is a Y289L mutant galactosyl transferase enzyme.

In certain embodiments, the liposomes contain alkyne-modified lipids such as 15-hexadecynoic acid.

In certain embodiments, the method further comprises prior to step (a),
providing an antibody, antibody fragment or Fc-fusion protein comprising an oligosaccharide having a GlcNAc-GlcNAc linkage;
providing an enzyme to cleave the oligosaccharide at the GlcNAc-GlcNAc linkage; and
contacting the antibody, antibody fragment or Fc-fusion protein comprising an oligosaccharide having a GlcNAc-GlcNAc linkage with the enzyme to provide the antibody comprising a terminal GlcNAc residue, the antibody fragment comprising a terminal GlcNAc residue, or the Fc binding protein comprising a terminal GlcNAc residue.

In certain embodiments, the enzyme is an endoglycosidase. In a preferred embodiment, the endoglycosidase is endoglycosidase S or endoglycosidase S2.

In certain embodiments, the method further comprises prior to step (a),
providing an antibody, antibody fragment or Fc-fusion protein comprising an oligosaccharide having a NeuAc-Gal-GlcNAc linkage;
providing an enzyme to cleave the oligosaccharide at the NeuAc-Gal-GlcNAc linkage; and
contacting the antibody, antibody fragment or Fc-fusion protein comprising an oligosaccharide having a NeuAc-Gal-GlcNAc linkage with the enzyme to provide an antibody comprising an oligosaccharide having a Gal-GlcNAc linkage.

In certain embodiments, the enzyme is a sialidase.

In certain embodiments, the method further comprises the steps of
providing an enzyme to cleave the oligosaccharide at the Gal-GlcNAc linkage; and
contacting the antibody, antibody fragment or Fc-fusion protein comprising an oligosaccharide having a Gal-GlcNAc linkage with the enzyme to provide the antibody comprising a terminal GlcNAc residue, the antibody fragment comprising a terminal GlcNAc residue, or the Fc binding protein comprising a terminal GlcNAc residue.

In certain embodiments, the enzyme is a β-galactosidase.

In certain embodiments, the method further comprises prior to step (a),
providing an antibody, antibody fragment or Fc-fusion protein comprising an oligosaccharide having a Gal-GlcNAc linkage;
providing an enzyme to cleave the oligosaccharide at the Gal-GlcNAc linkage; and
contacting the antibody, antibody fragment or Fc-fusion protein comprising an oligosaccharide having a Gal-GlcNAc linkage with the enzyme to provide the antibody comprising a terminal GlcNAc residue, the antibody fragment comprising a terminal GlcNAc residue, or the Fc binding protein comprising a terminal GlcNAc residue.

In certain embodiments, the enzyme is a β-galactosidase.

Certain embodiments provide antibody-conjugated liposomes that are obtained by any of the methods provided herein. In certain embodiments, antibody-conjugated liposomes are provided that are obtained by combining an antibody with a modified liposome. In certain embodiments, antibody-conjugated liposomes are provided that are obtained by combining an antibody fragment comprising a terminal GlcNAc residue with a modified liposome. In certain embodiments, antibody-conjugated liposomes are provided that are obtained by combining an Fc-fusion protein with a modified liposome.

Certain embodiments provide pharmaceutical compositions comprising the antibody-conjugated liposomes disclosed herein. In certain embodiments, the pharmaceutical compositions further comprise a pharmaceutically acceptable carrier, pharmaceutically acceptable excipient or a pharmaceutically acceptable diluent.

Certain embodiments provide methods of producing an antibody-conjugated mRNA or an antibody-conjugated siRNA, the method comprising:
a) providing an activated antibody, antibody fragment or Fc-fusion protein comprising a crosslinking group, a reactive group and optionally, a linker;
b) providing an mRNA or an siRNA;

c) providing a trans-cyclooctene (TCO)-modified RNA polymer, a cyclopropene-modified RNA polymer or a tetrazine-modified RNA polymer;
d) contacting the mRNA or siRNA with the trans-cyclooctene (TCO)-, cyclopropene- or tetrazine-modified RNA binding polymer, wherein the modified RNA binding polymer binds to the mRNA or siRNA thereby forming a modified mRNA or modified siRNA; and
e) contacting the activated antibody, antibody fragment, or Fc-fusion protein with the modified mRNA or modified siRNA, wherein the crosslinking group of the activated antibody, antibody fragment, or Fc-fusion protein reacts with the TCO, cyclopropene or tetrazine moiety of the modified mRNA or modified siRNA, thereby forming the antibody-conjugated mRNA or antibody-conjugated siRNA.

Certain embodiments provide methods of producing an antibody-conjugated mRNA or antibody-conjugated siRNA, the method comprising:
a) providing
  i) an antibody comprising a terminal GlcNAc residue;
  ii) an antibody fragment comprising a terminal GlcNAc residue;
  iii) an Fc-fusion protein comprising a terminal GlcNAc residue;
b) providing a modified sugar comprising a chemical handle;
c) contacting the antibody, antibody fragment or Fc-fusion protein with the modified sugar and a glycosyl transferase enzyme, wherein the glycosyl transferase enzyme catalyzes the attachment of the modified sugar to the terminal GlcNAc residue of the antibody, antibody fragment, or Fc-fusion protein to provide a modified antibody, a modified antibody fragment, or a modified Fc-fusion protein;
d) providing an activating molecule comprising a crosslinking group, a reactive group and optionally a linker;
e) contacting the modified antibody, modified antibody fragment, or modified Fc-fusion protein with the activating molecule, wherein the activating molecule attaches to the modified antibody, modified antibody fragment, or modified Fc-fusion protein at the chemical handle, thereby forming an activated antibody, an activated antibody fragment, or an activated Fc-fusion protein;
f) providing an mRNA or an siRNA;
g) providing a trans-cyclooctene (TCO)-, cyclopropene- or tetrazine-modified RNA binding polymer;
h) contacting the mRNA or siRNA with the trans-cyclooctene (TCO)-, cyclopropene- or tetrazine-modified RNA binding polymer, wherein the modified RNA binding polymer binds to the mRNA or siRNA thereby forming a modified mRNA or modified siRNA; and
i) contacting the activated antibody, activated antibody fragment, or activated Fc-fusion protein with the modified mRNA or modified siRNA, wherein the crosslinking group of the activated antibody, activated antibody fragment, or activated Fc-fusion protein reacts with the TCO, cyclopropene or tetrazine moiety of the modified mRNA or modified siRNA, thereby forming the antibody-conjugated mRNA or antibody-conjugated siRNA.

In certain embodiments, the modified sugar comprising a chemical handle is selected from an alkyne-reactive group, an azide-reactive group, a Diels-Alder diene, a Diels-Alder dienophile, a straight chain or branched $C_1$-$C_{12}$ carbon chain bearing a carbonyl group, a —$NR^1NH_2$ (hydrazide), —$NR^1$(C=O)$NR^2NH_2$ (semicarbazide), —$NR^1$(C=S)$NR^2NH_2$ (thiosemicarbazide), —(C=O)$NR^1NH_2$ (carbonylhydrazide), —(C=S)$NR^1NH_2$ (thiocarbonylhydrazide), —($SO_2$)$NR^1NH_2$ (sulfonylhydrazide), —$NR^1NR^2$(C=O)$NR^3NH_2$ (carbazide), —$NR^1NR^2$(C=S)$NR^3NH_2$ (thiocarbazide), or —$ONH_2$ (aminooxy), wherein each $R^1$, $R^2$, and $R^3$ is independently H or alkyl having 1-6 carbons. In certain embodiments, the chemical handle comprises an azide group, an alkyne group, a ketone group, an oxime group or a nitrile oxide group. In certain embodiments, the first modified sugar and/or second modified sugar is UDP-GalNAz, UDP-GalKyne, UDP-Gal-Cyclopropene, UDP-GalKetone, UDP-Gal-Oxime or UDP-Gal-Nitrile oxide. In certain embodiments, the first and/or second modified sugar comprising a chemical handle is UDP-GalNAz.

In certain embodiments, the chemical handle comprises an azide group, and the reactive group comprises a terminal triarylphosphine, terminal alkyne, or activated alkyne group; or the chemical handle comprises a terminal triarylphosphine, terminal alkyne or activated alkyne group, and the reactive group comprises an azide group. In certain embodiments, the activated alkyne comprises a dibenzocyclooctyne group.

In certain embodiments, the chemical handle is an oxime group or a nitrile oxide group and the reactive group is an activated alkyne group. In certain embodiments, the chemical handle is an activated alkyne group and the reactive group is an oxime or a nitrile oxide group. In certain embodiments, the activated alkyne is a dibenzocyclooctyne group.

In certain embodiments, the chemical handle comprises a Diels-Alder diene and the reactive group comprises a Diels-Alder dienophile; or the chemical handle comprises a Diels-Alder dienophile and the reactive group comprises a Diels-Alder diene.

In certain embodiments, the chemical handle comprises a straight chain or branched $C_1$-$C_{12}$ carbon chain bearing a carbonyl group, and the reactive group comprises a —$NR^1NH_2$ (hydrazide), —$NR^1$(C=O)$NR^2NH_2$ (semicarbazide), —$NR^1$(C=S)$NR^2NH_2$ (thiosemicarbazide), —(C=O)$NR^1NH_2$ (carbonylhydrazide), —(C=S)$NR^1NH_2$ (thiocarbonylhydrazide), —($SO_2$)$NR^1NH_2$ (sulfonylhydrazide), —$NR^1NR^2$(C=O)$NR^3NH_2$ (carbazide), —$NR^1NR^2$(C=S)$NR^3NH_2$ (thiocarbazide), or —$ONH_2$ (aminooxy), wherein each $R^1$, $R^2$, and $R^3$ is independently H or alkyl having 1-6 carbons.

In certain embodiments, the chemical handle comprises a cycloalkene and the reactive group comprises a tetrazine.

In certain embodiments, the first crosslinking group of the first activating molecule is a cycloalkene or a tetrazine. In certain embodiments, the crosslinking group is a trans-cyclooctene (TCO), a cyclopropene, or a tetrazine.

In certain embodiments, the galactosyl transferase enzyme is a mutant galactosyl transferase enzyme. In certain preferred embodiments, the mutant galactosyl transferase enzyme is a Y289L mutant galactosyl transferase enzyme.

In certain embodiments, the method further comprises prior to step (a),
  providing an antibody, antibody fragment, or Fc-fusion protein comprising an oligosaccharide having a GlcNAc-GlcNAc linkage;
  providing an enzyme to cleave the oligosaccharide at the GlcNAc-GlcNAc linkage; and
  contacting the antibody, antibody fragment, or Fc-fusion protein comprising an oligosaccharide having a GlcNAc-GlcNAc linkage with the enzyme to provide the antibody comprising a terminal GlcNAc residue, the antibody fragment comprising a terminal GlcNAc, or the Fc-fusion protein comprising a terminal GlcNAc residue.

In certain embodiments, the enzyme is an endoglycosidase. In certain preferred embodiments, the endoglycosidase is endoglycosidase S or endoglycosidase S2.

In certain embodiments, the method further comprises prior to step (a),
providing an antibody, antibody fragment, or Fc-fusion protein comprising an oligosaccharide having a NeuAc-Gal-GlcNAc linkage;
providing an enzyme to cleave the oligosaccharide at the NeuAc-Gal-GlcNAc linkage; and
contacting the antibody, antibody fragment, or Fc-fusion protein comprising an oligosaccharide having a NeuAc-Gal-GlcNAc linkage with the enzyme to provide an antibody comprising an oligosaccharide having a Gal-GlcNAc linkage.

In certain embodiments, the enzyme is a sialidase.

In certain embodiments, the method further comprises the steps of
providing an enzyme to cleave the oligosaccharide at the Gal-GlcNAc linkage; and
contacting the antibody, antibody fragment, or Fc-fusion protein comprising an oligosaccharide having a Gal-GlcNAc linkage with the enzyme to provide the antibody comprising a terminal GlcNAc residue, the antibody fragment comprising a terminal GlcNAc, or the Fc-fusion protein comprising a terminal GlcNAc residue.

In certain embodiments, the enzyme is a β-galactosidase.

In certain embodiments, the method further comprises prior to step (a),
providing an antibody, antibody fragment, or Fc-fusion protein comprising an oligosaccharide having a Gal-GlcNAc linkage;
providing an enzyme to cleave the oligosaccharide at the Gal-GlcNAc linkage; and
contacting the antibody, antibody fragment, or Fc-fusion protein comprising an oligosaccharide having a Gal-GlcNAc linkage with the enzyme to provide the antibody comprising a terminal GlcNAc residue, the antibody fragment comprising a terminal GlcNAc, or the Fc-fusion protein comprising a terminal GlcNAc residue.

In certain embodiments, the enzyme is a β-galactosidase.

Certain embodiments provide antibody-conjugated mRNA or antibody-conjugated siRNA that are obtained by any of the methods provided herein. In certain embodiments, antibody-conjugated mRNA or antibody-conjugated siRNA are provided that are obtained by combining an antibody with a modified RNA binding polymer bound to an mRNA or an siRNA. In certain embodiments, antibody-conjugated mRNA or antibody-conjugated siRNA are provided that are obtained by combining an antibody fragment comprising a terminal GlcNAc residue with a modified RNA binding polymer bound to an mRNA or an siRNA. In certain embodiments, antibody-conjugated mRNA or antibody-conjugated siRNA are provided that are obtained by combining an Fc-fusion protein with a modified RNA binding polymer bound to an mRNA or an siRNA.

Certain embodiments provide pharmaceutical compositions comprising the antibody-conjugated mRNA or antibody-conjugated siRNA disclosed herein. In certain embodiments, the pharmaceutical compositions further comprise a pharmaceutically acceptable carrier, pharmaceutically acceptable excipient or a pharmaceutically acceptable diluent.

Certain embodiments provide for methods of treating a disease, disorder or condition in a subject in need thereof comprising administering the bispecific antibodies provided herein, the antibody conjugates provided herein, the pharmaceutical compositions provided herein, the antibody-conjugated liposomes provided herein, the antibody-conjugated mRNA or antibody-conjugated siRNA provided herein. In certain embodiments, the bispecific antibody, antibody conjugate, pharmaceutical composition, antibody-conjugated liposome, antibody-conjugated mRNA or antibody-conjugated siRNA is administered by parenteral administration comprising intravenous administration, subcutaneous administration, intraperitoneal administration, intramuscular administration, intravascular administration, intrathecal administration, intravitreal administration, or infusion. In certain embodiments, the bispecific antibody, antibody conjugate, pharmaceutical composition, antibody-conjugated liposome, antibody-conjugated mRNA or antibody-conjugated siRNA is administered by a microneedle device. In certain embodiments, the bispecific antibody, antibody conjugate, pharmaceutical composition, antibody-conjugated liposome, antibody-conjugated mRNA or antibody-conjugated siRNA is administered by topical, oral or nasal administration. In certain embodiments, the disease is a cancer, a pathogenic infection, an inflammatory disease, an autoimmune disease or a metabolic disease. In certain embodiments, the subject is a mammal. In certain embodiments, the antibody conjugate is an antibody-Fc protein scaffold conjugate.

Certain embodiments provide for methods of diagnosing a disease, disorder or condition using the bispecific antibodies, antibody conjugates, pharmaceutical compositions, antibody-conjugated liposomes, antibody-conjugated mRNA or antibody-conjugated siRNA provided herein.

In certain embodiments, methods for diagnosing a disease, disorder or condition in a subject are provided, the methods comprising:
(a) contacting a sample obtained from a subject suspected of having the disease with a bispecific antibody provided herein, an antibody conjugate provided herein, a pharmaceutical composition provided herein, an antibody-conjugated liposome provided herein, an antibody-conjugated mRNA or an antibody-conjugated siRNA provided herein to form a contacted sample;
(b) incubating the contacted sample for an appropriate amount of time to form an incubated sample;
(c) illuminating the incubated sample with an appropriate wavelength to form an illuminated sample; and
(d) detecting fluorescent emissions from the illuminated sample;
wherein the fluorescent emissions are used to diagnose or detect the disease.

Certain embodiments provide for the use of any of the methods, compositions or kits disclosed herein for the diagnosis of diseases, for example, cancer, including but not limited to breast cancer, prostate cancer, lung cancer, skin cancer, cancers of the reproductive tract, brain cancer, liver cancer, pancreatic cancer, stomach cancer, blood cancers (e.g., leukemia and lymphoma), sarcomas, melanomas, and the like.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

In FIG. 3A, the antibodies are contacted with activating molecules that have two DIBO groups each and in FIG. 3B, the antibodies are contacted with activating molecules that have one DIBO group each. The final degree of labeling (DOL) is 1 TCO group or 1 tetrazine group (FIG. 3A), or 2 TCO or tetrazine groups (FIG. 3B).

FIG. 13A shows the reducing gel with the predominant formation of 100 kD crosslinked heavy chain species (100 kD 2HC). FIG. 13B shows the non-reducing gel with the predominant formation of the 300 kD tetravalent bispecific antibody species (300 kD 2IgG). Directly below the gel is a densitometric scan of the gel after it was stained with SYPRO Ruby total protein gel stain and imaged. This site-specific, directional, conjugation method ensures the efficient yield of tetravalent bispecific species leaving the antibody binding domains intact, and preventing the formation of highly-crosslinked undesirable antibody complexes.

In FIG. 15A and FIG. 15B, the fluorescence scans of the DIBO-Dye-488-labeled proteins are shown in the left panels and correspond to the Dye-488 lanes in the SYPRO Ruby stained gels. These were used to determine the DOL of the azide-activated proteins. FIG. 15A: Right gel panel, Lane 2 shows the wild type (WT) Fc protein (Fc), Lane 3, the EndoS2-cleaved protein (ES2), Lane 4, the azide-activated protein ($N_3$), Lane 5, the DIBO-Dye-488 labeled protein (Dye488), and Lanes 6 and 7 show the Tzn and TCO-activated forms, respectively. FIG. 15B: Azide-modified forms of trastuzumab (tra) and rituximab (rit) activated with TCO or Tzn are shown in Lanes 4-9. FIG. 15C: Conjugates of human IgG1-Fc protein with trastuzumab and rituximab are shown in Lanes 2-5. The TCO-Tzn pairs were mixed and matched producing the expected 75 kD protein conjugates shown (IgG HC/Fc Protein).

FIG. 16A: Azide-activated hIgG-Fc protein was activated with TCO-PEG-12-DBCO (TCO12), or Tzn-PEG12-DBCO (Tzn12) Tzn-PEG4-DBCO (Tzn4) and post-labeled with Dye-488-SE in a one-pot reaction. The proteins were separated by gel electrophoresis and images acquired as described in Example 4. The DOL of the final Dye-488 labeled Fc proteins was 5-7 dyes per Fc protein (average). The fluorescence image of the three labeled compounds is shown. The arrow indicates the Dye-488-labeled Fc Proteins. FIGS. 15B and 15C: The Dye-488 labeled TCO/Tzn-Fc proteins were mixed and matched with the corresponding NIST mAb TCO-Tzn pairs, and the resulting conjugates were resolved by reducing gel electrophoresis. The gel was imaged for Dye488 fluorescence (FIG. 16C) and then post-stained with SYPRO Ruby total protein stain (FIG. 16B). The expected 75 kD fluorescently-tagged NIST mAb conjugates are indicated by the arrows. The fluorescent NIST mAb-Fc conjugates show marked quenching of the SYPRO Ruby staining in comparison to the non-labeled species (no-Dye Fc), a result of strong Dye-488 labeling. There was little difference between the PEG12 or PEG4 species in conjugation efficiency, and there did not seem to be a preference for TCO or Tzn for either of the proteins.

DETAILED DESCRIPTION OF THE INVENTION

Figure 1:
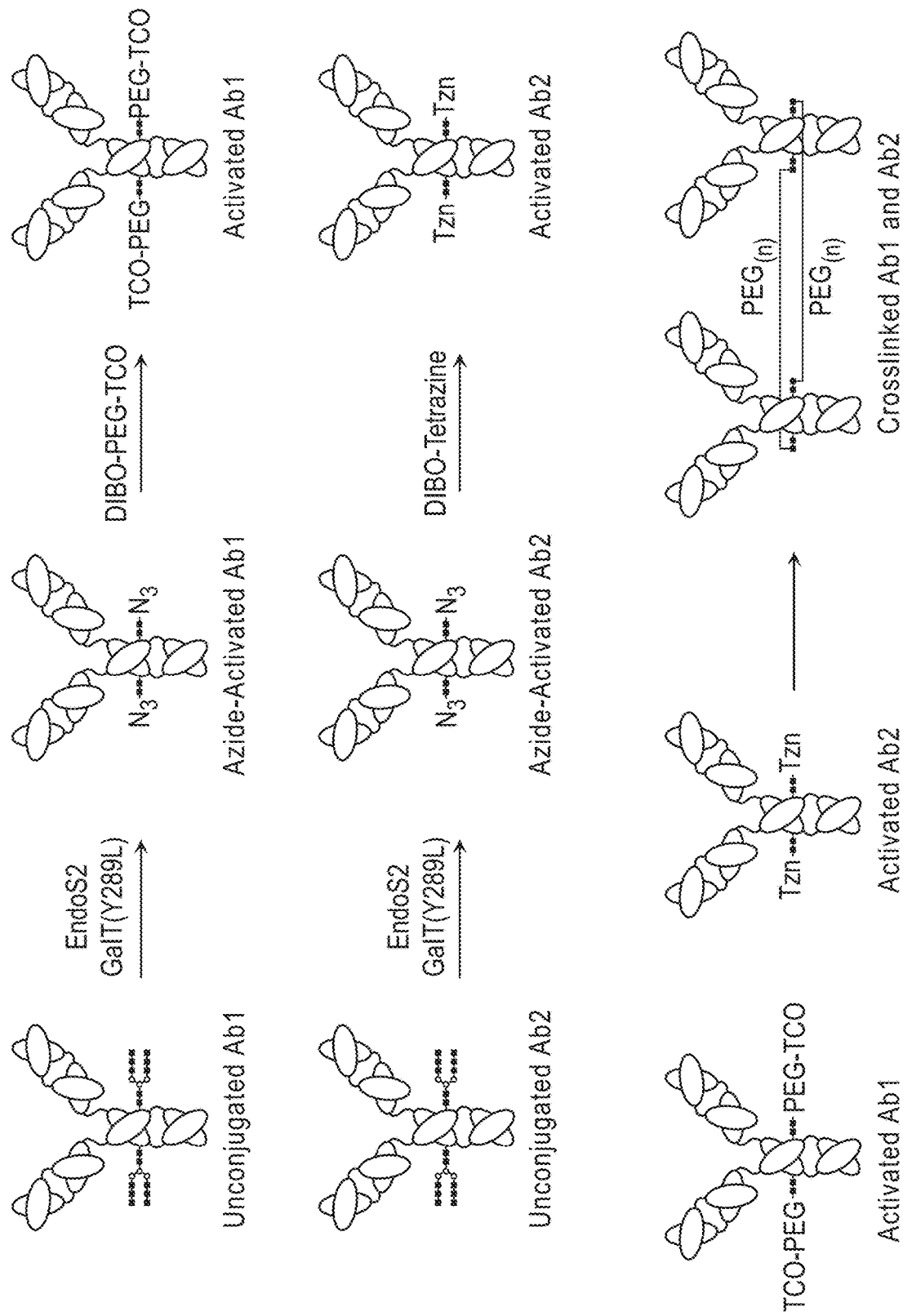
FIG. 1: Schematic of a strategy for making site-specific, directional bispecific antibodies according to certain embodiments of the present disclosure. In this schematic, the first antibody (Unconjugated Ab1) is incubated with endoglycosidase S2 (Endo S2) to provide terminal GlcNAc residues and a Y289L mutant of galactosyl transferase (GalT(Y289L)) to catalyze the attachment of GalNAz to the terminal GlcNAc residue to provide a first modified antibody (Azide-Activated Ab1). The first modified antibody is then incubated with a first activating molecule (DIBO-PEG-TCO) that comprises a first crosslinking group (a transcyclooctene (TCO)) and a first reactive group (a dibenzocyclooctyne or DIBO) and a linker comprising polyethylene glycol (PEG, n=0-300) to provide a first activated antibody (Activated Ab1). The second antibody (Unconjugated Ab2) is incubated with endoglycosidase S2 to provide terminal GlcNAc residues and a Y289L mutant of galactosyl transferase (GalT(Y289L)) to catalyze the attachment of GalNAz to the terminal GlcNAc residue to provide a second modified antibody (Azide-Activated Ab2). The second modified antibody is then incubated with a second activating molecule (DIBO-Tetrazine) that comprises a second crosslinking group (a tetrazine (Tzn)), a second reactive group (a dibenzocyclooctyne (DIBO)) and optionally a linker comprising polyethylene glycol (PEG, n=0-300) to provide a second activated antibody (Activated Ab2). The first activated antibody (Activated Ab1) and the second activated antibody (Activated Ab2) are incubated together wherein the first crosslinking group of the first activated antibody reacts with the second crosslinking group of the second activated antibody, thereby forming a bispecific antibody (Crosslinked Ab1 and Ab2).

Monoclonal antibodies are widely used for the treatment of diseases such as cancer, infectious diseases, inflammatory diseases and a variety of other disorders. Most of the marketed antibodies are monospecific and therefore interact with a single target or antigen. However, many diseases, such as cancer, are multifactorial and may involve several different signaling pathways and receptors. Consequently, the ability to block or interfere with more than one target or antigen would be beneficial.

Bispecific antibodies may bind to two or more different antigens or targets. Bispecific antibodies are produced by a number of different recombinant strategies that are well-known in the art and include genetic engineering of the antibodies. Such strategies include single chain variable fragment (scFv)-derived formats such as diabodies, tandem diabodies, BiTes (bispecific T-cell engager) and DARTs (Dual Affinity Re-Targeting), as well as immunoglobulin G (IgG)-based formats such as Triomab, DVD-Ig (Dual Variable Domain antibodies) and two-in-one antibodies. The production of products using these methods can be time consuming and costly, especially for upstream screening of multiple compatible antibody pairs. In addition, a number of chemical approaches have been developed which primarily exploit the reactivity of lysine or cysteine residues within the antibody. Drawbacks of these approaches include the production of highly cross-linked unwanted species, difficult and/or time-consuming characterization and purification of the desired products, and the lack of site-specificity of the conjugation sites which can impair or destroy antibody binding affinities.

It is well known that some of the problems with small single chain scFv antibodies and other small variants, such as bispecific diabodies and BiTEs, include having less avidity to their antigens than whole IgGs, being less stable, having shorter serum half-lives, and being highly immunogenic. As such, it is desirable for bispecific antibodies to have a structure that is as close to native IgGs as is possible. The methods provided herein for making bispecific antibodies and antibody conjugates do not require genetic engineering and allow for the directional, site-specific crosslinking of two or more antibodies, antibody fragments comprising a terminal GlcNAc residue, and/or Fc-fusion proteins and provide full antigen binding avidity towards two or more different antigens. Other existing antibody crosslinking chemistries that are known in the art cannot be used to perform this crosslinking at least because 1) the lack of site-specificity, 2) labeling of random sites, and 3) having a variable number of labeling sites which result in the formation of highly complex multivalent mixtures of antibodies that are difficult to characterize. These shortcomings result in bispecific antibodies that are of low yield and are difficult to purify. The methods provided herein overcome these difficulties because of the site-specific and directional cross-linking, which ensures maintenance of antibody binding activity. In addition, the methods provided herein limit the degree of labeling (DOL) thereby minimizing the amount of undesirable, multiply-crosslinked, multivalent species which allows for increased yields and easier purification of the desired bispecific antibodies. Additionally, the methods provided herein do not require genetic engineering of the antibodies and instead can use any existing antibody that contains glycan residues, for example, on the Fc protein region, which allows for more versatility in multiplexed screening studies when searching for the most effective antibody pairs. As such, efforts can be rapidly focused on screening for optimal crosslinker bioorthogonal pairs.

In certain embodiments, the methods involve the crosslinking of one, two, three, four, or more, preferably two, antibodies, antibody fragments comprising a terminal GlcNAc residue, and/or Fc-fusion proteins to form a bispecific antibody pair or antibody conjugate. The first step imparts site-specificity, wherein a first antibody, antibody fragment comprising a terminal GlcNAc residue, and/or Fc-fusion protein is each activated with a chemical handle on heavy chain Fc domain GlcNAc residues using an enzyme-mediated method using a glycosyl transferase GalT (Y289L) mutant enzyme. Then, the first antibody, antibody fragment, or Fc-fusion protein is reacted with a first activating molecule that comprises i) a first reactive group that reacts with the chemical handle and ii) a first crosslinking group. A second antibody, antibody fragment, or Fc-fusion protein is reacted with a second activating molecule that comprises i) a second reactive group that reacts with the chemical handle and ii) a second crosslinking group. The addition of the crosslinking groups imparts directionality to the reaction, namely, the crosslinking group on the first antibody can only react with the crosslinking group on the second antibody. The first and second crosslinking groups cannot react with themselves. After activation, the first and second antibodies, antibody fragments, and/or Fc-fusion proteins are purified and reacted together whereby the crosslinking group of the first antibody, antibody fragment and/or Fc-fusion protein reacts only with the crosslinking group of the second antibody, antibody fragment and/or Fc-fusion protein in a Diels-Alder reaction. The crosslinked antibodies are then purified away from unreacted single antibodies. In certain embodiments, the antibody fragment is an Fc protein. In certain embodiments, the Fc protein is an Fc protein scaffold and the antibody conjugate is an antibody-Fc protein scaffold conjugate.

In certain embodiments, the first antibody, antibody fragment, or Fc-fusion protein and the second antibody, antibody fragment or Fc-fusion protein contain a single crosslink. In certain embodiments, the first antibody, antibody fragment or Fc-fusion protein and the second antibody, antibody fragment or Fc-fusion protein contain two crosslinks.

In certain embodiments, the terminal GlcNAc residue on the first antibody, first antibody fragment or first Fc-fusion protein and/or second antibody, second antibody fragment or second Fc-fusion protein is attached to an asparagine. In certain embodiments, the asparagine is located on the Fc region of an antibody or antibody fragment. In certain embodiments, the asparagine on the Fc region is at amino acid position 287 (Asn287).

In certain embodiments, the bispecific antibodies or antibody conjugates are at least 50% pure. In certain embodiments, the bispecific antibodies or antibody conjugates are at least 60% pure. In certain embodiments, the bispecific antibodies or antibody conjugates are at least 70% pure. In certain embodiments, the bispecific antibodies or antibody conjugates are at least 80% pure. In certain embodiments, the bispecific antibodies or antibody conjugates are at least 90% pure. In certain embodiments, the bispecific antibodies or antibody conjugates are at least 91%, at least 92%, at least 93%, at least 94% or at least 95% pure. In certain embodiments, the purity of the bispecific antibodies or antibody conjugates is compared to multiply crosslinked higher molecular weight antibody or antibody conjugate species.

The methods of the present disclosure provide rapid and efficient methods for the site-specific, directional, crosslinking of essentially any two existing antibodies yielding the desired tetravalent bispecific species. The site-specific methods provided herein preserve antigen binding affinity and ensures the directionality of conjugation. In certain embodiments, the first and second antibody, antibody fragment or Fc-fusion protein are treated with an endoglycosidase, preferably endoglycosidase S2 (EndoS2), to cleave the Fc domain glycan leaving a single core GlcNAc residue (e.g., a terminal GlcNAc residue) at the core antibody glycosylation sites. The core GlcNAc residues are modified with a chemical handle, preferably an azide moiety, after treatment with a mutant GalT (Y289L) enzyme that efficiently transfers a galactose-azide sugar onto the terminal GlcNAc residues. This step imparts site-selectivity to the crosslinking process. Next, each of the modified antibodies is activated with one of two Diels Alder orthogonal reactive-pair functional groups: transcyclooctyne (TCO) or methyltetrazine (Tzn). This step imparts directionality to the antibody crosslinking process preventing the formation of highly cross-linked and unwanted high molecular weight species. Once the antibodies are activated, the TCO/Tzn antibody pairs are mixed and matched in equal molar amounts to yield site-specific, directionally conjugated, tetrameric bispecific pairs.

Although the treatment with endoglycosidase should result in two available sites for conjugating the modified sugar and subsequent crosslinking, it was unexpectedly discovered that only a single site is utilized in the crosslinking reaction and there is no "daisy-chaining" of activated antibodies. This unexpected discovery results in only two (2) antibodies being crosslinked which results in a very high yield of the desired bispecific antibody. In addition, as shown in the Examples section herein below, mass spectroscopic and enzymatic analyses of the labeled antibodies confirmed the site-specific crosslinking sites were limited to the antibody Fc domain glycosylation sites (see, FIG. 10). Gel analyses demonstrated a high yield of the desired tetravalent bispecific species (greater than 80% yield without purification) that can then be further screened for binding and physiological efficacy. Furthermore, the results also demonstrate the production of a NIST mAb site-specifically crosslinked to an IgG1 Fc protein that can be used as a scaffold for site-specific payload attachment (see FIGS. 14 and 15A-C).

Definitions

The section headings used herein are for organizational purposes only and are not to be construed as limiting the desired subject matter in any way. All literature cited in the specification, including but not limited to, patents, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Before describing the present teachings in detail, it is to be understood that this disclosure is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "an antibody" includes a plurality of antibodies and the like.

Certain compounds disclosed herein can exist in unsolvated forms as well as solvated forms, including hydrated forms. In general, the solvated forms are equivalent to unsolvated forms and are encompassed within the scope of the present teachings.

Certain compounds disclosed herein may exist in multiple crystalline or amorphous forms. In general, all physical forms are equivalent for the uses contemplated by the present disclosure and are intended to be within the scope of the present teachings.

Certain compounds disclosed herein possess asymmetric carbon atoms (optical centers) or double bonds; the racemates, diastereomers, geometric isomers and individual isomers are encompassed within the scope of the present teachings.

The compounds described herein may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, Acc. Chem. Res. 23: 128 (1990).

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), carbon-14 ($^{14}$C), $^{45}$Ti, $^{51}$Mn, $^{52}$Mn, $^{52m}$Mn, $^{52}$Fe, $^{60}$Cu, $^{61}$Cu, $^{64}$Cu, $^{67}$Cu, $^{67}$Ga, $^{68}$Ga, $^{72}$As, $^{89}$Y, $^{89}$Zr, $^{94m}$Tc, $^{99m}$Tc, $^{110}$In, $^{111}$In, $^{113}$In, or $^{177}$Lu. All isotopic variations of the compounds disclosed herein, whether radioactive or not, are intended to be encompassed within the scope of the present teachings.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

Selected compounds having a formal electronic charge may be shown without an appropriate biologically compatible counterion. Such a counterion serves to balance the positive or negative charge present on the compound. As used herein, a substance that is biologically compatible is not toxic as used, and does not have a substantially deleterious effect on biomolecules. Examples of negatively charged counterions include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred counterions may include chloride, iodide, perchlorate and various sulfonates. Examples of positively charged counterions include, among others, alkali metal, or alkaline earth metal ions, ammonium, or alkylammonium ions.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

Unless defined otherwise, all technical and scientific terms used herein have the same meaning as commonly understood by one of ordinary skill in the art to which this invention is related. The following terms are defined for purposes of the present disclosure.

TABLE 1

List of Abbreviations

| Abbreviation | Term |
| --- | --- |
| Gal | Galactose |
| GalNAz | N-alpha-azidoacetylgalactosamine |
| GlcNAz | N-alpha-azidoacetylglucosamine |
| GalNAc | N-acetylgalactosamine |
| GlcNAc | N-acetylglucosamine |
| NeuAc | N-acetylneuraminic acid |
| GalKyne | Alkyne-modified galactosamine |
| GalKetone | Ketone-modified galactosamine |
| Gal-Cyclopropene | Cyclopropene-modified galactosamine |
| Gal-Oxime | Oxime-modified galactosamine |
| Gal-Nitrile oxide | Nitrile oxide-modified galactosamine |

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. C$_1$-C$_6$ means one to six carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present teachings contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P, S, and Se and wherein the nitrogen, phosphorous, sulfur, and selenium atoms are optionally oxidized, and the nitrogen heteroatom is optionally quaternized. The heteroatom(s) O, N, P, S, Si, and Se may be placed at any interior position of the heteroalkyl group or at the position at which the alkyl group is attached to the remainder of the molecule. Examples include, but are not limited to, —$CH_2CH_2OCH_3$, —$CH_2CH_2NHCH_3$, —$CH_2CH_2N(CH_3)CH_3$, —$CH_2SCH_2CH_3$, —$CH_2CH_2S(O)CH_3$, —$CH_2CH_2S(O)_2CH_3$, —CH═$CHOCH_3$, —$Si(CH_3)_3$, —$CH_2CH$═$NOCH_3$, and —CH═$CHN(CH_3)CH_3$. Up to two heteroatoms may be consecutive, such as, for example, —$CH_2NHOCH_3$ and —$CH_2OSi(CH_3)_3$. Similarly, the term "heteroalkylene" by itself or as part of another substituent means a divalent radical derived from heteroalkyl, as exemplified, but not limited by, —$CH_2CH_2SCH_2CH_2$— and —$CH_2SCH_2CH_2NHCH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2$R'— represents both —$C(O)_2$R'— and —R'$C(O)_2$—.

Each of the above terms (e.g., "alkyl" and "heteroalkyl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', ═O, ═NR', ═NOR', —NR'R", —SR', -halogen, —SiR'R"R'", —OC(O)R', —C(O)R', —$CO_2$R', —CONR'R", —OC(O)NR'R", —NR"C(O)R', —NR'C(O)NR"R'", —NR"C(O)$_2$R', —NR—C(NR'R"R'") ═NR"", —NRC(NR'R")═NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As used herein, the term "heteroatom" includes oxygen (O), nitrogen (N), sulfur (S), phosphorus (P), silicon (Si), and selenium (Se).

The term "amino" or "amine group" refers to the group —NR'R" (or N$^+$RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The term "activated alkyne," as used herein, refers to a chemical moiety that selectively reacts with an azide reactive group on another molecule to form a covalent chemical bond between the activated alkyne group and the alkyne reactive group. Activated alkynes include, but are not limited to the cyclooctynes and difluorocyclooctynes described by Agard et al., *J. Am. Chem. Soc.*, 126(46):15046-15047 (2004); the dibenzocyclooctynes described by Boons et al., PCT Publication No. WO 2009/067663 A1 (2009); and the aza-dibenzocyclooctynes described by Debets et al., *Chem. Comm.*, 46:97-99 (2010). These dibenzocyclooctynes (including the aza-dibenzocyclooctynes) described above are collectively referred to herein as cyclooctyne groups. Activated alkynes also include cyclononynes described by Dommerholt et al., *Angew. Chem.* 122:9612-9615 (2010)).

The term "affinity," as used herein, refers to the strength of the binding interaction of two molecules, such as an antibody and an antigen or a positively charged moiety and a negatively charged moiety. For bivalent molecules such as antibodies, affinity is typically defined as the binding strength of one binding domain for the antigen, e.g. one Fab fragment for the antigen. The binding strength of both binding domains together for the antigen is referred to as "avidity". As used herein "high affinity" refers to a ligand that binds to an antibody having an affinity constant ($K_a$) greater than $10^4$ M$^{-1}$, typically $10^5$-$10^{11}$ M$^{-1}$; as determined by inhibition ELISA or an equivalent affinity determined by comparable techniques such as, for example, Scatchard plots or using $K_d$/dissociation constant, which is the reciprocal of the $K_a$.

The term "alkyne reactive," as used herein, refers to a chemical moiety that selectively reacts with an alkyne modified group on another molecule to form a covalent chemical bond between the alkyne modified group and the alkyne reactive group. Examples of alkyne-reactive groups include, but are not limited to, azides. "Alkyne-reactive" can also refer to a molecule that contains a chemical moiety that selectively reacts with an alkyne group.

The term "antibody" as used herein refers to an immunoglobulin molecule or immunologically active portion thereof, i.e., an antigen-binding portion. Examples of immunologically active portions of immunoglobulin molecules include immunoglobulin molecules or fragments thereof that comprise the F(ab) region and a sufficient portion of the Fc region to comprise the oligosaccharide linkage site, for example, the asparagine-GlcNAc linkage site (e.g., Asn 287). An antibody may be a polyclonal, monoclonal, recombinant (e.g., a chimeric or humanized), fully human, non-human (e.g., murine), or a single chain antibody. An antibody may have effector function and may fix complement, and may be coupled to a toxin or imaging agent. Antibodies may be endogenous or polyclonal wherein an animal is immunized to elicit a polyclonal antibody response or by recombinant methods resulting in monoclonal antibodies produced from hybridoma cells or other cell lines. It is understood that the term "antibody" as used herein includes within its scope any of the various classes or sub-classes of immunoglobulin derived from any of the animals conventionally used. An antibody may be, for example, an IgA, an IgD, an IgE, an IgG, an IgM, or an IgY.

The term "antibody fragments," as used herein, refers to fragments of antibodies that retain the principal selective binding characteristics of the whole antibody, for example, a sufficient portion of the Fc region to comprise the oligosaccharide linkage site, for example, the asparagine-GlcNAc linkage site.

Antibody fragments include Fc proteins, including but not limited to, Fc protein scaffolds.

The term "antigen," as used herein, refers to a molecule that induces, or is capable of inducing, the formation of an antibody or to which an antibody binds selectively, including but not limited to a biological material. Antigen also refers to "immunogen". The target-binding antibodies selectively bind an antigen; as such the term can be used herein interchangeably with the term "target".

The term "aqueous solution," as used herein, refers to a solution that is predominantly water and retains the solution characteristics of water. Where the aqueous solution contains solvents in addition to water, water is typically the predominant solvent.

The term "azide reactive," as used herein, refers to a chemical moiety that selectively reacts with an azido modified group on another molecule to form a covalent chemical bond between the azido modified group and the azide reactive group. Examples of azide-reactive groups include, but are not limited to, phosphines, including, but not limited to, triarylphosphines, alkynes, including but not limited to terminal alkynes, cyclononynes, cyclooctynes and difluorocyclooctynes as described by Agard et al., *J. Am. Chem. Soc.*, 126 (46):15046-15047 (2004), dibenzocyclooctynes as described by Boons et al., PCT Publication No. WO 2009/067663 A1 (2009), and aza-dibenzocyclooctynes as described by Debets et al., *Chem. Comm.*, 46:97-99 (2010). The various difluorocyclooctynes and dibenzocyclooctynes described above are collectively referred to herein as cyclooctyne groups. "Azide-reactive" can also refer to a molecule that contains a chemical moiety that selectively reacts with an azido group.

The term "buffer," as used herein, refers to a system that acts to minimize the change in acidity or basicity of the solution against addition or depletion of chemical substances.

The term, "chemical handle" as used herein refers to a specific functional group, such as an azide; an alkyne, including, but not limited to, a terminal alkyne, an activated alkyne, a cyclooctyne, and a cyclononyne, a phosphite, a phosphine, including, but not limited to a triarylphosphine, an oxime, a nitrile oxide and the like. A chemical handle is a moiety that is rarely found in naturally-occurring biomolecules and is chemically inert towards biomolecules (e.g., native cellular components), but when reacted with an azide-reactive or alkyne-reactive group the reaction can take place efficiently under biologically relevant conditions (e.g., cell culture conditions, such as in the absence of excess heat or harsh reactants). Chemical handles also include a Diels-Alder diene, a Diels-Alder dienophile, ketones, a straight or branched $C_1$-$C_{12}$ carbon chain bearing a carbonyl group, —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), or —$ONH_2$ (aminooxy), wherein each $R^1$, $R^2$, and $R^3$ is independently H or alkyl having 1-6 carbons.

The term "click chemistry," as used herein, refers to the Huisgen cycloaddition or the 1,3-dipolar cycloaddition between an azide and an alkyne to form a 1,2,4-triazole. Such chemical reactions can use, but are not limited to, simple heteroatomic organic reactants and are reliable, selective, stereospecific, and exothermic.

The term "cycloaddition" as used herein refers to a chemical reaction in which two or more π (pi)-electron systems (e.g., unsaturated molecules or unsaturated parts of the same molecule) combine to form a cyclic product in which there is a net reduction of the bond multiplicity. In a cycloaddition reaction, the π (pi) electrons are used to form new π (pi) bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 1,3-dipolar cycloadditions, occur between a 1,3-dipole and a dipolarophile and are typically used for the construction of five-membered heterocyclic rings. The term "[3+2] cycloaddition" also encompasses "copperless" [3+2] cycloadditions between azides and cyclooctynes and difluorocyclooctynes described by Agard et al., *J. Am. Chem. Soc.*, 126 (46):15046-15047 (2004), the dibenzocyclooctynes described by Boon et al., PCT Publication No. WO 2009/067663 A1 (2009), and the aza-dibenzocyclooctynes described by Debets et al., *Chem. Comm.*, 46:97-99 (2010).

The term "detectable response" as used herein refers to an occurrence of, or a change in, a signal that is directly or indirectly detectable either by observation or by instrumentation. The detectable response may be an occurrence of a signal wherein a fluorophore is inherently fluorescent and does not produce a change in signal upon binding to a metal ion or biological compound. Alternatively, the detectable response is an optical response resulting in a change in the wavelength distribution patterns or intensity of absorbance or fluorescence or a change in light scatter, fluorescence lifetime, fluorescence polarization, or a combination of the above parameters. Other detectable responses include, for example, chemiluminescence, phosphorescence, radiation from radioisotopes, magnetic attraction and electron density.

The term "detectably distinct" as used herein refers to a signal that is distinguishable or separable by a physical property either by observation or by instrumentation. For example, a fluorophore is readily distinguishable either by spectral characteristics or by fluorescence intensity, lifetime, polarization or photo-bleaching rate from another fluorophore in the sample, as well as from additional materials that are optionally present.

The term "directly detectable" as used herein refers to the presence of a material or the signal generated from the material is immediately detectable by observation, instrumentation, or film without requiring chemical modifications or additional substances.

Figure 14:
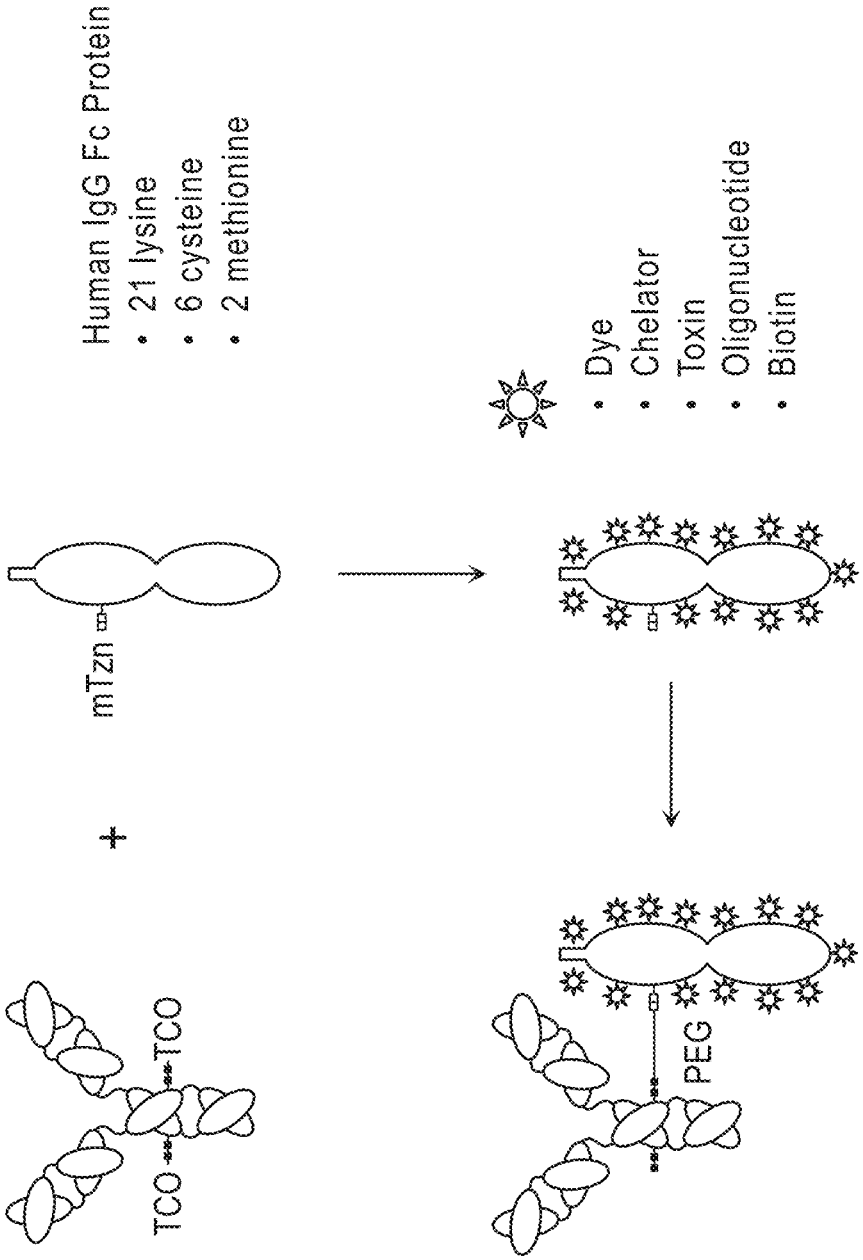
FIG. 14: Schematic of a strategy for making an antibody conjugate according to certain embodiments of the present disclosure. In this schematic, a trans-cyclooctene (TCO) activated antibody (TCO-activated antibody) is crosslinked to a methyltetrazine (mTzn) activated antibody fragment, specifically an activated Fc protein scaffold (mTzn-PEG-activated human IgG Fc protein). The stars denote compounds and/or labels that are conjugated to the Fc protein. The compounds can be, for example, dyes, chelators, toxins, oligonucleotides, or biotin, and can be attached to the Fc protein at one or more lysine, cysteine and/or methionine residues of the Fc protein.

The term "Fc protein scaffold" as used herein refers to an antibody fragment, specifically an Fc protein, for example an IgG Fc protein, that comprises one or more compounds, including but not limited to dyes, fluorophores, chelators, toxins, oligonucleotides, and biotin, conjugated to one or more lysine, cysteine and/or methionine residues in the Fc protein (See, FIG. 14).

The term "fluorophore" as used herein refers to a composition that is inherently fluorescent or demonstrates a change in fluorescence upon binding to a biological compound or metal ion, i.e., fluorogenic. Fluorophores may contain substituents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluorescein, rhodamine and rhodol as well as other fluorophores described in Haugland, R., *Molecular Probes Handbook of Fluorescent Probes and Research Chemicals* (10$^{th}$ edition, CD-ROM, September 2005), which is herein incorporated by reference in its entirety.

The term "glycoprotein," as used herein, refers to a protein that has been glycosylated and those that have been enzymatically modified, in vivo or in vitro, to comprise a sugar group. Glycoproteins may also include modified sugar groups. Glycoproteins include, but are not limited to, antibodies, antibody fragments, Fc antibody fragments and Fc fusion proteins.

The term "kit," as used herein, refers to a packaged set of related components, typically one or more compounds or compositions.

The term "label," as used herein, refers to a chemical moiety or protein that is directly or indirectly detectable (e.g. due to its spectral properties, conformation or activity) when attached to a target or compound, including reporter molecules, solid supports and carrier molecules, and used in the present methods. The label can be directly detectable (e.g., fluorophore or radiolabel) or indirectly detectable (e.g., hapten or enzyme). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The term label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidase (HRP) to bind to the tag, and then use a colorimetric substrate (e.g., tetramethylbenzidine (TMB)) or a fluorogenic substrate such as Amplex Red reagent (Thermo Fisher Scientific, Waltham, MA) to detect the presence of HRP. Numerous labels are known by those of skill in the art and include, but are not limited to, particles, fluorophores, and other labels that are described in Haugland, R., *Molecular Probes Handbook of Fluorescent Probes and Research Chemicals* (10$^{th}$ edition, CD-ROM, September 2005), supra.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

The term "phosphine reactive" as used herein refers to a chemical moiety that selectively reacts via Staudinger ligation with a phosphine group, including but not limited to a triarylphosphine group, on another molecule to form a covalent chemical bond between the triarylphosphine group and the phosphine reactive group. Examples of phosphine reactive groups include, but are not limited to, an azido group.

The terms "protein" and "polypeptide" are used herein in a generic sense to include polymers of amino acid residues of any length. The term "peptide" is used herein to refer to polypeptides having less than 100 amino acid residues, typically less than 10 amino acid residues. The terms apply to amino acid polymers in which one or more amino acid residues are an artificial chemical analogue of a corresponding naturally occurring amino acid, as well as to naturally occurring amino acid polymers.

The term "purified" as used herein refers to a preparation of a protein that is essentially free from contaminating proteins that normally would be present in association with the protein, e.g., in a cellular mixture or milieu in which the protein or complex is found endogenously such as serum proteins or cellular lysate.

The term "sample" as used herein refers to any material that may contain an analyte or cell-associated antigen for detection or quantification. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, oligonucleotides, peptides and buffer solutions. The sample may also be a lysate isolated from a cell. The sample may be in an aqueous solution, a viable cell culture or immobilized on a solid or semi-solid surface such as a polyacrylamide gel, membrane blot or on a microarray. The sample may also be a subject, such as a mammal.

The term "Staudinger ligation" as used herein refers to a chemical reaction developed by Saxon and Bertozzi (E. Saxon and C. Bertozzi, *Science*, 287: 2007-2010 (2000)) that is a modification of the classical Staudinger reaction. The classical Staudinger reaction is a chemical reaction in which the combination of an azide with a phosphine or phosphite produces an aza-ylide intermediate, which upon hydrolysis yields a phosphine oxide and an amine. A Staudinger reaction is a mild method of reducing an azide to an amine; and triphenylphosphine is commonly used as the reducing agent. In a Staudinger ligation, an electrophilic trap (usually a methyl ester) is appropriately placed on the aryl group of a triarylphosphine (usually ortho to the phosphorus atom) and reacted with the azide, to yield an aza-ylide intermediate, which rearranges in aqueous media to produce a compound with amide group and a phosphine oxide function. The Staudinger ligation is so named because it ligates (attaches/covalently links) the two starting molecules together, whereas in the classical Staudinger reaction, the two products are not covalently linked after hydrolysis.

In general, for ease of understanding the present disclosure the methods for site-specific crosslinking of antibodies, antibody fragments and/or Fc-fusion proteins to create bispecific antibodies will first be described in detail, followed by some embodiments in which such bispecific antibodies may be used. In addition, embodiments in which methods are provided for site-specific conjugation of antibodies to Fc protein scaffolds, liposomes or capped mRNA will be discussed followed by embodiments in which such conjugated antibodies may be used.

"Click" Chemistry

Azides and terminal or internal alkynes can undergo a 1,3-dipolar cycloaddition (Huisgen cycloaddition) reaction to give a 1,2,3-triazole. However, this reaction requires long reaction times and elevated temperatures. Alternatively, azides and terminal alkynes can undergo Copper(I)-catalyzed Azide-Alkyne Cycloaddition (CuAAC) at room temperature. Such copper(I)-catalyzed azide-alkyne cycloadditions, also known as "click" chemistry, is a variant of the Huisgen 1,3-dipolar cycloaddition wherein organic azides and terminal alkynes react to give 1,4-regioisomers of 1,2,3-triazoles. Examples of "click" chemistry reactions are described by Sharpless et al. (U.S. Patent Application Publication No. 2005/0222427, published Oct. 6, 2005, International Application No. PCT/US03/17311; Lewis W G, et al., *Angew. Chem. Int. Ed.* 41 (6): 1053; method reviewed in Kolb, H. C., et al., *Angew. Chem. Int. Ed.* 40:2004-2021 (2001)), which developed reagents that react with each other in high yield and with few side reactions in a heteroatom linkage (as opposed to carbon-carbon bonds) in order to create libraries of chemical compounds.

The copper used as a catalyst for the "click" chemistry reaction to conjugate a label to a modified glycoprotein is in the Cu(I) reduction state. The sources of copper(I) used in such copper(I)-catalyzed azide-alkyne cycloadditions can be any cuprous salt including, but not limited to, cuprous halides such as cuprous bromide or cuprous iodide. However, this regioselective cycloaddition can also be conducted in the presence of a metal catalyst and a reducing agent. Copper can be provided in the Cu(II) reduction state (for example, as a salt, such as but not limited to $Cu(NO_3)_2$, $Cu(OAc)_2$ or $CuSO_4$), in the presence of a reducing agent wherein Cu(I) is formed in situ by the reduction of Cu(II). Such reducing agents include, but are not limited to, ascorbate, tris(2-carboxyethyl) phosphine (TCEP), NADH, NADPH, thiosulfate, metallic copper, hydroquinone, vitamin $K_1$, glutathione, cysteine, 2-mercaptoethanol, dithiothreitol, $Fe^{2+}$, $Co^{2+}$, or an applied electric potential. The reducing agents may also include metals selected from Al, Be, Co, Cr, Fe, Mg, Mn, Ni, Zn, Au, Ag, Hg, Cd, Zr, Ru, Fe, Co, Pt, Pd, Ni, Rh, and W.

Without limitation to any particular mechanism, copper in the Cu(I) state is a preferred catalyst for the copper(I)-catalyzed azide-alkyne cycloadditions, or "click" chemistry reactions. Certain metal ions, such as Cu(I), are unstable in aqueous solvents, therefore stabilizing ligands/chelators can be used to improve the reaction. Typically, at least one copper chelator is used, wherein such chelators bind copper in the Cu(I) state. Alternatively, at least one copper chelator is used, wherein such chelators bind copper in the Cu(II) state. In some instances, the copper(I) chelator is a 1,10 phenanthroline-containing copper (I) chelator. Non-limiting examples of such phenanthroline-containing copper (I) chelators include, but are not limited to, bathophenanthroline disulfonic acid (4,7-diphenyl-1,10-phenanthroline disulfonic acid) and bathocuproine disulfonic acid (BCS; 2,9-dimethyl-4,7-diphenyl-1,10-phenanthroline disulfonate). In other embodiments, the copper(I) chelator is THPTA as described in Jentzsch et al., *Inorganic Chemistry*, 48(2): 9593-9595 (2009), or the copper(I) chelators are those described in Finn et al., U.S. Patent Publication No. 2010/0197871. Other chelators used in such methods include, but are not limited to, N-(2-acetamido)iminodiacetic acid (ADA), pyridine-2,6-dicarboxylic acid (PDA), S-carboxymethyl-L-cysteine (SCMC), trientine, tetra-ethylenepolyamine (TEPA), N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), tris-(benzyl-triazolylmethyl)amine (TBTA), or a derivative thereof. Most metal chelators, a wide variety of which are known in the chemical, biochemical, and medical arts, are known to chelate several metals, and thus metal chelators in general can be tested for their function in 1,3-cycloaddition reactions catalyzed by copper. Histidine may be used as a chelator, while glutathione may be used as a chelator and a reducing agent.

One or more copper chelators may be added more than once to such "click" chemistry reactions. In instances in which more than one copper chelator is added to a reaction, two or more of the copper chelators can bind copper in the Cu(I) state or, one or more of the copper chelators can bind copper in the Cu(I) state and one or more additional chelators can bind copper in the Cu(II) state.

In certain embodiments of the methods described herein, the modified antibodies, antibody fragments and/or Fc-fusion proteins can comprise an azide moiety, whereupon the reactive group of the activating molecules can comprise a terminal alkyne moiety. In certain embodiments of the methods described herein, the modified antibodies, antibody fragments and/or Fc-fusion proteins can comprise a terminal alkyne moiety, whereupon the reactive group of the activating molecules can comprise an azide moiety.

Activated Alkyne ("Copperless") Chemistry

Azides and alkynes can undergo catalyst free [3+2] cycloaddition by a using the reaction of activated alkynes with azides. Such catalyst-free [3+2] cycloaddition can be used in the methods described herein to conjugate a label or an activating molecule to a modified glycoprotein. Alkynes can be activated by ring strain such as, by way of example only, eight-membered ring structures, or nine-membered, appending electron-withdrawing groups to such alkyne rings, or alkynes can be activated by the addition of a Lewis acid such as, by way of example only, Au(I) or Au(III). Alkynes activated by ring strain have been described, and has been referred to as "copperless" [3+2] cycloaddition. For example, the cyclooctynes and difluorocyclooctynes described by Agard et al., *J. Am. Chem. Soc.*, 126 (46): 15046-15047 (2004), the dibenzocyclooctynes described by Boons et al., PCT International Publication No. WO 2009/067663 A1 (2009), the aza-dibenzocyclooctynes described by Debets et al., *Chem. Comm.*, 46:97-99 (2010), and the cyclononynes described by Dommerholt et al., *Angew. Chem.* 122:9612-9615 (2010)).

In certain embodiments of the methods described herein, the modified antibodies, antibody fragments and/or Fc-fusion proteins can comprise an azide moiety, whereupon the reactive group of the activating molecules can comprise an activated alkyne moiety. In certain embodiments of the methods described herein, the modified antibodies, antibody fragments and/or Fc-fusion proteins can comprise an activated alkyne moiety, whereupon the reactive group of the activating molecules can comprise an azide moiety.

Staudinger Ligation

The Staudinger reaction, which involves reaction between trivalent phosphorous compounds and organic azides (Staudinger et al. *Helv. Chim. Acta* 2:635 (1919)), has been used for a multitude of applications. (Gololobov et al. *Tetrahedron* 37:437 (1980)); (Gololobov et al. *Tetrahedron* 48: 1353 (1992)). There are almost no restrictions on the nature of the two reactants. The Staudinger ligation is a modification of the Staudinger reaction in which an electrophilic trap (usually a methyl ester) is placed on a triaryl phosphine. In the Staudinger ligation, the aza-ylide intermediate rearranges, in aqueous media, to produce an amide linkage and the phosphine oxide, ligating the two molecules together, whereas in the Staudinger reaction the two products are not covalently linked after hydrolysis. Such ligations have been described in U.S. Patent Application No. 2006/0276658. In certain embodiments, the phosphine can have a neighboring acyl group such as an ester, thioester or N-acyl imidazole (i.e. a phosphinoester, phosphinothioester, phosphinoimidazole) to trap the aza-ylide intermediate and form a stable amide bond upon hydrolysis. In certain embodiments, the phosphine can be a di- or triarylphosphine to stabilize the phosphine. The phosphines used in the Staudinger ligation methods described herein to conjugate a label to a modified glycoprotein include, but are not limited to, cyclic or acyclic, halogenated, bisphosphorus, or even polymeric. Similarly, the azides can be alkyl, aryl, acyl or phosphoryl. In certain embodiments, such ligations are carried out under oxygen-free anhydrous conditions. The antibodies described herein may be modified using a Staudinger ligation.

In certain embodiments of the methods described herein, the modified antibodies, antibody fragments and/or Fc-fusion proteins can comprise an azide moiety, whereupon the reactive group of the activating molecules can comprise a phosphine moiety, including, but not limited to, a triarylphosphine moiety. In certain embodiments of the methods described herein, the modified antibodies, antibody fragments and/or Fc-fusion proteins can comprise a phosphine moiety, including, but not limited to, a triarylphosphine moiety, whereupon the reactive group of the activating molecules can comprise an azide moiety.

Methods of Site-Specifically Cross-Linking Antibodies:

Herein are provided methods, compositions and kits for use in the directional, site-specific crosslinking of one, two, three, four, or more, preferably two, antibodies, antibody fragments, and/or Fc-fusion proteins to form bispecific antibodies and/or antibody conjugates comprising a combination of enzyme-mediated incorporation of modified sugars comprising a chemical handle into the antibody, antibody fragment, and/or Fc-fusion protein and cycloaddition chemistry with an activating molecule comprising a crosslinking group and a reactive group, wherein the reactive group attaches to the chemical handle of the modified sugar. The activating molecule may comprise a linker that separates the crosslinking group from the reactive group. In certain embodiments, the antibody, antibody fragment and/or Fc-fusion protein comprises a terminal GlcNAc residue. In certain embodiments, the terminal GlcNAc residue may be obtained by incubating the antibody, antibody fragment, and/or Fc-fusion protein with an enzyme such as an endoglycosidase or a β-galactosidase. In certain embodiments, the antibody is an IgA, an IgE, an IgD, an IgG, an IgM, or an IgY. In certain embodiments, the terminal GlcNAc residues are present on the Fc region of the antibody. In certain embodiments, the antibody fragment is an Fc protein. In certain embodiments, the Fc protein is an Fc protein scaffold and the antibody conjugate is an antibody-Fc protein scaffold conjugate.

In certain embodiments, the first antibody, antibody fragment, or Fc-fusion protein and the second antibody, antibody fragment or Fc-fusion protein contain a single crosslink. In certain embodiments, the first antibody, antibody fragment or Fc-fusion protein and the second antibody, antibody fragment or Fc-fusion protein contain two crosslinks.

In certain embodiments, the terminal GlcNAc residue on the first antibody, antibody fragment or Fc-fusion protein and/or second antibody, antibody fragment or Fc-fusion protein is attached to an asparagine. In certain embodiments, the asparagine is located on the Fc region of an antibody or antibody fragment. In certain embodiments, the asparagine on the Fc region is at amino acid position 287 (Asn287).

FIG. 1 depicts a strategy for making site-specific bispecific antibodies according to certain embodiments of the present disclosure. In this schematic, the first antibody (Unconjugated Ab1) is incubated with endoglycosidase S2 to provide terminal GlcNAc residues and a Y289L mutant of galactosyl transferase (GalT(Y289L)) to catalyze the attachment of GalNAz to the terminal GlcNAc residue to provide a first modified antibody (Azide-Activated Ab1). The first modified antibody is then incubated with a first activating molecule (DIBO-PEG-TCO) that comprises a first crosslinking group (a trans-cyclooctene (TCO)) and a first reactive group (a dibenzocyclooctyne (DIBO)) and a linker comprising polyethylene glycol (PEG, n=0-300) to provide a first activated antibody (Activated Ab1). The second antibody (Unconjugated Ab2) is incubated with endoglycosidase S2 to provide terminal GlcNAc residues and a Y289L mutant of galactosyl transferase (GalT(Y289L)) to catalyze the attachment of GalNAz to the terminal GlcNAc residue to provide a second modified antibody (Azide-Activated Ab2). The second modified antibody is then incubated with a second activating molecule (DIBO-Tetrazine) that comprises a second crosslinking group (a tetrazine (Tzn)), a second reactive group (a dibenzocyclooctyne (DIBO)) and optionally a linker comprising polyethylene glycol (PEG, n=0-300) to provide a second activated antibody (Activated Ab2). The first activated antibody (Activated Ab1) and the second activated antibody (Activated Ab2) are incubated together wherein the first crosslinking group of the first activated antibody reacts with the second crosslinking group of the second activated antibody, thereby forming a bispecific antibody (Crosslinked Ab1 and Ab2). The reaction of the TCO group with the Tzn group occurs rapidly.

Figure 2:
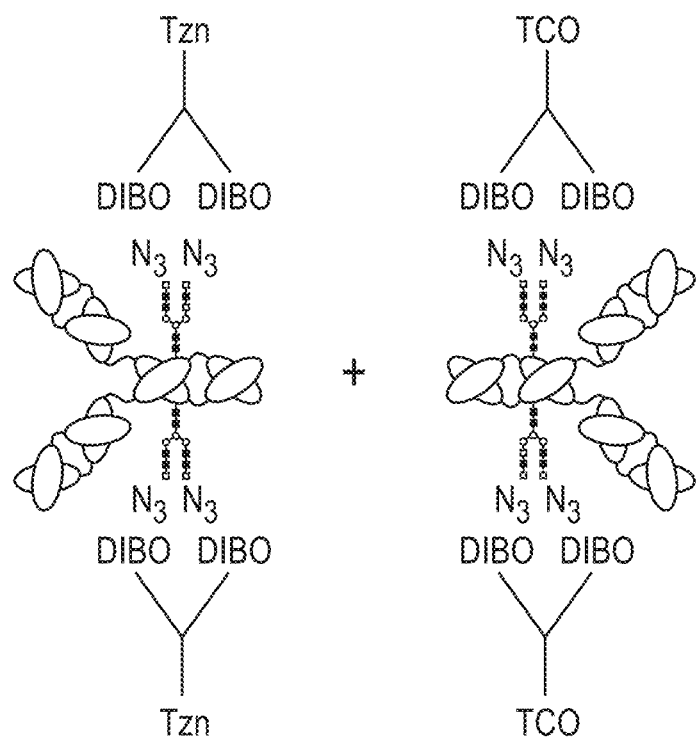
FIG. 2: Schematic of a strategy for making site-specific bispecific antibodies according to certain embodiments of the present disclosure. In this schematic, both the first antibody and second antibody are incubated with β-galactosidase to provide four (4) terminal GlcNAc residues on each antibody to which azide groups may be attached. In this schematic, one antibody is contacted with one DIBO-TCO activating molecule, each activating molecule having two DIBO groups, and the other antibody is contacted with one DIBO-Tzn activating molecule, each activating molecule having two DIBO groups. In this schematic, the final degree of labeling (DOL) is two (2) TCO groups per antibody or two (2) tetrazine groups per antibody.

FIG. 2 depicts a strategy for making site-specific bispecific antibodies according to certain embodiments of the present disclosure. In this schematic, both the first antibody and second antibody are incubated with β-galactosidase to provide four (4) terminal GlcNAc residues on each antibody to which azide groups may be attached. In this schematic, one antibody is contacted with one DIBO-TCO activating molecule, each activating molecule having two DIBO groups, and the other antibody is contacted with one DIBO-Tzn activating molecule, each activating molecule having two DIBO groups. In this schematic, the final degree of labeling (DOL) is two (2) TCO groups per antibody or two (2) tetrazine groups per antibody.

Figure 3A:
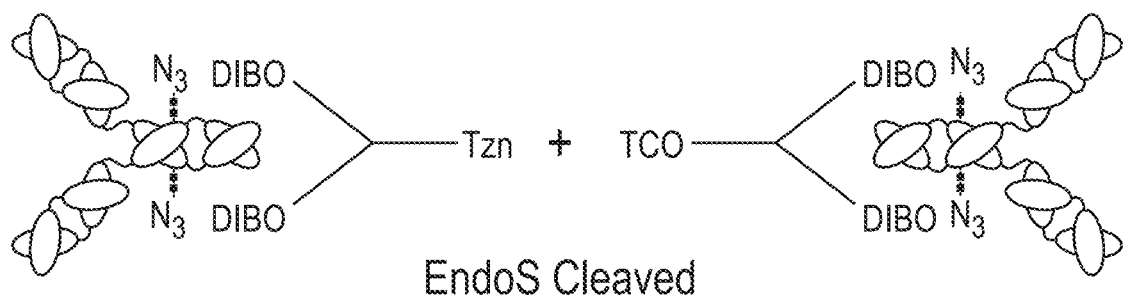
FIG. 3A and FIG. 3B: Schematics of strategies for making site-specific bispecific antibodies according to certain embodiments of the present disclosure. In these schematics, both the first antibody and second antibody are incubated with endoglycosidase S (endoS) to provide two (2) terminal GlcNAc residues on each antibody to which azide groups may be attached.
Figure 3B:
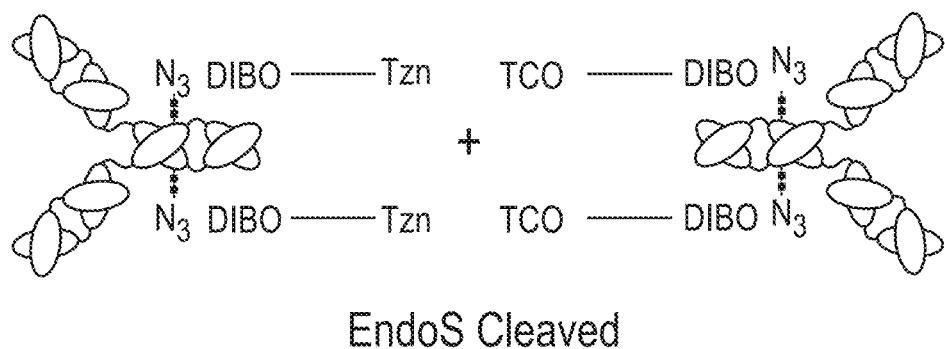

FIGS. 3A and 3B depict strategies for making site-specific bispecific antibodies according to certain embodiments of the present disclosure. In these schematics, both the first antibody and second antibody are incubated with endoglycosidase S to provide two (2) terminal GlcNAc residues on each antibody to which azide groups may be attached. In FIG. 3A, the antibodies that are contacted with activating molecules that have two DIBO groups and in FIG. 3B, the antibodies are contacted with activating molecules that have one DIBO group. The final degree of labeling (DOL) is 1 TCO group or 1 tetrazine group (FIG. 3A), or 2 TCO or tetrazine groups (FIG. 3B).

Figure 4:
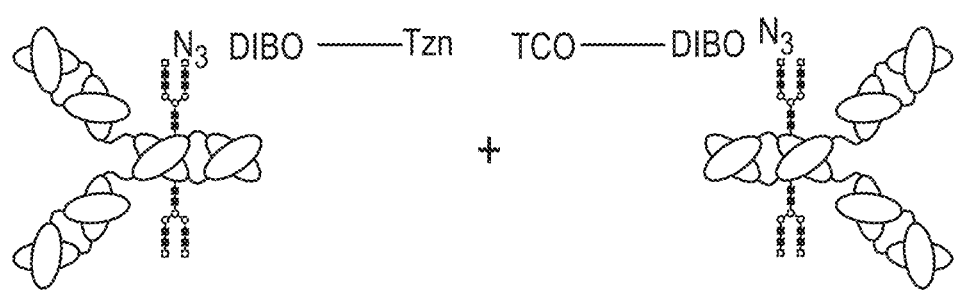
FIG. 4: Schematic of a strategy for making site-specific bispecific antibodies according to certain embodiments of the present disclosure. In this schematic, both antibodies have existing terminal GlcNAc residues and do not require pre-treatment with an enzyme. In this schematic, only one terminal GlcNAc residue is available which results in a final degree of labeling (DOL) of one (1) per antibody.

FIG. 4 depicts a schematic of a strategy for making site-specific bispecific antibodies according to certain embodiments of the present disclosure. In this schematic, both antibodies have existing terminal GlcNAc residues and do not require pre-treatment with an enzyme. In this schematic, only one terminal GlcNAc residue is available which results in a degree of labeling (DOL) of 1.

Figure 5A:
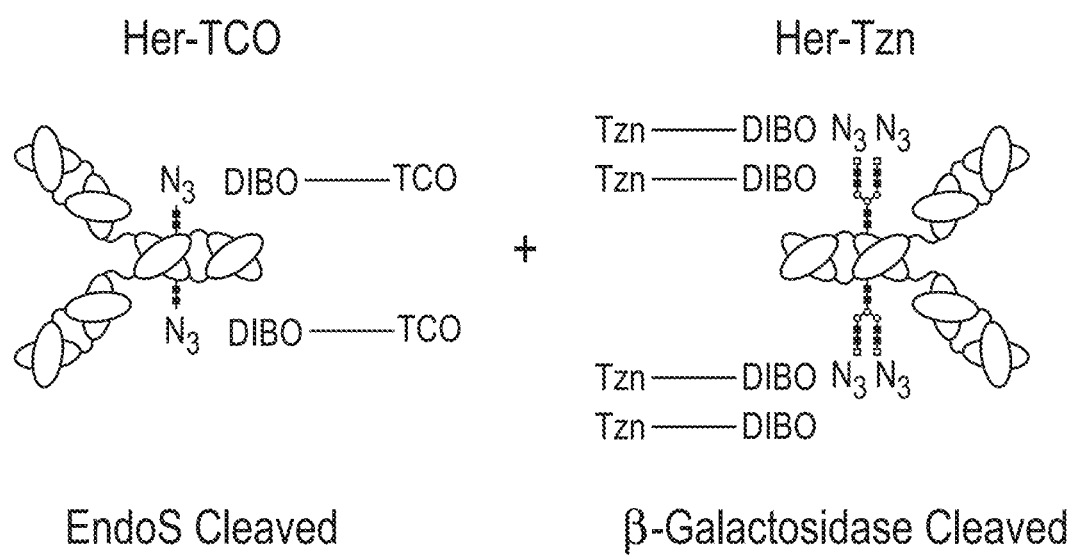
FIG. 5A: Schematic of a strategy for making site-specific bispecific antibodies according to certain embodiments of the present disclosure. In this schematic, as a model system, two HERCEPTIN® (trastuzumab) antibodies (Her) are crosslinked. The first HERCEPTIN® (trastuzumab) antibody is treated with endoglycosidase S (EndoS) to provide terminal GlcNAc residues to which 2 azide groups are added which then react with 2 DIBO reactive groups of the DIBO-TCO activating molecule to form the bispecific antibody Her-TCO. The second HERCEPTIN® (trastuzumab) antibody is treated with 3-galactosidase to provide 4 terminal GlcNAc residues to which azide groups are added which then react with the DIBO reactive group of the DIBO-Tzn activating molecule to form the bispecific antibody Her-Tzn. Although there are multiple crosslinked antibody configurations that can result, presented here are two possible cross-linked products that can result after reducing the antibodies for gel analysis: 1) those with two (2) heavy chains resulting from a cross-linking reaction between one Her-TCO heavy chain and one Her-Tzn heavy chain (molecular weight of the two cross-linked heavy chains is 116 kDa) and 2) those with three (3) heavy chains resulting from a cross-linking reaction between two Her-TCO heavy chains and one Her-Tzn heavy chain (molecular weight of the three cross-linked heavy chains is 174 kDa).

FIG. 5A depicts a strategy for making site-specific bispecific antibodies according to certain embodiments of the present disclosure. In this schematic, as a model system, two HERCEPTIN® (trastuzumab) antibodies are crosslinked. The first HERCEPTIN® (trastuzumab) antibody is treated with endoglycosidase S (EndoS) to provide terminal GlcNAc residues to which 2 azide groups are added which then react with 2 DIBO reactive groups of the DIBO-TCO activating molecule (Her-TCO). The second HERCEPTIN® (trastuzumab) antibody is treated with β-galactosidase to provide 4 terminal GlcNAc residues to which azide groups are added which then react with the DIBO reactive group of the DIBO-Tzn activating molecule (Her-Tzn). Although there are multiple crosslinked antibody configurations that can result, presented here are two possible cross-linked products that can result after reducing the antibodies for gel analysis: 1) those with two (2) heavy chains resulting from a cross-linking reaction between one Her-TCO heavy chain and one Her-Tzn heavy chain (molecular weight of the two cross-linked heavy chains is 116 kDa) and 2) those with three (3) heavy chains resulting from a cross-linking reaction between two Her-TCO heavy chains and one Her-Tzn heavy chain (molecular weight of the three cross-linked heavy chains is 174 kDa).

Figure 5B:
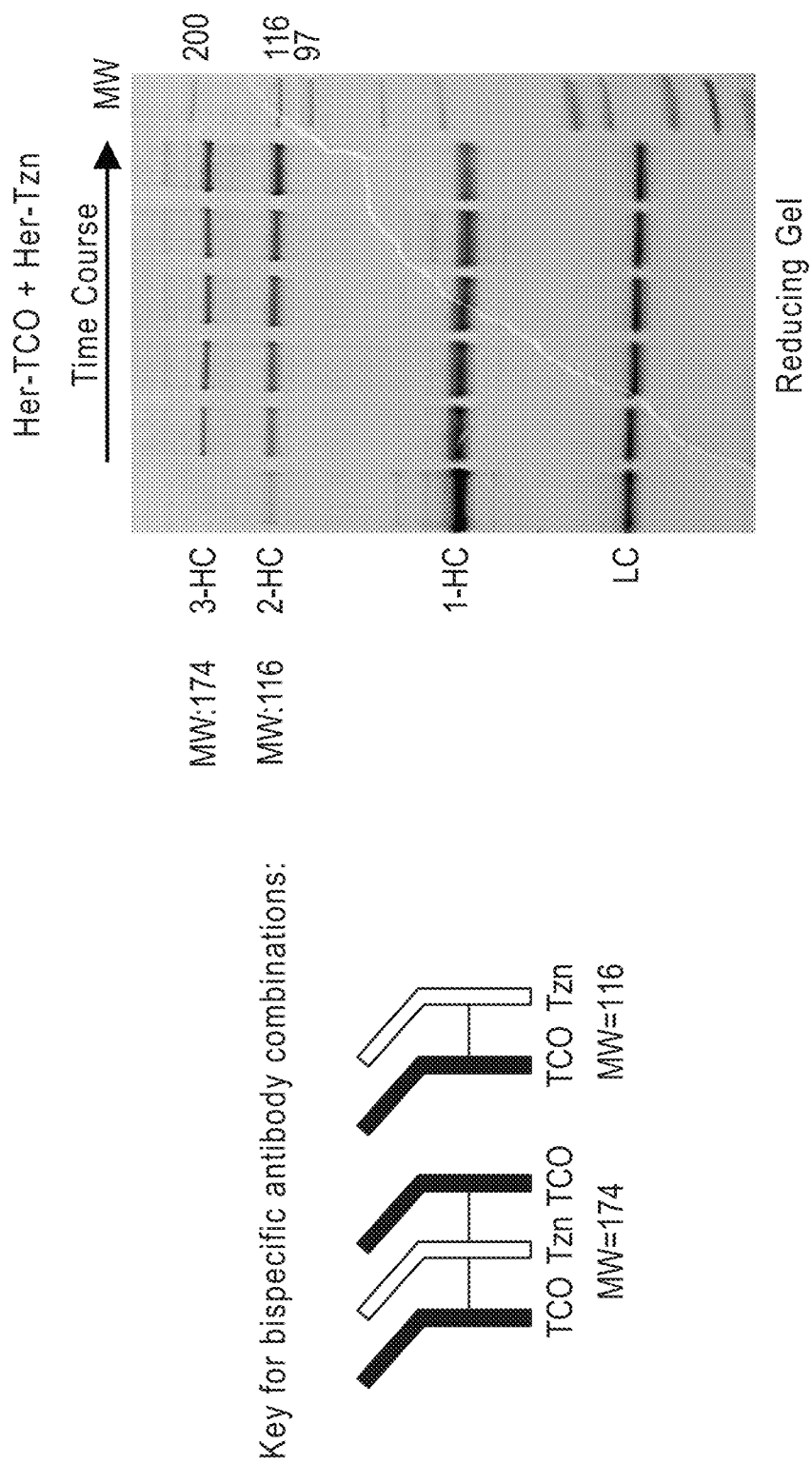
FIG. 5B: A reducing gel showing a time course of the production of the cross-linking reaction products from incubation of Her-TCO and Her-Tzn antibodies. To the left of the gel is a schematic of the two possible cross-linked products: 1) those with two (2) heavy chains resulting from a cross-linking reaction between one Her-TCO heavy chain and one Her-Tzn heavy chain (molecular weight of cross-linked pair is 116 kDa) and 2) those with three (3) heavy chains resulting from a cross-linking reaction between one Her-Tzn heavy chain and two Her-TCO heavy chains (molecular weight of the three cross-linked heavy chains is 174 kDa).

FIG. 5B shows a reducing gel showing a time course of the production of the cross-linking reaction products from incubation of Her-TCO and Her-Tzn antibodies. As described in FIG. 5A, the two possible cross-linked products described are: 1) those with two (2) heavy chains resulting from a cross-linking reaction between one Her-TCO heavy chain and one Her-Tzn heavy chain (molecular weight of cross-linked pair is 116 kDa) and 2) those with three (3) heavy chains resulting from a cross-linking reaction between one Her-Tzn heavy chain and two Her-TCO heavy chains (molecular weight of the three cross-linked heavy chains is 174 kDa).

FIG. 14 depicts a schematic of a strategy for making an antibody conjugate according to certain embodiments of the present disclosure. In this schematic, a trans-cyclooctene (TCO) activated antibody (TCO-activated antibody) is crosslinked to a methyltetrazine (mTzn) activated antibody fragment, specifically an activated Fc protein scaffold (mTzn-PEG-activated human IgG Fc protein). The star denotes compounds and/or labels that are conjugated to the Fc protein. The compounds can be, for example, dyes, chelators, toxins, oligonucleotides, or biotin, and can be attached to the Fc protein at one or more lysine, cysteine and/or methionine residues of the Fc protein.

Certain embodiments provide methods of crosslinking glycoproteins, the methods comprising:

a) providing a first glycoprotein comprising a terminal GlcNAc residue;
b) providing a first modified sugar comprising a first chemical handle;
c) contacting the first glycoprotein with the first modified sugar and a glycosyl transferase enzyme, wherein the glycosyl transferase enzyme catalyzes the attachment of the first modified sugar to the terminal GlcNAc residue of the first glycoprotein thereby forming a first modified glycoprotein;
d) providing a first activating molecule comprising a first crosslinking group, a first reactive group, and optionally, a linker;
e) contacting the first modified glycoprotein with the first activating molecule, wherein the first activating molecule attaches to the first glycoprotein at the first chemical handle, thereby forming a first activated glycoprotein;
f) providing a second glycoprotein comprising a terminal GlcNAc residue;
g) providing a second modified sugar comprising a second chemical handle;
h) contacting the second glycoprotein with the second modified sugar and the glycosyl transferase enzyme, wherein the glycosyl transferase enzyme catalyzes the attachment of the second modified sugar to the terminal GlcNAc residue of the second glycoprotein thereby forming a second modified glycoprotein;
i) providing a second activating molecule comprising a second crosslinking group, a second reactive group, and optionally, a linker;
j) contacting the second modified glycoprotein with the second activating molecule, wherein the second activating molecule attaches to the second modified glycoprotein at the second chemical handle, thereby forming a second activated glycoprotein; and
k) contacting the first activated glycoprotein with the second activated glycoprotein, wherein the first crosslinking group of the first activated glycoprotein reacts with the second crosslinking group of the second activated glycoprotein, thereby forming the crosslinked glycoprotein.

In certain embodiments, the first and/or second glycoprotein is an antibody, an antibody fragment or an Fc-fusion protein. In certain embodiments, the first glycoprotein is an antibody and the second glycoprotein is an antibody. In certain embodiments, the first glycoprotein is an antibody and the second glycoprotein is an antibody fragment. In certain embodiments, the first glycoprotein is an antibody and the second glycoprotein is an Fc-fusion protein. In certain embodiments, the first glycoprotein is an antibody fragment and the second glycoprotein is an antibody. In certain embodiments, the first glycoprotein is an antibody fragment and the second glycoprotein is an antibody fragment. In certain embodiments, the first glycoprotein is an antibody fragment and the second glycoprotein is an Fc-fusion protein. In certain embodiments, the first glycoprotein is an Fc-fusion protein and the second glycoprotein is an antibody. In certain embodiments, the first glycoprotein is an Fc-fusion protein and the second glycoprotein is an antibody fragment. In certain embodiments, the first glycoprotein is an Fc-fusion protein and the second glycoprotein is an Fc-fusion protein. In certain embodiments, the antibody fragment is an Fc protein. In certain embodiments, the Fc protein is an Fc protein scaffold.

In certain embodiments, the first antibody, antibody fragment, or Fc-fusion protein and the second antibody, antibody fragment or Fc-fusion protein contain a single crosslink. In certain embodiments, the first antibody, antibody fragment or Fc-fusion protein and the second antibody, antibody fragment or Fc-fusion protein contain two crosslinks.

In certain embodiments, the terminal GlcNAc residue on the first antibody, antibody fragment or Fc-fusion protein and/or second antibody, antibody fragment or Fc-fusion protein is attached to an asparagine. In certain embodiments, the asparagine is located on the Fc region of an antibody or antibody fragment. In certain embodiments, the asparagine on the Fc region is at amino acid position 287 (Asn287).

Certain embodiments provide methods of crosslinking antibodies, antibody fragments comprising a terminal GlcNAc residue, and/or Fc-fusion proteins to produce a bispecific antibody or antibody conjugate, the methods comprising:
- a) providing:
  - i) a first antibody comprising a terminal GlcNAc residue,
  - ii) a first antibody fragment comprising a terminal GlcNAc residue, or
  - iii) a first Fc-fusion protein comprising a terminal GlcNAc residue;
- b) providing a first modified sugar comprising a first chemical handle;
- c) contacting the first antibody, first antibody fragment or first Fc-fusion protein with the first modified sugar and a glycosyl transferase enzyme, wherein the glycosyl transferase enzyme catalyzes the attachment of the first modified sugar to the terminal GlcNAc residue of the first antibody, first antibody fragment, or first Fc-fusion protein thereby forming a first modified antibody, a first modified antibody fragment, or a first modified Fc-fusion protein;
- d) providing a first activating molecule comprising a first crosslinking group, a first reactive group, and optionally a linker;
- e) contacting the first modified antibody, first modified antibody fragment, or first modified Fc-fusion protein with the first activating molecule, wherein the first activating molecule attaches to the first modified antibody, first modified antibody fragment, or first Fc-fusion protein at the first chemical handle, thereby forming a first activated antibody, first activated antibody fragment or first activated Fc-fusion protein;
- f) providing:
  - iv) a second antibody comprising a terminal GlcNAc residue,
  - v) a second antibody fragment comprising a terminal GlcNAc residue, or
  - vi) a second Fc-fusion protein comprising a terminal GlcNAc residue;
- g) providing a second modified sugar comprising a second chemical handle;
- h) contacting the second antibody, second antibody fragment or second Fc-fusion protein with the second modified sugar and the glycosyl transferase enzyme, wherein the glycosyl transferase enzyme catalyzes the attachment of the second modified sugar to the terminal GlcNAc residue of the second antibody thereby forming a second modified antibody, a second modified antibody fragment, or a second modified Fc-fusion protein;
- i) providing a second activating molecule comprising a second crosslinking group, a second reactive group and optionally, a linker;
- j) contacting the second modified antibody, second modified antibody fragment, or second modified Fc-fusion protein with the second activating molecule, wherein the second activating molecule attaches to the second modified antibody, second modified antibody fragment, or second modified Fc-fusion protein at the second chemical handle, thereby forming a second activated antibody, a second activated antibody fragment, or a second modified Fc-fusion protein; and
- k) contacting the first activated antibody, first activated antibody fragment, or first activated Fc-fusion protein with the second activated antibody, second activated antibody fragment, or second activated Fc-fusion protein, wherein the first crosslinking group of the first activated antibody, first activated antibody fragment, or first activated Fc-fusion protein reacts with the second crosslinking group of the second activated antibody, second activated antibody fragment, or second activated Fc-fusion protein, thereby forming the bispecific antibody or antibody conjugate.

In certain embodiments, the first antibody fragment or the second antibody fragment is an Fc protein. In certain embodiments, the Fc protein is an Fc protein scaffold and the antibody conjugate is an antibody-Fc protein scaffold conjugate.

In certain embodiments, the first antibody, antibody fragment, or Fc-fusion protein and the second antibody, antibody fragment or Fc-fusion protein contain a single crosslink. In certain embodiments, the first antibody, antibody fragment or Fc-fusion protein and the second antibody, antibody fragment or Fc-fusion protein contain two crosslinks.

In certain embodiments, the terminal GlcNAc residue on the first antibody, antibody fragment or Fc-fusion protein and/or second antibody, antibody fragment or Fc-fusion protein is attached to an asparagine. In certain embodiments, the asparagine is located on the Fc region of an antibody or antibody fragment. In certain embodiments, the asparagine on the Fc region is at amino acid position 287 (Asn287).

In certain embodiments, methods are provided for making bispecific antibodies or antibody conjugates, the methods comprising:
- a) providing a first activated antibody, first activated antibody fragment, or first activated Fc-fusion protein comprising a first activating molecule comprising a first crosslinking group, a first reactive group and optionally, a linker;
- b) providing a second activated antibody, second activated antibody fragment, or second activated Fc-fusion protein comprising a second activating molecule comprising a second crosslinking group, a second reactive group and optionally, a linker; and
- c) contacting the first activated antibody, first activated antibody fragment, or first activated Fc-fusion protein with the second activated antibody, second activated antibody fragment, or second activated Fc-fusion protein, wherein the first crosslinking group of the first activated antibody, first activated antibody fragment, or first activated Fc-fusion protein reacts with the second crosslinking group of the second activated antibody, second activated antibody fragment, or second activated Fc-fusion protein, thereby forming the bispecific antibody.

In certain embodiments, the first activated antibody fragment or the second activated antibody fragment is an Fc protein. In certain embodiments, the Fc protein is an Fc protein scaffold and the antibody conjugate is an antibody-Fc protein scaffold conjugate.

In certain embodiments, the first antibody, antibody fragment, or Fc-fusion protein and the second antibody, antibody fragment or Fc-fusion protein contain a single crosslink. In certain embodiments, the first antibody, antibody fragment or Fc-fusion protein and the second antibody, antibody fragment or Fc-fusion protein contain two crosslinks.

In certain embodiments, the terminal GlcNAc residue on the first antibody, antibody fragment or Fc-fusion protein and/or second antibody, antibody fragment or Fc-fusion protein is attached to an asparagine. In certain embodiments, the asparagine is located on the Fc region of an antibody or antibody fragment. In certain embodiments, the asparagine on the Fc region is at amino acid position 287 (Asn287).

In certain embodiments, the first antibody, antibody fragment, or Fc fusion protein and the second antibody, antibody fragment, or Fc fusion protein are the same. In certain embodiments, the first antibody, antibody fragment or fusion protein and the second antibody, antibody fragment, or Fc fusion protein are different.

In certain embodiments, two or more antibodies, antibody fragments comprising a terminal GlcNAc residue, or Fc-fusion proteins can be crosslinked to form a bispecific antibody or antibody conjugate. In certain embodiments, three or more antibodies, antibody fragments comprising a terminal GlcNAc residue, or Fc-fusion proteins can be crosslinked to form a bispecific antibody or antibody conjugate. In certain embodiments, four or more antibodies, antibody fragments comprising a terminal GlcNAc residue, or Fc-fusion proteins can be crosslinked to form a bispecific antibody or antibody conjugate.

In certain embodiments, methods are provided for crosslinking two or more portions of the same antibody, antibody fragment comprising a terminal GlcNAc reside, or Fc fusion protein, the methods comprising:
a) providing:
  i) an antibody comprising a terminal GlcNAc residue,
  ii) an antibody fragment comprising a terminal GlcNAc residue, or
  iii) a Fc-fusion protein comprising a terminal GlcNAc residue;
b) providing at least one modified sugar comprising a chemical handle;
c) contacting the antibody, antibody fragment or Fc-fusion protein with the at least one modified sugar and a glycosyl transferase enzyme, wherein the glycosyl transferase enzyme catalyzes the attachment of the at least one modified sugar to the terminal GlcNAc residue of the antibody, antibody fragment, or Fc-fusion protein thereby forming a modified antibody, a modified antibody fragment, or a modified Fc-fusion protein;
d) providing a first activating molecule comprising a first crosslinking group, a first reactive group, and optionally, a linker, and a second activating molecule comprising a second crosslinking group, a second reactive group and optionally, a linker; and
e) contacting the modified antibody, modified antibody fragment, or modified Fc-fusion protein with the first activating molecule and the second activating molecule, wherein the first activating molecule and the second activating molecule attach to the modified antibody, modified antibody fragment, or modified Fc-fusion protein at the chemical handle, thereby forming an activated antibody, an activated antibody fragment, or a modified Fc-fusion protein;
wherein the first crosslinking group reacts with the second crosslinking group thereby forming the crosslinked antibody.

In certain embodiments, the first modified sugar comprising a first chemical handle and the second modified sugar comprising a second chemical handle are different. In certain embodiments, the first modified sugar comprising a chemical handle and the second modified sugar comprising a chemical handle are the same. In certain embodiments, the first and second chemical handles are the same. In certain embodiments, the first and second chemical handles are different. In certain embodiments, the chemical handle is selected from an alkyne-reactive group, an azide-reactive group, a Diels-Alder diene, a Diels-Alder dienophile, a straight chain or branched $C_1$-$C_{12}$ carbon chain bearing a carbonyl group, a —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), or —$ONH_2$ (aminooxy), wherein each $R^1$, $R^2$, and $R^3$ is independently H or alkyl having 1-6 carbons. In certain embodiments, the chemical handle of the first modified sugar and/or the second modified sugar comprises an azide group, an alkyne group, a cycloalkene group, a ketone group, an oxime group or a nitrile oxide group. In certain embodiments, the first modified sugar and/or the second modified sugar is UDP-GalNAz, UDP-GalKyne, UDP-Gal-Cyclopropene, UDP-GalKetone, UDP-Gal-Oxime or UDP-Gal-Nitrile oxide. In certain preferred embodiments, the first and/or second modified sugar comprising a chemical handle is UDP-GalNAz.

In certain embodiments, the chemical handle comprises an azide group, and the reactive group comprises a terminal triarylphosphine, terminal alkyne, or activated alkyne group; or the chemical handle comprises a terminal triarylphosphine, terminal alkyne or activated alkyne group, and the reactive group comprises an azide group. In certain embodiments, the activated alkyne comprises a dibenzocyclooctyne group.

In certain embodiments, the chemical handle comprises an oxime group or a nitrile oxide group and the reactive group comprises an activated alkyne group. In certain embodiments, the chemical handle comprises an activated alkyne group and the chemical handle comprises an oxime group or a nitrile oxide group. In certain embodiments, the activated alkyne group is a dibenzocyclooctyne group.

In certain embodiments, the chemical handle comprises a Diels-Alder diene and the reactive group comprises a Diels-Alder dienophile; or the chemical handle comprises a Diels-Alder dienophile and the reactive group comprises a Diels-Alder diene.

In certain embodiments, the chemical handle comprises a straight chain or branched $C_1$-$C_{12}$ carbon chain bearing a carbonyl group, and the reactive group comprises a —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), or —$ONH_2$ (aminooxy), wherein each $R^1$, $R^2$, and $R^3$ is independently H or alkyl having 1-6 carbons.

In certain embodiments, the chemical handle comprises a cycloalkene and the reactive group comprises a tetrazine.

In certain embodiments, the first reactive group of the first activating molecule is selected from a dibenzocyclooctyne, a difluorocyclooctyne, an aza-dibenzocyclooctyne, or a cyclononyne. In certain embodiments, the first reactive group is 4-dibenzocyclooctynol.

In certain embodiments, the first crosslinking group of the first activating molecule is a cycloalkene or a tetrazine. In certain embodiments, the first crosslinking group of the first activating molecule is a trans-cyclooctene group (TCO), a cyclopropene, or a tetrazine.

In certain embodiments, the second reactive group of the second activating molecule is selected from a dibenzocyclooctyne, a difluorocyclooctyne, an aza-dibenzocyclooctyne, or a cyclononyne. In certain embodiments, the second reactive group is 4-dibenzocyclooctynol. In certain embodiments, the second crosslinking group of the second activating molecule is a trans-cyclooctene (TCO), a cyclopropene, or a tetrazine.

In certain embodiments, the first crosslinking group comprises a trans-cyclooctene or a cyclopropene and the second crosslinking group comprises a tetrazine. In certain embodiments, the first crosslinking group comprises a tetrazine and the second crosslinking group comprises a trans-cyclooctene or a cyclopropene.

In certain embodiments, the first or second activating molecule comprises a linker. In certain embodiments, the first and second activating molecule comprises a linker. In certain embodiments, the linkers of the first and second activating molecules are the same. In certain embodiments, the linkers of the first and second activating molecules are different. In certain embodiments, the linker comprises one or more polyethylene glycol (PEG) groups. In certain embodiments, the linker comprises 1 to 300 PEG groups. In certain embodiments, the linker comprises 1 to 250 PEG groups. In certain embodiments, the linker comprises 1 to 200 PEG groups. In certain embodiments, the linker comprises 1 to 150 PEG groups. In certain embodiments, the linker comprises 1 to 100 PEG groups. In certain embodiments, the linker comprises 1 to 75 PEG groups. In certain embodiments, the linker comprises 1 to 50 PEG groups. In certain embodiments, the linker comprises 1 to 40 PEG groups. In certain embodiments, the linker comprises 1 to 30 PEG groups. In certain embodiments, the linker comprises 1 to 25 PEG groups. In certain embodiment, the linker comprises 1 to 20 PEG groups. In certain embodiments, the linker comprises 1 to 15 PEG groups. In certain embodiments, the linker comprises 1 to 10 PEG groups. In certain embodiments, the linker comprises 1 to 5 PEG groups. In certain embodiments, the linker comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45 46, 47, 48, 49 or 50 PEG groups.

In certain embodiments, the galactosyl transferase enzyme is a mutant galactosyl transferase enzyme. In certain preferred embodiments, the mutant galactosyl transferase enzyme is a Y289L mutant galactosyl transferase enzyme.

In certain embodiments, step (c) is performed in a solution substantially free of proteases.

In certain embodiments, the first antibody comprising a terminal GlcNAc residue or the second antibody comprising a terminal GlcNAc residue is obtained by β-galactosidase enzymatic activity. In certain embodiments, the first antibody fragment comprising a terminal GlcNAc residue or the second antibody fragment comprising a terminal GlcNAc residue is obtained by β-galactosidase enzymatic activity. In certain embodiments, the first Fc-fusion protein comprising a terminal GlcNAc residue or the second Fc-fusion protein comprising a terminal GlcNAc residue is obtained by β-galactosidase enzymatic activity.

In certain embodiments, the first antibody comprising a terminal GlcNAc residue and the second antibody comprising a terminal GlcNAc residue are obtained by β-galactosidase enzymatic activity. In certain embodiments, the first antibody fragment comprising a terminal GlcNAc residue and the second antibody fragment comprising a terminal GlcNAc residue are obtained by β-galactosidase enzymatic activity. In certain embodiments, the first Fc-fusion protein comprising a terminal GlcNAc residue and the second Fc-fusion protein comprising a terminal GlcNAc residue are obtained by β-galactosidase enzymatic activity.

In certain embodiments, the first antibody comprising a terminal GlcNAc residue or the second antibody comprising a terminal GlcNAc residue is obtained by endoglycosidase enzymatic activity. In certain embodiments, the first antibody fragment comprising a terminal GlcNAc residue or the second antibody fragment comprising a terminal GlcNAc residue is obtained by endoglycosidase enzymatic activity. In certain embodiments, the first Fc-fusion protein comprising a terminal GlcNAc residue or the second Fc-fusion protein comprising a terminal GlcNAc residue is obtained by endoglycosidase enzymatic activity.

In certain embodiments, the first antibody comprising a terminal GlcNAc residue and the second antibody comprising a terminal GlcNAc residue are obtained by endoglycosidase enzymatic activity. In certain embodiments, the first antibody fragment comprising a terminal GlcNAc residue and the second antibody fragment comprising a terminal GlcNAc residue are obtained by endoglycosidase enzymatic activity. In certain embodiments, the first Fc-fusion protein comprising a terminal GlcNAc residue and the second Fc-fusion protein comprising a terminal GlcNAc residue are obtained by endoglycosidase enzymatic activity.

In certain embodiments, the first antibody comprising a terminal GlcNAc residue is obtained by β-galactosidase enzymatic activity and the second antibody comprising a terminal GlcNAc residue is obtained by endoglycosidase enzymatic activity. In certain embodiments, the first antibody fragment comprising a terminal GlcNAc residue is obtained by β-galactosidase enzymatic activity and the second antibody fragment comprising a terminal GlcNAc residue is obtained by endoglycosidase enzymatic activity. In certain embodiments, the first Fc-fusion protein comprising a terminal GlcNAc residue is obtained by β-galactosidase enzymatic activity and the second Fc-fusion protein comprising a terminal GlcNAc residue is obtained by endoglycosidase enzymatic activity.

In certain embodiments, the first antibody comprising a terminal GlcNAc residue is obtained by endoglycosidase enzymatic activity and the second antibody comprising a terminal GlcNAc residue is obtained by β-galactosidase enzymatic activity. In certain embodiments, the first antibody fragment comprising a terminal GlcNAc residue is obtained by endoglycosidase enzymatic activity and the second antibody fragment comprising a terminal GlcNAc residue is obtained by β-galactosidase enzymatic activity. In certain embodiments, the first Fc-fusion protein comprising a terminal GlcNAc residue is obtained by endoglycosidase enzymatic activity and the second Fc-fusion protein comprising a terminal GlcNAc residue is obtained by β-galactosidase enzymatic activity In certain embodiments, the first antibody, first antibody fragment or first Fc-fusion protein is treated by β-galactosidase or endoglycosidase enzymatic activity and the second antibody, second antibody fragment, or second Fc-fusion protein is not treated by β-galactosidase or endoglycosidase enzymatic activity. In certain embodiments, the first antibody, first antibody fragment or Fc fusion protein is not treated by β-galactosidase or endoglycosidase enzymatic activity, and the second antibody, second antibody fragment, or second Fc-fusion protein is treated by β-galactosidase or endoglycosidase enzymatic activity. In certain embodiments, neither the first antibody, first antibody fragment or first Fc-fusion protein, nor the second antibody, second antibody fragment or second Fc-fusion protein is treated by β-galactosidase or endoglycosidase enzyme activity.

In certain embodiments, the method further comprises prior to step (a),
providing a first antibody, a first antibody fragment, or a first Fc-fusion protein comprising an oligosaccharide having a GlcNAc-GlcNAc linkage;
providing an enzyme to cleave the oligosaccharide at the GlcNAc-GlcNAc linkage; and
contacting the first antibody, first antibody fragment, or first Fc-fusion protein comprising an oligosaccharide having a GlcNAc-GlcNAc linkage with the enzyme to provide the first antibody comprising a terminal GlcNAc residue, the first antibody fragment comprising a terminal GlcNAc residue or the first Fc-fusion protein comprising a terminal GlcNAc residue.

In certain embodiments, the method further comprises prior to step (f),
providing a second antibody, a second antibody fragment, or a first Fc-fusion protein comprising an oligosaccharide having a GlcNAc-GlcNAc linkage;
providing an enzyme to cleave the oligosaccharide at the GlcNAc-GlcNAc linkage; and
contacting the second antibody, second antibody fragment, or second Fc-fusion protein comprising an oligosaccharide having a GlcNAc-GlcNAc linkage with the enzyme to provide the second antibody comprising a terminal GlcNAc residue, the second antibody fragment comprising a terminal GlcNAc residue, or the second Fc-fusion protein comprising a terminal GlcNAc residue.

Certain embodiments provide a method of making a bispecific antibody or antibody conjugate, the method comprising:
a) providing a first antibody, a first antibody fragment, or a first Fc-fusion protein comprising an oligosaccharide having a GlcNAc-GlcNAc linkage;
b) contacting the first antibody, first antibody fragment, or first Fc-fusion protein comprising an oligosaccharide having a GlcNAc-GlcNAc linkage with an endoglycosidase enzyme to provide a first antibody comprising a terminal GlcNAc residue, a first antibody fragment comprising a terminal GlcNAc residue or a first Fc-fusion protein comprising a terminal GlcNAc residue;
c) providing a first UDP-GalNAz;
d) contacting the first antibody, first antibody fragment or first Fc-fusion protein with the first UDP-GalNAz and a glycosyl transferase enzyme, wherein the glycosyl transferase enzyme catalyzes the attachment of the first GalNAz group of the UDP-GalNAz to the terminal GlcNAc residue of the first antibody, antibody fragment or Fc-fusion protein, thereby forming a first modified antibody, a first modified antibody fragment, or a first modified Fc-fusion protein;
e) providing a DIBO-PEG$_n$-TCO activating molecule, wherein n is 0-300;
f) contacting the first modified antibody, first modified antibody fragment, or first modified Fc-fusion protein with the DIBO-PEG$_n$-TCO, wherein the DIBO group of the DIBO-PEGn-TCO molecule attaches to the azide group of the first modified antibody, first modified antibody fragment, or first modified Fc fusion protein, thereby forming a first activated antibody, first activated antibody fragment or first activated Fc-fusion protein;
g) providing a second antibody, a second antibody fragment, or a second Fc-fusion protein comprising an oligosaccharide having a GlcNAc-GlcNAc linkage;
h) contacting the second antibody, second antibody fragment, or second Fc-fusion protein comprising an oligosaccharide having a GlcNAc-GlcNAc linkage with an endoglycosidase enzyme to provide a second antibody comprising a terminal GlcNAc residue, a second antibody fragment comprising a terminal GlcNAc residue or a second Fc-fusion protein comprising a terminal GlcNAc residue;
i) providing a second UDP-GalNAz;
j) contacting the second antibody, second antibody fragment or second Fc-fusion protein with the second UDP-GalNAz and the glycosyl transferase enzyme, wherein the glycosyl transferase enzyme catalyzes the attachment of the second GalNAz group of the second UDP-GalNAz to the terminal GlcNAc residue of the second antibody thereby forming a second modified antibody, a second modified antibody fragment, or a second modified Fc-fusion protein;
k) providing a DIBO-PEG$_n$-Tetrazine activating molecule, wherein n is 0-300;
l) contacting the second modified antibody, second modified antibody fragment, or second modified Fc-fusion protein with the DIBO-PEG$_n$-Tetrazine activating molecule, wherein the DIBO group of the DIBO-PEG$_n$-Tetrazine activating molecule attaches to the azide group of the second modified antibody, second modified antibody fragment, or second modified Fc-fusion protein, thereby forming a second activated antibody, a second activated antibody fragment, or a second activated Fc-fusion protein; and
m) contacting the first activated antibody, first activated antibody fragment, or first activated Fc-fusion protein with the second activated antibody, second activated antibody fragment, or second activated Fc-fusion protein, wherein the TCO group of the first activated antibody, first activated antibody fragment, or first activated Fc-fusion protein reacts with the Tetrazine group of the second activated antibody, second activated antibody fragment, or second activated Fc-fusion protein, thereby forming the bispecific antibody or antibody conjugate.

In certain embodiments, the enzyme is an endoglycosidase. In certain embodiments, the endoglycosidase is endoglycosidase S. In preferred embodiments, the endoglycosidase is endoglycosidase S2.

In certain embodiments, the method further comprises prior to step (a),
providing a first antibody, a first antibody fragment, or a first Fc-fusion protein comprising an oligosaccharide having a NeuAc-Gal-GlcNAc linkage;
providing an enzyme to cleave the oligosaccharide at the NeuAc-Gal-GlcNAc linkage; and
contacting the first antibody, first antibody fragment, or first Fc-fusion protein comprising an oligosaccharide having a NeuAc-Gal-GlcNAc linkage with the enzyme to provide a first antibody, first antibody fragment, or first Fc-fusion protein comprising an oligosaccharide having a Gal-GlcNAc linkage.

In certain embodiments, the enzyme is a sialidase.

In certain embodiments, the method further comprises the steps of
providing an enzyme to cleave the oligosaccharide at the Gal-GlcNAc linkage; and
contacting the first antibody, first antibody fragment, or first Fc-fusion protein comprising an oligosaccharide having a Gal-GlcNAc linkage with the enzyme to provide the first antibody comprising a terminal GlcNAc residue, the first antibody fragment comprising a terminal GlcNAc residue, or the first Fc-fusion protein comprising a terminal GlcNAc residue.

In certain embodiments, the enzyme is a β-galactosidase.

In certain embodiments, the method further comprises prior to step (f),
providing a second antibody, a second antibody fragment, or a second Fc-fusion protein comprising an oligosaccharide having a NeuAc-Gal-GlcNAc linkage;
providing an enzyme to cleave the oligosaccharide at the NeuAc-Gal-GlcNAc linkage; and
contacting the second antibody, second antibody fragment, or second Fc-fusion protein comprising an oligosaccharide having a NeuAc-Gal-GlcNAc linkage with the enzyme to provide a second antibody, second antibody fragment, or second Fc-fusion protein comprising an oligosaccharide having a Gal-GlcNAc linkage.

In certain embodiments, the enzyme is a sialidase.

In certain embodiments, the method further comprises the steps of
providing an enzyme to cleave the oligosaccharide at the Gal-GlcNAc linkage; and
contacting the second antibody, second antibody fragment, or second Fc-fusion protein comprising an oligosaccharide having a Gal-GlcNAc linkage with the enzyme to provide the second antibody comprising a terminal GlcNAc residue, the second antibody fragment comprising a terminal GlcNAc residue, or the second Fc-fusion protein comprising a terminal GlcNAc residue.

In certain embodiments, the enzyme is a β-galactosidase.

In certain embodiments, the method further comprises prior to step (a),
providing a first antibody, first antibody fragment or a first Fc-fusion protein comprising an oligosaccharide having a Gal-GlcNAc linkage;
providing an enzyme to cleave the oligosaccharide at the Gal-GlcNAc linkage; and
contacting the first antibody, first antibody fragment or a first Fc-fusion protein comprising an oligosaccharide having a Gal-GlcNAc linkage with the enzyme to provide the first antibody comprising a terminal GlcNAc residue, the first antibody fragment comprising a terminal GlcNAc residue or the first Fc-fusion protein comprising a terminal GlcNAc residue.

In certain embodiments, the method further comprises prior to step (f),
providing a second antibody, second antibody fragment or second Fc-fusion protein comprising an oligosaccharide having a Gal-GlcNAc linkage;
providing an enzyme to cleave the oligosaccharide at the Gal-GlcNAc linkage; and
contacting the second antibody, second antibody fragment or second Fc-fusion protein comprising an oligosaccharide having a Gal-GlcNAc linkage with the enzyme to provide the second antibody comprising a terminal GlcNAc residue, the second antibody fragment comprising a terminal GlcNAc residue, or the second Fc-fusion protein comprising a terminal GlcNAc residue.

In certain embodiments, the enzyme is a β-galactosidase.

In certain embodiments of any of the methods described herein,
(i) steps (a) through (e) are performed before steps (f) through (j);
(ii) steps (a) through (e) are performed after steps (f) through (j); or
(iii) steps (a) through (e) are performed concurrently with steps (f) through (j).

Methods of Site-Specifically Conjugating Antibodies to Liposomes, mRNA or siRNA

Figure 17:
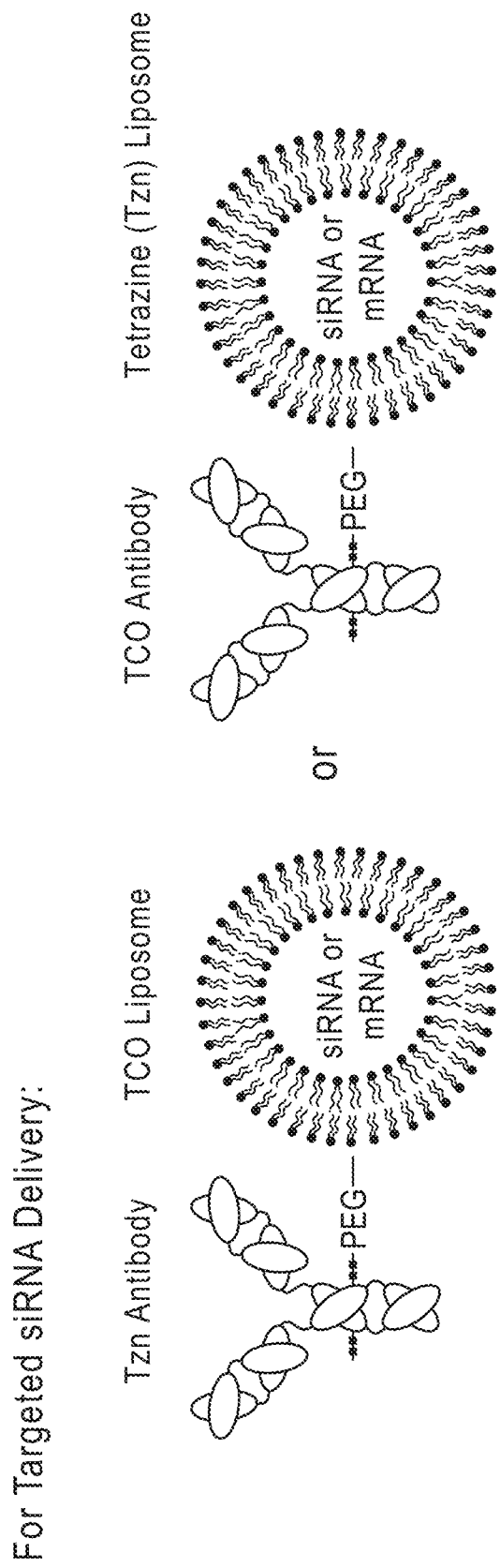
FIG. 17: Schematic of antibody-conjugated liposomes made according to certain embodiments of the present disclosure. The left panel shows a tetrazine (Tzn)-activated antibody crosslinked to a trans-cyclooctene (TCO)-activated liposome surrounding siRNA or mRNA. The right panel shows a TCO-activated antibody cross-linked to a Tzn-activated liposome surrounding siRNA or mRNA. Both antibody-conjugated liposomes depicted in the figure can be used for targeted RNA delivery.

FIG. 17 depicts a schematic of antibody-conjugated liposomes made according to certain embodiments of the present disclosure. The left panel shows a tetrazine (Tzn)-activated antibody cross-linked to a trans-cyclooctene (TCO)-activated liposome surrounding siRNA or mRNA. The right panel shows a TCO-activated antibody cross-linked to a Tzn-activated liposome surrounding siRNA or mRNA. Both antibody-conjugated liposomes depicted in the figure can be used for targeted RNA delivery.

Figure 18:
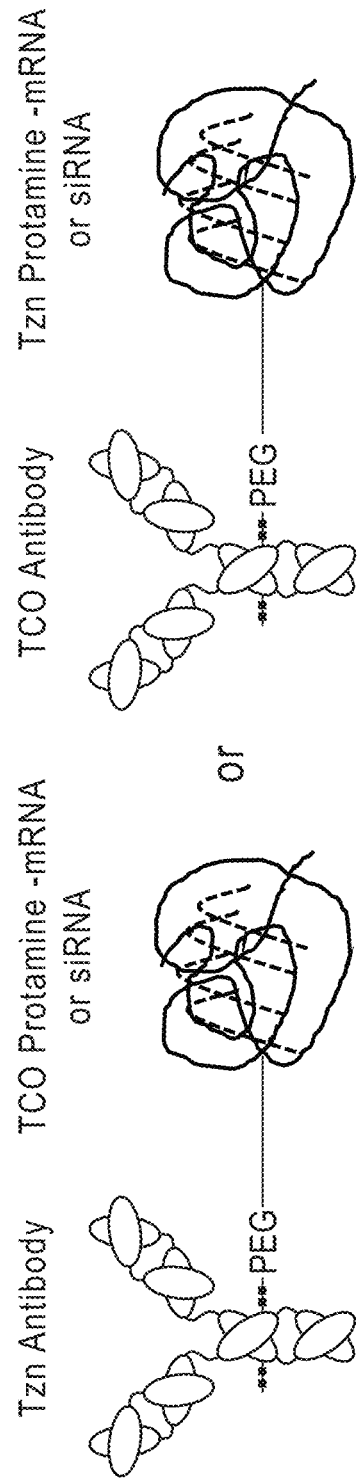
FIG. 18: Schematic of antibody-conjugated mRNA or siRNA made according to certain embodiments of the present disclosure. The left panel shows a tetrazine (Tzn)-activated antibody cross-linked to a trans-cyclooctene (TCO)-activated protamine-siRNA or mRNA. The right panel shows a TCO-activated antibody cross-linked to a Tzn-activated protamine-siRNA or mRNA. Both antibody-conjugated siRNA and mRNA depicted in the figure can be used for targeted mRNA delivery.

FIG. 18 depicts a schematic of antibody-conjugated mRNA or siRNA made according to certain embodiments of the present disclosure. The left panel shows a tetrazine (Tzn)-activated antibody cross-linked to a trans-cyclooctene (TCO)-activated protamine-siRNA or mRNA. The right panel shows a TCO-activated antibody cross-linked to a Tzn-activated protamine-siRNA or mRNA. The antibody-conjugated siRNA and/or the antibody-conjugated mRNA depicted in the figure can be used for targeted mRNA delivery.

Certain embodiments provide methods for producing an antibody-conjugated liposome, the methods comprising:
a) providing an activated antibody, activated antibody fragment, or activated Fc-fusion protein comprising a crosslinking group, a reactive group and optionally, a linker;
b) providing a liposome comprising at least one tetrazine-, trans-cyclooctene (TCO)- or cyclopropene-modified fatty acid; and
c) contacting the activated antibody, activated antibody fragment or activated Fc-fusion protein with the liposome, wherein the crosslinking group of the activated antibody, activated antibody fragment or activated Fc-fusion protein reacts with the tetrazine-modified fatty acid, the cyclopropene-modified fatty acid or the TCO-modified fatty acid of the liposome, thereby forming the antibody-conjugated liposome.

In certain embodiments, methods of producing an antibody-conjugated liposome are provided, the methods comprising:
a) providing
i) an antibody comprising a terminal GlcNAc residue,
ii) an antibody fragment comprising a terminal GlcNAc residue, or
iii) an Fc-fusion protein comprising a terminal GlcNAc residue;
b) providing a modified sugar comprising a chemical handle;
c) contacting the antibody, antibody fragment or Fc-fusion protein with the modified sugar and a glycosyl transferase enzyme, wherein the glycosyl transferase enzyme catalyzes the attachment of the modified sugar to the terminal GlcNAc residue of the antibody to provide a modified antibody, a modified antibody fragment or a modified Fc-fusion protein;

d) providing an activating molecule comprising a crosslinking group, a reactive group and optionally, a linker;

e) contacting the modified antibody, modified antibody fragment, or modified Fc-fusion protein with the activating molecule, wherein the activating molecule attaches to the modified antibody, modified antibody fragment or modified Fc-fusion protein at the chemical handle, thereby forming an activated antibody, an activated antibody fragment, or an activated Fc-fusion protein;

f) providing a liposome comprising at least one trans-cyclooctene (TCO)-modified fatty acid, cyclopropene-modified fatty acid or tetrazine-modified fatty acid; and g) contacting the activated antibody, activated antibody fragment, or activated Fc-fusion protein with the liposome, wherein the crosslinking group of the activated antibody, activated antibody fragment, or activated Fc-fusion protein reacts with the trans-cyclooctene (TCO)-modified fatty acid, cyclopropene-modified fatty acid or tetrazine-modified fatty acid of the liposome, thereby forming the antibody-conjugated liposome.

In certain embodiments methods are provided for producing an antibody-conjugated liposome, the methods comprising:

a) providing
  i) an antibody comprising a terminal GlcNAc residue,
  ii) an antibody fragment comprising a terminal GlcNAc residue, or
  iii) an Fc-fusion protein comprising a terminal GlcNAc residue;

b) providing a modified sugar comprising a chemical handle;

c) contacting the antibody, antibody fragment or Fc-fusion protein with the modified sugar and a glycosyl transferase enzyme, wherein the glycosyl transferase enzyme catalyzes the attachment of the modified sugar to the terminal GlcNAc residue of the antibody to provide a modified antibody, a modified antibody fragment or a modified Fc-fusion protein;

d) providing fatty acid comprising a reactive group;

e) contacting the modified antibody, modified antibody fragment, or modified Fc-fusion protein with the fatty acid comprising a reactive group, wherein the reactive group attaches to the modified antibody, modified antibody fragment or modified Fc-fusion protein at the chemical handle, thereby forming a fatty acid-activated antibody, a fatty acid-activated antibody fragment, or a fatty acid-activated Fc-fusion protein;

f) providing a liposome; and g) contacting the fatty acid-activated antibody, fatty acid-activated antibody fragment, or fatty acid-activated Fc-fusion protein with the liposome, wherein the fatty acid of the fatty acid-activated antibody, fatty acid-activated antibody fragment, or fatty acid-activated Fc-fusion protein is embedded into the liposome, thereby forming the antibody-conjugated liposome.

In certain embodiments, the modified sugar comprising a chemical handle is selected from an alkyne-reactive group, an azide-reactive group, a Diels Alder diene, a Diels Alder dienophile, a straight chain or branched $C_1$-$C_{12}$ carbon chain bearing a carbonyl group, a —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), or —$ONH_2$ (aminooxy), wherein each $R^1$, $R^2$, and $R^3$ is independently H or alkyl having 1-6 carbons. In certain embodiments, the chemical handle comprises an azide group, an alkyne group, a ketone group, an oxime group or a nitrile oxide group. In certain embodiments, the first and/or second modified sugar is UDP-GalNAz, UDP-GalKyne, UDP-GalKetone, UDP-Gal-Oxime or UDP-Gal-Nitrile oxide. In certain embodiments, the first and/or second modified sugar comprising a chemical handle is UDP-GalNAz.

In certain embodiments, the chemical handle comprises an azide group, and the reactive group comprises a terminal triarylphosphine, terminal alkyne, or activated alkyne group; or the chemical handle comprises a terminal triarylphosphine, terminal alkyne or activated alkyne group, and the reactive group comprises an azide group. In certain embodiments, the activated alkyne comprises a dibenzocyclooctyne group.

In certain embodiments, the chemical handle comprises an oxime group or a nitrile oxide group and the reactive group comprises an activated alkyne group. In certain embodiments, the chemical handle comprises an activated alkyne group and the chemical handle comprises an oxime group or a nitrile oxide group. In certain embodiments, the activated alkyne group is a dibenzocyclooctyne group.

In certain embodiments, the chemical handle comprises a Diels-Alder diene and the reactive group comprises a Diels-Alder dienophile; or the chemical handle comprises a Diels-Alder dienophile and the reactive group comprises a Diels-Alder diene.

In certain embodiments, the chemical handle comprises a straight chain or branched $C_1$-$C_{12}$ carbon chain bearing a carbonyl group, and the reactive group comprises a —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$(SO_2)NR^1NH_2$ (sulfonylhydrazide), —$NR^1NR^2(C=O)NR^3NH_2$ (carbazide), —$NR^1NR^2(C=S)NR^3NH_2$ (thiocarbazide), or —$ONH_2$ (aminooxy), wherein each $R^1$, $R^2$, and $R^3$ is independently H or alkyl having 1-6 carbons.

In certain embodiments, the chemical handle comprises a cycloalkene and the reactive group comprises a tetrazine.

In certain embodiments, the first crosslinking group of the first activating molecule is a cycloalkene or a tetrazine. In certain embodiments, the crosslinking group is a trans-cyclooctene (TCO), a cyclopropene, or a tetrazine.

In certain embodiments, the glycosyl transferase enzyme is a mutant galactosyl transferase enzyme. In certain preferred embodiments, the mutant galactosyl transferase enzyme is a Y289L mutant galactosyl transferase enzyme.

In certain embodiments, the liposomes contain alkyne-modified lipids such as 15-hexadecynoic acid.

In certain embodiments, the method further comprises prior to step (a),
  providing an antibody, antibody fragment or Fc-fusion protein comprising an oligosaccharide having a GlcNAc-GlcNAc linkage;
  providing an enzyme to cleave the oligosaccharide at the GlcNAc-GlcNAc linkage; and
  contacting the antibody, antibody fragment or Fc-fusion protein comprising an oligosaccharide having a GlcNAc-GlcNAc linkage with the enzyme to provide the antibody comprising a terminal GlcNAc residue, the antibody fragment comprising a terminal GlcNAc residue, or the Fc binding protein comprising a terminal GlcNAc residue.

In certain embodiments, the enzyme is an endoglycosidase. In a preferred embodiment, the endoglycosidase is endoglycosidase S or endoglycosidase S2.

In certain embodiments, the method further comprises prior to step (a),
providing an antibody, antibody fragment or Fc-fusion protein comprising an oligosaccharide having a NeuAc-Gal-GlcNAc linkage;
providing an enzyme to cleave the oligosaccharide at the NeuAc-Gal-GlcNAc linkage; and
contacting the antibody, antibody fragment or Fc-fusion protein comprising an oligosaccharide having a NeuAc-Gal-GlcNAc linkage with the enzyme to provide an antibody comprising an oligosaccharide having a Gal-GlcNAc linkage.

In certain embodiments, the enzyme is a sialidase.

In certain embodiments, the method further comprises the steps of
providing an enzyme to cleave the oligosaccharide at the Gal-GlcNAc linkage; and
contacting the antibody, antibody fragment or Fc-fusion protein comprising an oligosaccharide having a Gal-GlcNAc linkage with the enzyme to provide the antibody comprising a terminal GlcNAc residue, the antibody fragment comprising a terminal GlcNAc residue, or the Fc binding protein comprising a terminal GlcNAc residue.

In certain embodiments, the enzyme is a β-galactosidase.

In certain embodiments, the method further comprises prior to step (a),
providing an antibody, antibody fragment or Fc-fusion protein comprising an oligosaccharide having a Gal-GlcNAc linkage;
providing an enzyme to cleave the oligosaccharide at the Gal-GlcNAc linkage; and
contacting the antibody, antibody fragment or Fc-fusion protein comprising an oligosaccharide having a Gal-GlcNAc linkage with the enzyme to provide the antibody comprising a terminal GlcNAc residue, the antibody fragment comprising a terminal GlcNAc residue, or the Fc binding protein comprising a terminal GlcNAc residue.

In certain embodiments, the enzyme is a β-galactosidase.

Certain embodiments provide antibody-conjugated liposomes that are obtained by any of the methods provided herein. In certain embodiments, antibody-conjugated liposomes are provided that are obtained by combining an antibody with a modified liposome. In certain embodiments, antibody-conjugated liposomes are provided that are obtained by combining an antibody fragment comprising a terminal GlcNAc residue with a modified liposome. In certain embodiments, antibody-conjugated liposomes are provided that are obtained by combining an Fc-fusion protein with a modified liposome.

Certain embodiments provide methods of producing an antibody-conjugated mRNA or an antibody-conjugated siRNA, the method comprising:
a) providing an activated antibody, antibody fragment or Fc-fusion protein comprising a crosslinking group, a reactive group and optionally, a linker;
b) providing an mRNA or an siRNA;
c) providing a trans-cyclooctene (TCO)-modified RNA polymer, a cyclopropene-modified RNA polymer or a tetrazine-modified RNA polymer;
d) contacting the mRNA or siRNA with the trans-cyclooctene (TCO)-, cyclopropene- or tetrazine-modified RNA binding polymer, wherein the modified RNA binding polymer binds to the mRNA or siRNA thereby forming a modified mRNA or modified siRNA; and
e) contacting the activated antibody, antibody fragment, or Fc-fusion protein with the modified mRNA or modified siRNA, wherein the crosslinking group of the activated antibody, antibody fragment, or Fc-fusion protein reacts with the TCO, cyclopropene or tetrazine moiety of the modified mRNA or modified siRNA, thereby forming the antibody-conjugated mRNA or the antibody-conjugated siRNA.

Certain embodiments provide methods of producing an antibody-conjugated mRNA or siRNA, the method comprising:
a) providing
i) an antibody comprising a terminal GlcNAc residue;
ii) an antibody fragment comprising a terminal GlcNAc residue;
iii) an Fc-fusion protein comprising a terminal GlcNAc residue;
b) providing a modified sugar comprising a chemical handle;
c) contacting the antibody, antibody fragment or Fc-fusion protein with the modified sugar and a glycosyl transferase enzyme, wherein the glycosyl transferase enzyme catalyzes the attachment of the modified sugar to the terminal GlcNAc residue of the antibody, antibody fragment, or Fc-fusion protein to provide a modified antibody, a modified antibody fragment, or a modified Fc-fusion protein;
d) providing an activating molecule comprising a crosslinking group, a reactive group and optionally, a linker;
e) contacting the modified antibody, modified antibody fragment, or modified Fc-fusion protein with the activating molecule, wherein the activating molecule attaches to the modified antibody, modified antibody fragment, or modified Fc-fusion protein at the chemical handle, thereby forming an activated antibody, an activated antibody fragment, or an activated Fc-fusion protein;
f) providing an mRNA or an siRNA;
g) providing a trans-cyclooctene (TCO)-, cyclopropene- or tetrazine-modified RNA binding polymer;
h) contacting the mRNA or siRNA with the trans-cyclooctene (TCO)-, cyclopropene- or tetrazine-modified RNA binding polymer, wherein the modified RNA binding polymer binds to the mRNA or siRNA thereby forming a modified mRNA or modified siRNA; and
i) contacting the activated antibody, activated antibody fragment, or activated Fc-fusion protein with the modified mRNA or modified siRNA, wherein the crosslinking group of the activated antibody, activated antibody fragment, or activated Fc-fusion protein reacts with the TCO, cyclopropene or tetrazine moiety of the modified mRNA or modified siRNA, thereby forming the antibody-conjugated mRNA or antibody-conjugated siRNA.

In certain embodiments, the modified sugar comprising a chemical handle is selected from an alkyne-reactive group, an azide-reactive group, a Diels Alder diene, a Diels Alder dienophile, a straight chain or branched $C_1$-$C_{12}$ carbon chain bearing a carbonyl group, a —$NR^1NH_2$ (hydrazide), —$NR^1(C=O)NR^2NH_2$ (semicarbazide), —$NR^1(C=S)NR^2NH_2$ (thiosemicarbazide), —$(C=O)NR^1NH_2$ (carbonylhydrazide), —$(C=S)NR^1NH_2$ (thiocarbonylhydrazide), —$SO_2$ NR$^1$NH$_2$ (sulfonylhydrazide), —NR$^1$NR$^2$(C═O)NR$^3$NH$_2$ (carbazide), —NR$^1$NR$^2$(C═S)NR$^3$NH$_2$ (thiocarbazide), or —ONH$_2$ (aminooxy), wherein each R$^1$, R$^2$, and R$^3$ is independently H or alkyl having 1-6 carbons. In certain embodiments, the chemical handle comprises an azide group, an alkyne group, a ketone group, an oxime group or a nitrile oxide group. In certain embodiments, the first and/or second modified sugar is UDP-GalNAz, UDP-GalKyne, UDP-Gal-Cyclopropene, UDP-GalKetone, UDP-Gal-Oxime or UDP-Gal-Nitrile oxide. In certain embodiments, the first and/or second modified sugar comprising a chemical handle is UDP-GalNAz.

In certain embodiments, the chemical handle comprises an azide group, and the reactive group comprises a terminal triarylphosphine, terminal alkyne, or activated alkyne group; or the chemical handle comprises a terminal triarylphosphine, terminal alkyne or activated alkyne group, and the reactive group comprises an azide group. In certain embodiments, the activated alkyne comprises a dibenzocyclooctyne group.

In certain embodiments, the chemical handle comprises an oxime group or a nitrile oxide group and the reactive group comprises an activated alkyne group. In certain embodiments, the chemical handle comprises an activated alkyne group and the chemical handle comprises an oxime group or a nitrile oxide group. In certain embodiments, the activated alkyne group is a dibenzocyclooctyne group.

In certain embodiments, the chemical handle comprises a Diels-Alder diene and the reactive group comprises a Diels-Alder dienophile; or the chemical handle comprises a Diels-Alder dienophile and the reactive group comprises a Diels-Alder diene.

In certain embodiments, the chemical handle comprises a straight chain or branched C$_1$-C$_{12}$ carbon chain bearing a carbonyl group, and the reactive group comprises a —NR$^1$NH$_2$ (hydrazide), —NR$^1$(C═O)NR$^2$NH$_2$ (semicarbazide), —NR$^1$(C═S)NR$^2$NH$_2$ (thiosemicarbazide), —(C═O)NR$^1$NH$_2$ (carbonylhydrazide), —(C═S)NR$^1$NH$_2$ (thiocarbonylhydrazide), —(SO$_2$)NR$^1$NH$_2$ (sulfonylhydrazide), —NR$^1$NR$^2$(C═O)NR$^3$NH$_2$ (carbazide), —NR$^1$NR$^2$(C═S)NR$^3$NH$_2$ (thiocarbazide), or —ONH$_2$ (aminooxy), wherein each R$^1$, R$^2$, and R$^3$ is independently H or alkyl having 1-6 carbons.

In certain embodiments, the chemical handle comprises a cycloalkene and the reactive group comprises a tetrazine.

In certain embodiments, the first crosslinking group of the first activating molecule is a cycloalkene or a tetrazine. In certain embodiments, the crosslinking group is a trans-cyclooctene group (TCO) or a tetrazine.

In certain embodiments, the galactosyl transferase enzyme is a mutant galactosyl transferase enzyme. In certain preferred embodiments, the mutant galactosyl transferase enzyme is a Y289L mutant galactosyl transferase enzyme.

In certain embodiments, the method further comprises prior to step (a),
providing an antibody, antibody fragment, or Fc-fusion protein comprising an oligosaccharide having a GlcNAc-GlcNAc linkage;
providing an enzyme to cleave the oligosaccharide at the GlcNAc-GlcNAc linkage; and
contacting the antibody, antibody fragment, or Fc-fusion protein comprising an oligosaccharide having a GlcNAc-GlcNAc linkage with the enzyme to provide the antibody comprising a terminal GlcNAc residue, the antibody fragment comprising a terminal GlcNAc, or the Fc-fusion protein comprising a terminal GlcNAc residue.

In certain embodiments, the enzyme is an endoglycosidase. In certain preferred embodiments, the endoglycosidase is endoglycosidase S or endoglycosidase S2.

In certain embodiments, the method further comprises prior to step (a),
providing an antibody, antibody fragment, or Fc-fusion protein comprising an oligosaccharide having a NeuAc-Gal-GlcNAc linkage;
providing an enzyme to cleave the oligosaccharide at the NeuAc-Gal-GlcNAc linkage; and
contacting the antibody, antibody fragment, or Fc-fusion protein comprising an oligosaccharide having a NeuAc-Gal-GlcNAc linkage with the enzyme to provide an antibody comprising an oligosaccharide having a Gal-GlcNAc linkage.

In certain embodiments, the enzyme is a sialidase.

In certain embodiments, the method further comprises the steps of
providing an enzyme to cleave the oligosaccharide at the Gal-GlcNAc linkage; and
contacting the antibody, antibody fragment, or Fc-fusion protein comprising an oligosaccharide having a Gal-GlcNAc linkage with the enzyme to provide the antibody comprising a terminal GlcNAc residue, the antibody fragment comprising a terminal GlcNAc, or the Fc-fusion protein comprising a terminal GlcNAc residue.

In certain embodiments, the enzyme is a β-galactosidase.

In certain embodiments, the method further comprises prior to step (a),
providing an antibody, antibody fragment, or Fc-fusion protein comprising an oligosaccharide having a Gal-GlcNAc linkage;
providing an enzyme to cleave the oligosaccharide at the Gal-GlcNAc linkage; and
contacting the antibody, antibody fragment, or Fc-fusion protein comprising an oligosaccharide having a Gal-GlcNAc linkage with the enzyme to provide the antibody comprising a terminal GlcNAc residue, the antibody fragment comprising a terminal GlcNAc, or the Fc-fusion protein comprising a terminal GlcNAc residue.

In certain embodiments, the enzyme is a β-galactosidase.

Certain embodiments provide antibody-conjugated mRNA or antibody-conjugated siRNA that are obtained by any of the methods provided herein. In certain embodiments, antibody-conjugated mRNA or antibody-conjugated siRNA are provided that are obtained by combining an antibody with a modified RNA binding polymer bound to an mRNA or an siRNA. In certain embodiments, antibody-conjugated mRNA or antibody-conjugated siRNA are provided that are obtained by combining an antibody fragment comprising a terminal GlcNAc residue with a modified RNA binding polymer bound to an mRNA or an siRNA. In certain embodiments, antibody-conjugated mRNA or antibody-conjugated siRNA are provided that are obtained by combining an Fc-fusion protein with a modified RNA binding polymer bound to an mRNA or an siRNA.

Bispecific Antibodies and Antibody Conjugates:

In certain embodiments, the bispecific antibodies and/or antibody conjugates provided herein are obtained from contacting a first activated antibody, a first activated antibody fragment or a first activated Fc-fusion protein comprising a first crosslinking group with a second activated antibody, a second activated antibody fragment, or a second activated Fc-fusion protein comprising a second crosslinking group, wherein the first crosslinking group of the first activated antibody, first activated antibody, or first activated Fc-fusion protein reacts with the second crosslinking group of the second activated antibody, second activated antibody fragment, or second activated Fc-fusion protein. In certain embodiments, the first activated antibody fragment or the second activated antibody fragment is an Fc protein. In certain embodiments, the Fc protein is an Fc protein scaffold and the antibody conjugate is an antibody-Fc protein scaffold conjugate.

In certain embodiments, the first antibody, antibody fragment, or Fc-fusion protein and the second antibody, antibody fragment or Fc-fusion protein contain a single crosslink. In certain embodiments, the first antibody, antibody fragment or Fc-fusion protein and the second antibody, antibody fragment or Fc-fusion protein contain two crosslinks.

In certain embodiments, the terminal GlcNAc residue on the first antibody, antibody fragment or Fc-fusion protein and/or second antibody, antibody fragment or Fc-fusion protein is attached to an asparagine. In certain embodiments, the asparagine is located on the Fc region of an antibody or antibody fragment. In certain embodiments, the asparagine on the Fc region is at amino acid position 287 (Asn287).

In certain embodiments, the bispecific antibodies or antibody conjugates are at least 50% pure. In certain embodiments, the bispecific antibodies or antibody conjugates are at least 60% pure. In certain embodiments, the bispecific antibodies or antibody conjugates are at least 70% pure. In certain embodiments, the bispecific antibodies or antibody conjugates are at least 80% pure. In certain embodiments, the bispecific antibodies or antibody conjugates are at least 90% pure. In certain embodiments, the bispecific antibodies or antibody conjugates are at least 91%, at least 92%, at least 93%, at least 94% or at least 95% pure. In certain embodiments, the purity of the bispecific antibodies or antibody conjugates is compared to multiply crosslinked higher molecular weight antibody or antibody conjugate species.

In certain embodiments, the bispecific antibodies and/or antibody conjugates provided herein are obtained by any of the methods described herein. In certain embodiments, bispecific antibodies and/or antibody conjugates are provided that are obtained by combining a first antibody with a second antibody. In certain embodiments, bispecific antibodies and/or antibody conjugates are provided that are obtained by combining a first antibody with a second antibody fragment comprising a terminal GlcNAc residue. In certain embodiments, bispecific antibodies and/or antibody conjugates are provided that are obtained by combining a first antibody with a second Fc-fusion protein. In certain embodiments, the second antibody fragment is an Fc protein. In certain embodiments, the Fc protein is an Fc protein scaffold and the antibody conjugate is an antibody-Fc protein scaffold conjugate.

In certain embodiments, bispecific antibodies and/or antibody conjugates are provided that are obtained by combining a first antibody fragment comprising a terminal GlcNAc residue with a second antibody. In certain embodiments, bispecific antibodies and/or antibody conjugates are provided that are obtained by combining a first antibody fragment comprising a terminal GlcNAc residue with a second antibody fragment comprising a terminal GlcNAc residue. In certain embodiments, bispecific antibodies and/or antibody conjugates are provided that are obtained by combining a first antibody fragment comprising a terminal GlcNAc residue with a second Fc-fusion protein. In certain embodiments, the first antibody fragment is an Fc protein. In certain embodiments, the Fc protein is an Fc protein scaffold and the antibody conjugate is an antibody-Fc protein scaffold conjugate.

In certain embodiments, bispecific antibodies and/or antibody conjugates are provided that are obtained by combining a first Fc-fusion protein with a second antibody. In certain embodiments, bispecific antibodies and/or antibody conjugates are provided that are obtained by combining a first Fc-fusion protein with a second antibody fragment comprising a terminal GlcNAc residue. In certain embodiments, bispecific antibodies and/or antibody conjugates are provided that are obtained by combining a first Fc-fusion protein with a second Fc-fusion protein. In certain embodiments, the second antibody fragment is an Fc protein. In certain embodiments, the Fc protein is an Fc protein scaffold and the antibody conjugate is an antibody-Fc protein scaffold conjugate.

In certain embodiments, the first antibody, first antibody fragment or first Fc-fusion protein and the second antibody, second antibody fragment, or second Fc-fusion protein are the same. In certain embodiments, the first antibody, first antibody fragment, or first Fc-fusion protein and the second antibody, second antibody fragment, or second Fc-fusion protein are different. In certain embodiments, one antibody is crosslinked to itself. In certain embodiments, two antibodies, antibody fragments, and/or Fc-fusion proteins are crosslinked to form a bispecific antibody. In certain embodiments, three antibodies, antibody fragments, and/or Fc-fusion proteins are crosslinked to form a bispecific antibody. In certain embodiments, four antibodies, antibody fragments, and/or Fc-fusion proteins are crosslinked to form a bispecific antibody. In certain embodiments, one, two, three, four, or more antibodies, antibody fragments, and/or Fc-fusion proteins are crosslinked to form a bispecific antibody.

In certain embodiments, the antibody conjugates provided herein are obtained from contacting an activated antibody, activated antibody fragment, or activated Fc-fusion protein comprising a first crosslinking group with a Fc protein scaffold, a liposome, an mRNA or a siRNA comprising a second crosslinking group according to any of the methods described herein.

The bispecific antibodies and/or antibody conjugates disclosed herein may bind to two or more different antigens. The bispecific antibody may comprise an antibody, antibody fragment, or combination thereof. The bispecific antibody may comprise an immunoglobulin-immunoglobulin (Ig-Ig) construct, wherein one antibody comprises an immunoglobulin and the other antibody comprises an immunoglobulin. The bispecific antibody may comprise an immunoglobulin-Fab (Ig-Fab) construct, wherein one antibody comprises an immunoglobulin and the other antibody comprises a Fab fragment. The bispecific antibody may comprise a Fab-Fab construct, wherein one antibody comprises a Fab fragment and the other antibody comprises a Fab fragment. The first and second antibodies may be linked by one or more linkers. In certain embodiments, the linker separates the crosslinking group from the reactive group on the activating molecule. In certain embodiments, the linker comprises one or more polyethylene glycol (PEG) groups. In certain embodiments, the linker comprises 1 to 300 PEG groups. In certain embodiments, the linker comprises 1 to 250 PEG groups. In certain embodiments, the linker comprises 1 to 200 PEG groups. In certain embodiments, the linker comprises 1 to 150 PEG groups. In certain embodiments, the linker comprises 1 to 100 PEG groups. In certain embodiments, the linker comprises 1 to 75 PEG groups. In certain embodiments, the linker comprises 1 to 50 PEG groups. In certain embodiments, the linker comprises 1 to 40 PEG groups. In certain embodiments, the linker comprises 1 to 30 PEG groups. In certain embodiments, the linker comprises 1 to 25 PEG groups. In certain embodiment, the linker comprises 1 to 20 PEG groups. In certain embodiments, the linker comprises 1 to 15 PEG groups. In certain embodiments, the linker comprises 1 to 10 PEG groups. In certain embodiments, the linker comprises 1 to 5 PEG groups. In certain embodiments, the linker comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45 46, 47, 48, 49 or 50 PEG groups.

As used herein, the term "antibody fragment" may refer to any form of an antibody other than the full-length form. Antibody fragments herein include antibodies that are smaller components that exist within full-length antibodies, and antibodies that have been engineered. Antibody fragments include, but are not limited to, fragments of antibodies that retain the principal selective binding characteristics of the whole antibody, for example, a sufficient portion of the Fc region to comprise the oligosaccharide linkage site, for example, the asparagine-GlcNAc linkage site (e.g., Asn 287). Unless specifically noted otherwise, statements and claims that use the term "antibody" or "antibodies" may specifically include "antibody fragment" and "antibody fragments."

The antibodies disclosed herein may be human, fully human, humanized, human engineered, non-human, and/or chimeric. The antibodies disclosed herein may be based on or derived from human, fully human, humanized, human engineered, non-human and/or chimeric antibodies. A non-human antibody may be humanized to reduce immunogenicity to humans, while retaining the specificity and affinity of the parental non-human antibody. Generally, a humanized antibody comprises one or more variable domains in which CDRs (or portions thereof) are derived from a non-human antibody, and FRs (or portions thereof) are derived from human antibody sequences. A humanized antibody optionally also comprises at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005); Klimka et al., *Br. J. Cancer,* 83:252-260 (2000) (describing the "guided selection" approach to FR shuffling); and Studnicka et al., U.S. Pat. No. 5,766,886.

Chimeric antibodies may refer to antibodies created through the joining of two or more antibody genes which originally encoded for separate antibodies. A chimeric antibody may comprise at least one amino acid from a first antibody and at least one amino acid from a second antibody, wherein the first and second antibodies are different. The antibodies disclosed herein may comprise antibody sequences from two or more different antibodies. In certain embodiments, one of the antibodies disclosed herein may be a chimeric antibody. Alternatively, or additionally, the other of the antibodies disclosed herein may be a chimeric antibody. The two or more different antibodies may be from the same species. For example, the species may be a bovine species, human species, or murine species. The two or more different antibodies may be from the same type of animal. For example the two or more different antibodies may be from a cow. The two or more different antibodies may be from a human. Alternatively, the two or more different antibodies may be from different species. For example, the two or more different antibodies may be from a human species and bovine species. In another example, the two or more different antibodies may be from a bovine species and a non-bovine species. In another example, the two or more different antibodies may be from a human species and a non-human species.

One or both of the antibodies of the bispecific antibody or antibody conjugate may comprise an antibody or at least a portion of an antibody that is a human, fully human, humanized, human engineered, non-human, or chimeric antibody. One or both of the antibodies may comprise an antibody or at least a portion of an antibody that is a mammalian antibody. One or both of the antibodies may comprise an antibody or at least a portion of an antibody that is a non-mammalian antibody. One or both of the antibodies may comprise an antibody or at least a portion of an antibody that is cross-reactive. One or both of the antibodies may comprise an antibody or at least a portion of an antibody that is species cross-reactive with human and cynomolgus monkey.

The activating molecules used in the methods disclosed herein may comprise one or more linkers. The antibodies disclosed herein may comprise two or more activating molecules. The antibodies disclosed herein may comprise three or more activating molecules. The antibodies disclosed herein may comprise four or more activating molecules. The activating molecules may comprise one or more termini. The activating molecules may comprise two termini. The one or more termini may have a similar orthogonal reactivity. The one or more termini may have a different orthogonal reactivity.

The cross-linking group of the activating molecule may be capable of participating in a bioorthogonal reaction. The crosslinking group may comprise an oxime, a tetrazole, a Diels-Alder adduct, a hetero Diels-Alder adduct, an aromatic substitution reaction product, a nucleophilic substitution reaction product, an ester, an amide, a carbamate, an ether, a thioether, or a Michael reaction product. The bioorthogonal reaction may be a cycloaddition reaction. The cycloaddition may be a copper-free [3+2] Huisgen-cycloaddition. The cycloaddition may be a Diels-Alder reaction. The cycloaddition may be a hetero Diels-Alder reaction.

The cross-linking group of the activating molecule may comprise one or more ethylene glycols. The cross-linking group may comprise at least one reactive functional group selected from alkoxy-amine, hydrazine, aryl/alkyl azide, alkyne, alkene, tetrazine, dichlorotriazine, tresylate, succinimidyl carbonate, benzotriazole carbonate, nitrophenyl carbonate, trichlorophenyl carbonate, carbonylimidazole, succinimidyl succinate, maleimide, vinylsulfone, haloacetamide, and disulfide. The alkene may be selected from norbornene, trans-cyclooctene, and cyclopropene. Each of the one or more linkers may comprise at least one alkoxy amine. The cross-linking group may comprise at least one azide. The cross-linking group may comprise at least one cyclooctyne. The cross-linking group may comprise at least one tetrazine.

The linker of the activating molecule may possess a length that is sufficiently long to allow the cross-linked first antibody or antibody fragment and the second antibody or antibody fragment to be linked without steric hindrance from one another and sufficiently short to retain the intended activity of the antibody. The intended activity of the antibody may be to bring an effector cell and a target cell within a proximity sufficient to allow the targeting cell to have an effect on the target cell. The one or more linkers may be sufficiently hydrophilic that it does not cause instability of the antibody. The one or more linkers may be sufficiently hydrophilic that it does not cause the antibody to be insoluble. The one or more linkers may be sufficiently stable. The one or more linkers may be sufficiently stable in vivo (e.g. it is not cleaved by serum, enzymes, etc.).

In certain embodiments, the first or second activating molecule comprises a linker. In certain embodiments, the first and second activating molecule comprises a linker. In certain embodiments, the linkers of the first and second activating molecule are the same. In certain embodiments, the linkers of the first and second activating molecule are different. In certain embodiments, the linker comprises one or more polyethylene glycol (PEG) groups. In certain embodiments, the linker comprises 1 to 300 PEG groups. In certain embodiments, the linker comprises 1 to 250 PEG groups. In certain embodiments, the linker comprises 1 to 200 PEG groups. In certain embodiments, the linker comprises 1 to 150 PEG groups. In certain embodiments, the linker comprises 1 to 100 PEG groups. In certain embodiments, the linker comprises 1 to 75 PEG groups. In certain embodiments, the linker comprises 1 to 50 PEG groups. In certain embodiments, the linker comprises 1 to 40 PEG groups. In certain embodiments, the linker comprises 1 to 30 PEG groups. In certain embodiments, the linker comprises 1 to 25 PEG groups. In certain embodiment, the linker comprises 1 to 20 PEG groups. In certain embodiments, the linker comprises 1 to 15 PEG groups. In certain embodiments, the linker comprises 1 to 10 PEG groups. In certain embodiments, the linker comprises 1 to 5 PEG groups. In certain embodiments, the linker comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45 46, 47, 48, 49 or 50 PEG groups.

Antibodies for use in the methods disclosed herein may be produced using any means known to those of ordinary skill in the art. General information regarding procedures for antibody production and labeling may be found, for example, in *Antibodies: A Laboratory Manual*, Cold Spring Harbor Laboratory, Chap. 14 (1988). Cell lines expressing antibodies may also be produced using any means known to those of ordinary skill in the art. For therapeutic purposes, chimeric, humanized, and completely human antibodies are useful for applications that include repeated administration to subjects. Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al International Application No. PCT/US86/02269; Akira, et al European Patent Application No. 184,187; Taniguchi, M., European Patent Application Publication No. 171,496; Morrison et al European Patent Application Publication No. 173,494; Neuberger et al PCT International Publication No. WO 86/01533; Cabilly et al U.S. Pat. No. 4,816,567; Cabilly et al European Patent Application Publication No. 125,023; Better et al., *Science* 240: 1041-1043 (1988); Liu et al., *Proc. Natl. Acad. Sci. USA* 84: 3439-3443 (1987); Liu et al., *J. Immunol* 139: 3521-3526 (1987); Sun et al., *Proc. Natl. Acad. Sci. USA* 84: 214-218 (1987); Nishimura et al., *Canc. Res.* 47: 999-1005 (1987); Wood et al., *Nature* 314: 446-449 (1985); and Shaw et al., *J. Natl. Cancer Inst.* 80: 1553-1559 (1988); Morrison, S. L., *Science* 229: 1202-1207 (1985); Oi et al., *BioTechniques* 4: 214 (1986); Winter, U.S. Pat. No. 5,225,539; Jones et al., *Nature* 321: 552-525 (1986); Verhoeyan et al., *Science* 239: 1534; and Beidler et al., *J. Immunol.* 141: 4053-4060 (1988).

Transgenic mice that are incapable of expressing endogenous immunoglobulin heavy and light chains genes, but that can express human heavy and light chain genes, may be used to produce human antibodies for use in the present teachings. See, for example, Lonberg and Huszar, *Int. Rev. Immunol.* 13: 65-93 (1995); and U.S. Pat. Nos. 5,625,126; 5,633,425; 5,569,825; 5,661,016; and 5,545,806. In addition, companies such as Thermo Fisher Scientific (Waltham, Mass.), Abgenix, Inc. (Fremont, Calif.), and Medarex, Inc. (Princeton, N.J.), can be engaged to provide human antibodies directed against a selected antigen using technology similar to that described above. Human antibodies that recognize a selected epitope also can be generated using a technique referred to as "guided selection." In this approach a selected non-human monoclonal antibody (e.g., a murine antibody) is used to guide the selection of a completely human antibody recognizing the same epitope. This technology is described for example by Jespers et al., *Bio/Technology* 12: 899-903 (1994).

The antibodies disclosed herein may be based on or derived from an antibody or antibody fragment from a mammal, bird, fish, amphibian or reptile. Mammals include, but are not limited to, carnivores, rodents, elephants, marsupials, rabbits, bats, primates, seals, anteaters, cetaceans, odd-toed ungulates and even-toed ungulates. The mammal may be a human, non-human primate, mouse, sheep, cat, dog, cow, horse, goat, or pig. Birds include, but are not limited to, albatrosses, hummingbirds, eagles, ostriches, cardinals, kiwis, and penguins. Fish may be cartilaginous fishes, ray-finned fishes, or lobe-fined fishes. Amphibians may include, but are not limited to, newts, salamanders, frogs and toads. Examples of reptiles include, but are not limited to, turtles, squamates, crocodiles and tuataras. Squamates may include amphisbaenians, lizards and snakes.

The antibodies disclosed herein may be cross-species reactive. For example, an antibody may recognize a human antigen and a cynomolgus monkey antigen (e.g. human/cyno antibody).

Oligosaccharides are attached to antibody molecules, such as IgG, at asparagine residues on the Fc portion of the antibody, for example Asn287. At the amino acid, there are two GlcNAc sugars attached to each other by a beta (1-4) linkage. Enzymes such as endoglycosidases cleave this linkage, so that one GlcNAc residue remains attached to the asparagine on the IgG, while the other GlcNAc remains attached to the rest of the oligosaccharide. The GlcNAc attached to the oligosaccharide contains a reactive reducing-end, which can be selectively modified without altering the other sugar residues. Exemplary endoglycosidases include endoglycosidase S, endoglycosidase S2, endoglycosidase F1, endoglycosidase F2, endoglycosidase F3 and endoglycosidase H.

In certain embodiments, the oligosaccharide on the Fc portion of the antibody has a Gal-GlcNAc linkage. Enzymes such as β-galactosidase cleave this linkage so that the GlcNAc residue remains attached to the asparagine on the IgG. The GlcNAc attached to the oligosaccharide contains a reactive reducing-end, which can be selectively modified without altering the other sugar residues.

The enzyme galactosyl transferase normally transfers a galactose from UDP-galactose to a terminal GlcNAc residue. Khidekel et al (*J. Am. Chem. Soc.* 125:16162-16163 (2003); Hsieh-Wilson, L., et al., U.S. Patent Publication No. 2005/0130235) used a mutant galactosyl transferase, a Y289L mutant, to transfer an acetone-containing galactose substrate to a GlcNAc residue. An azide-containing galactose substrate (e.g., UDP-GalNAz) may be synthesized for transfer to the GlcNAc site by the mutant galactosyl transferase.

Unnatural sugar substrates may be synthesized that incorporate reactive chemical handles that may be used for click chemistry. The azide/alkyne cycloaddition reaction can be used to introduce affinity probes (biotin), dyes, polymers (e.g., poly(ethylene glycol) or polydextran) or other monosaccharides (e.g., glucose, galactose, fucose, O-GlcNAc, mannose-derived saccharides bearing the appropriate chemical handle). In certain embodiments, these handles include, for example, azide, triarylphosphine, activated alkyne, cyclooctyne or alkyne residues. The chemical handle also can be an azido group capable of reacting in a Staudinger reaction (see, for example, Saxon, E., et al., *J. Am. Chem. Soc.*, 124(50): 14893-14902 (2002)). The phosphine can have a neighboring acyl group such as an ester, thioester or N-acyl imidazole (i.e. a phosphinoester, phosphinothioester, phosphinoimidazole) to trap the aza-ylide intermediate and form a stable amide bond upon hydrolysis. The phosphine can also be typically a di- or triarylphosphine to stabilize the phosphine.

The antibodies used in the methods disclosed herein may have detectable labels or tags attached thereto. The labels or tags may also, for example, be used for diagnostic or research purposes. Examples of such labels or tags include, but are not limited to fluorescent dyes, such as, for example, fluorescein (FITC), OREGON GREEN® 488 dye, MARINA BLUE® dye, PACIFIC BLUE™ dye, and TEXAS RED®-X dye, ALEXA FLUOR® dyes (Thermo Fisher Scientific, Waltham, MA); compounds containing radioisotopes; phycobiliproteins, such as, for example, R-phycoerythrin (R-PE, allophycocyanin (AP); and particles, such as, for example, QDOT® nanocrystals, gold, ferrofluids, dextrans and microspheres.

Pharmaceutical Compositions:

Certain embodiments provide pharmaceutical compositions comprising the bispecific antibodies disclosed herein. Certain embodiments provide pharmaceutical compositions comprising the antibody conjugates provided herein. Certain embodiments provide pharmaceutical compositions comprising the antibody-conjugated liposomes disclosed herein. Certain embodiments provide pharmaceutical compositions comprising the antibody-conjugated mRNA or antibody-conjugated siRNA disclosed herein. In certain embodiments, the pharmaceutical compositions further comprise a pharmaceutically acceptable carrier, pharmaceutically acceptable excipient or a pharmaceutically acceptable diluent. In certain embodiments, the antibody conjugate is an antibody-Fc protein scaffold conjugate.

Disclosed herein are compositions comprising one or more bispecific antibodies and/or antibody conjugates disclosed herein. The compositions may comprise a bispecific antibody comprising a first antibody, first antibody fragment comprising a terminal GlcNAc residue, or a first Fc fusion protein, and a second antibody, second antibody fragment comprising a terminal GlcNAc residue, or a second Fc-fusion protein, wherein the first antibody or antibody fragment is site-specifically connected to the second antibody, antibody fragment, or Fc-fusion protein. The compositions may comprise a bispecific antibody comprising (a) a first antibody, antibody fragment comprising a terminal GlcNAc residue, or a first Fc-fusion protein; (b) a second antibody, antibody fragment comprising a terminal GlcNAc residue, or a second Fc-fusion protein; and (c) one or more activating molecules comprising a reactive group, a crosslinking group, and optionally, a linker, wherein the activating molecules link the first antibody, antibody fragment, or Fc-fusion protein to the second antibody, antibody fragment, or Fc-fusion protein, and wherein the first antibody, antibody fragment, or Fc-fusion protein is site-specifically linked to the second antibody, antibody fragment, or Fc-fusion protein. The composition may further comprise one or more pharmaceutically acceptable excipients. The composition may further comprise one or more solvents or diluents. In certain embodiments, the first antibody fragment or the second antibody fragment is an Fc protein. In certain embodiments, the Fc protein is an Fc protein scaffold and the antibody conjugate is an antibody-Fc protein scaffold conjugate.

Disclosed herein are compositions comprising one or more antibody-conjugated liposomes disclosed herein. The compositions may comprise an antibody-conjugated liposome comprising an antibody, antibody fragment comprising a terminal GlcNAc residue, or an Fc-fusion protein and a modified liposome, wherein the antibody, antibody fragment, or Fc-fusion protein is site-specifically connected to the modified liposome. The compositions may comprise an antibody-conjugated liposome comprising (a) an antibody, antibody fragment comprising a terminal GlcNAc residue, or Fc-fusion protein; (b) a modified liposome comprising a crosslinking group and optionally a linker, wherein the antibody, antibody fragment, or Fc-fusion protein is site-specifically linked to the modified liposome. The composition may further comprise one or more pharmaceutically acceptable excipients. The composition may further comprise one or more solvents or diluents.

Disclosed herein are compositions comprising one or more antibody-conjugated mRNA or antibody-conjugated siRNA disclosed herein. The compositions may comprise an antibody-conjugated mRNA or antibody-conjugated siRNA comprising an antibody, antibody fragment comprising a terminal GlcNAc residue, or an Fc-fusion protein and a modified mRNA or siRNA, wherein the antibody, antibody fragment, or Fc-fusion protein is site-specifically connected to the modified mRNA or siRNA. The compositions may comprise an antibody-conjugated mRNA or siRNA comprising (a) an antibody, antibody fragment comprising a terminal GlcNAc residue, or Fc-fusion protein; (b) a modified mRNA or siRNA comprising a crosslinking group and optionally a linker, wherein the antibody, antibody fragment, or Fc-fusion protein is site-specifically linked to the modified mRNA or siRNA. The composition may further comprise one or more pharmaceutically acceptable excipients. The composition may further comprise one or more solvents or diluents.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

Pharmaceutical compositions herein may be formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins, 1999).

A pharmaceutical composition disclosed herein may further comprise a pharmaceutically acceptable diluent(s), excipient(s), or carrier(s). The pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

A pharmaceutical composition disclosed herein may be administered to a subject by any suitable administration route, including but not limited to, parenteral (intravenous, subcutaneous, intraperitoneal, intramuscular, intravascular, intrathecal, intravitreal, infusion, or local), topical, oral, or nasal administration. A pharmaceutical composition disclosed herein may be administered to a subject by an intranasal administration. A pharmaceutical composition disclosed herein may be administered to a subject by a microneedle device. The microneedle device may be used to deliver a low dosage of the pharmaceutical composition due to the relatively high potency or efficacy of the antibody. The microneedle device may be a microneedle device as described in U.S. Pat. No. 7,416,541, Peters et al., *Pharm Res.* 29:1618-26 (2012), and Daddona et al., *Pharm Res.* 28:159-65 (2011).

Formulations suitable for intramuscular, subcutaneous, peritumoral or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent may be optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. The pharmaceutical composition described herein may be in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

The pharmaceutical composition described herein may be in unit dosage forms suitable for single administration of precise dosages. In unit dosage form, the formulation may divided into unit doses containing appropriate quantities of an active agent disclosed herein. The unit dosage may be in the form of a package containing discrete quantities of the formulation. Non-limiting examples are packaged tablets or capsules, and powders in vials or ampoules. Aqueous suspension compositions may be packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

For oral administration, the active ingredient can be administered in solid dosage forms, such as capsules, tablets, and powders, or m liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The pharmaceutical composition may be administered at a dosage of about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, about 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg or about 3.0 mg/kg. The pharmaceutical composition may be administered at a dosage of about 3.5 mg/kg, 4.0 mg/kg, 4.5 mg/kg, 5.0 mg/kg, 6.0 mg/kg, 7.0 mg/kg, 8.0 mg/kg, 9.0 mg/kg or about 10 mg/kg.

The pharmaceutical composition may be administered once daily, twice daily, three times daily or more. The pharmaceutical composition may be administered once weekly, twice weekly, three times weekly or more. The pharmaceutical composition may be administered bi-weekly. The pharmaceutical composition may be administered monthly. The pharmaceutical composition may be administered as needed.

The pharmaceutical composition may be co-administered with a therapeutic treatment. The therapeutic treatment may comprise an anti-inflammatory treatment. The anti-inflammatory treatment may comprise a steroid. The anti-inflammatory treatment may comprise a non-steroid. The therapeutic treatment may comprise an antibiotic. The therapeutic treatment may comprise anti-viral drug. The therapeutic treatment may comprise a chemotherapy. The therapeutic treatment may comprise a radiation. The therapeutic treatment may comprise a bispecific antibody. The therapeutic treatment may comprise an additional targeting agent antibody conjugate.

Separation and Detection

Another aspect provided herein are methods directed to detecting and separating the bispecific antibodies and antibody conjugates provided herein using, for example, chromatographic methods or electrophoresis methods such as, but not limited to, thin layer or column chromatography (including, for example, size exclusion, ion exchange, or affinity chromatography) or isoelectric focusing, gel electrophoresis, capillary electrophoresis, capillary gel electrophoresis, and slab gel electrophoresis. Gel electrophoresis may be denaturing or nondenaturing gel electrophoresis, and may include denaturing gel electrophoresis followed by nondenaturing gel electrophoresis (e.g., "2D" gels).

In other embodiments, the separation methods used in such separation and detection methods can be any separation methods used for glycoproteins, such as, for example, chromatography, capture to solid supports, and electrophoresis, such as gel electrophoresis. Gel electrophoresis is well known in the art, and in the context of the present disclosure can be denaturing or nondenaturing gel electrophoresis and can be 1D or 2D gel electrophoresis.

Gel electrophoresis may use any feasible buffer system described herein including, but not limited to, Tris-acetate, Tris-borate, Tris-glycine, BisTris and Bistris-Tricine. In certain embodiments, the electrophoresis gel used in the methods described herein comprise acrylamide, including by way for example only, acrylamide at a concentration from about 2.5% to about 30%, or from about 5% to about 20%. In certain embodiments, such polyacrylamide electrophoresis gels comprise 1% to 10% crosslinker, including but not limited to, bisacrylamide. In certain embodiments, the electrophoresis gel used in the methods described herein comprises agarose, including by way for example only, agarose at concentration from about 0.1% to about 5%, or from about 0.5% to about 4%, or from about 1% to about 3%. In certain embodiments, the electrophoresis gel used in the methods described herein comprises acrylamide and agarose, including by way for example only, electrophoresis gels comprising from about 2.5% to about 30% acrylamide and from about 0.1% to about 5% agarose, or from about 5% to about 20% acrylamide and from about 0.2% to about 2.5% agarose. In certain embodiments, such polyacrylamide/agarose electrophoresis gels comprise 1% to 10% crosslinker, including but not limited to, bisacrylamide. In certain embodiments, the gels used to separate antibodies can be gradient gels.

The methods described herein can be used to detect the bispecific antibodies or the antibody conjugates described herein for "in-gel" detection using slab gel electrophoresis or capillary gel electrophoresis. In certain embodiments such antibodies are antibody fragments.

In-gel fluorescence detection allows for quantitative differential analysis of protein glycosylation between different biological samples and is amenable to multiplexing with other protein gel stains. In certain embodiments of the methods described herein, utilizing fluorescent- and/or UV-excitable alkyne containing probes, or fluorescent- and/or UV-excitable azide containing probes, allow for the multiplexed detection of antibodies, phosphoproteins, and total proteins in the same 1-D or 2-D gels.

The bispecific antibodies and antibody conjugates described herein may, at any time before, after or during an assay, be illuminated with a wavelength of light that results in a detectable optical response, and observed with a means for detecting the optical response. In certain embodiments, such illumination can be by a violet or visible wavelength emission lamp, an arc lamp, a laser, or even sunlight or ordinary room light.

In certain embodiments, the sources used for illuminating include, but are not limited to, hand-held ultraviolet lamps, mercury arc lamps, xenon lamps, argon lasers, laser diodes, blue laser diodes, and YAG lasers. These illumination sources are optionally integrated into laser scanners, flow cytometer, fluorescence microplate readers, standard or mini fluorometers, or chromatographic detectors. The fluorescence emission of such fluorophores is optionally detected by visual inspection, or by use of any of the following devices: CCD cameras, video cameras, photographic film, laser scanning devices, fluorometers, photodiodes, photodiode arrays, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorescent compounds described herein and a second fluorophore with detectably different optical properties, typically by distinguishing the fluorescence response of the fluorescent compounds described herein from that of the second fluorophore. Where a sample is examined using a flow cytometer, examination of the sample optionally includes isolation of particles within the sample based on the fluorescence response by using a sorting device.

In certain embodiments, fluorescence is optionally quenched using either physical or chemical quenching agents.

In certain embodiments, the bispecific antibodies and antibody conjugates described herein may be used to perform diagnostic imaging. The imaging technique may include whole body imaging for diagnostic purposes or local imaging at specific sites, such as but not limited to sites of tumor growth, in a quantitative manner to assess the progression of disease or host response to a treatment regimen. The imaging may be accomplished in vitro or in vivo by any suitable method known in the art. For example, and without wishing to be limiting, the diagnostic imaging technique may include immunohistochemistry, immunofluorescence staining, or a non-invasive (molecular) diagnostic imaging technology including, but not limited to: optical imaging; positron emission tomography (PET), wherein the detectable agent is an isotope such as $^{11}$C, $^{13}$N, $^{15}$O, $^{18}$F, $^{64}$Cu, $^{62}$Cu, $^{124}$I, $^{76}$Br, $^{82}$Rb and $^{68}$Ga; or single photon emission computed tomography (SPECT), wherein the detectable agent is a radiotracer such as $^{99m}$Tc, $^{111}$In, $^{123}$I, $^{201}$Tl, $^{133}$Xe, depending on the specific application.

Samples and Sample Preparation

The end user will determine the choice of the sample and the way in which the sample is prepared. Samples that can be used with the methods and compositions described herein include, but are not limited to, any biological derived material or aqueous solution that contains an analyte. In certain embodiments, a sample also includes material in which a bispecific antibody or antibody conjugate of the present disclosure has been added. The sample that can be used with the methods and compositions described herein can be a biological fluid including, but not limited to, whole blood, plasma, serum, nasal secretions, sputum, saliva, urine, sweat, transdermal exudates, cerebrospinal fluid, or the like. In other embodiments, the samples are biological fluids that include tissue and cell culture medium. Cells used in such cultures include, but are not limited to, prokaryotic cells and eukaryotic cells that include primary cultures and immortalized cell lines. Such eukaryotic cells include, without limitation, ovary cells, epithelial cells, circulating immune cells, β cells, hepatocytes, and neurons. In certain embodiments, the sample may be whole organs, tissue or cells from an animal, including but not limited to, muscle, eye, skin, gonads, lymph nodes, heart, brain, lung, liver, kidney, spleen, thymus, pancreas, solid tumors, macrophages, mammary glands, mesothelium, and the like. In certain embodiments, the sample may be a subject, such as a mammal.

Various buffers can be used in the methods described herein, including inorganic and organic buffers. In certain embodiments the organic buffer is a zwitterionic buffer. By way of example only, buffers that can be used in the methods described herein include phosphate buffered saline (PBS), phosphate, succinate, citrate, borate, maleate, cacodylate, N-(2-Acetamido)iminodiacetic acid (ADA), 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxypropanesulfonic acid (MOPSO), N,N-bis-(hydroxyethyl)-2-aminoethanesulfonic acid (BES), 3-(N-morpholino)-propanesulfonic acid (MOPS), N-tris-(hydroxymethyl)-2-ethanesulfonic acid (TES), N-2-hydroxyethyl-piperazine-N-2-ethanesulfonic acid (HEPES), 3-(N-tris-(hydroxymethyl) methylamino)-2-hydroxypropanesulfonic acid (TAPSO), 3-(N,N-Bis[2-hydroxyethyl]amino)-2-hydroxypropanesulfonic acid (DIPSO), N-(2-Hydroxyethyl)piperazine-N'-(2-hydroxypropanesulfonic acid) (HEPPSO), 4-(2-Hydroxyethyl)-1-piperazinepropanesulfonic acid (EPPS), N-[Tris(hydroxymethyl)methyl]glycine (Tricine), N,N-Bis(2-hydroxyethyl)glycine (Bicine), (2-Hydroxy-1,1-bis(hydroxymethyl)ethyl)amino]-1-propanesulfonic acid (TAPS), N-(1,1-Dimethyl-2-hydroxyethyl)-3-amino-2-hydroxypropanesulfonic acid (AMPSO), tris (hydroxy methyl) amino-methane (Tris), Tris-Acetate-EDTA (TAE), glycine, bis[2-hydroxyethyl]iminotris[hydroxymethyl]methane (BisTris), or combinations thereof. In certain embodiments, wherein such buffers are used in gel electrophoresis separations the buffer can also include ethylene diamine tetraacetic acid (EDTA).

The concentration of such buffers used in the methods described herein is from about 0.1 mM to 1 M. In certain embodiments the concentration is between 10 mM to about 1 M. In certain embodiments the concentration is between about 20 mM and about 500 mM, and in other embodiments the concentration is between about 50 mM and about 300 mM. In certain embodiments, the buffer concentration is from about 0.1 mM to about 50 mM, while in other embodiments the buffer concentration if from about 0.5 mM to about 20 mM.

In certain embodiments, buffers used in the methods described herein have a pH between 5 and 9 at ambient temperature. In certain embodiments the buffer has a pH between 6 and 8.5 at ambient temperature. In certain embodiments the buffer has a pH between 6 and 8 at ambient temperature. In certain embodiments the buffer has a pH between 6 and 7 at ambient temperature. In certain embodiments the buffer has a pH between 5 and 9 at 25° C. In certain embodiments the buffer has a pH between 6 and 8.5 at 25° C. In certain embodiments the buffer has a pH between 6 and 8 at 25° C. In certain embodiments the buffer has a pH between 6 and 7 at 25° C.

In certain embodiments, the samples used in the methods described herein contain a non-ionic detergent. Non-limiting examples of such non-ionic detergents added to the samples used in the methods described herein are polyoxyalkylene diols, ethers of fatty alcohols including alcohol ethoxylates (Neodol from Shell Chemical Company and Tergitol from Union Carbide Corporation), alkyl phenol ethoxylates (Igepal surfactants from General Aniline and Film Corporation), ethylene oxide/propylene oxide block copolymers (PLURONIC™ Series from BASF Wyandotte Corporation), polyoxyethylene ester of a fatty acids (Stearox CD from Monsanto Company), alkyl phenol surfactants (Triton series, including Triton X-100 from Rohm and Haas Company), polyoxyethylene mercaptan analogs of alcohol ethoxylates (Nonic 218 and Stearox SK from Monsanto Company), polyoxyethylene adducts of alkyl amines (Ethoduomeen and Ethomeen surfactants from Armak Company), polyoxyethylene alkyl amides, sorbitan esters (such as sorbitan monolaurate) and alcohol phenol ethoxylate (Surfonic from Jefferson Chemical Company, Inc.). Non-limiting examples of sorbitan esters include polyoxyethylene(20) sorbitan monolaurate (TWEEN20), polyoxyethylene(20) sorbitan monopalmitate (TWEEN40), polyoxyethylene(20) sorbitan monostearate (TWEEN60) and polyoxyethylene(20) sorbitan monooleate (TWEEN 80). In certain embodiments, the concentration of such non-ionic detergents added to a sample is from 0.01 to 0.5%. In other embodiments the concentration is from about 0.01 to 0.4 vol. %. In other embodiments the concentration is from about 0.01 to 0.3 vol. %. In other embodiments the concentration is from about 0.01 to 0.2 vol. %. In other embodiments the concentration is from about 0.01 to 0.1 vol. %.

Kits:

In certain embodiments, kits are provided, wherein the kits comprise:
- a first modified sugar comprising a first chemical handle;
- a second modified sugar comprising a second chemical handle;
- a first activating molecule comprising a first crosslinking group, a first reactive group and optionally, a linker;
- a second activating molecule comprising a second crosslinking group, a second reactive group and optionally, a linker;
- a galactosyl transferase enzyme; and
- instructions for use in any of the methods described herein.

In certain embodiments, the kits further comprise a β-galactosidase enzyme. In certain embodiments, the kits further comprise an endoglycosidase enzyme. In certain embodiments, the endoglycosidase enzyme is endoglycosidase S. In certain preferred embodiments, the endoglycosidase enzyme is endoglycosidase S2.

In certain embodiments, the first modified sugar comprising a chemical handle and the second modified sugar comprising a chemical handle are different. In certain embodiments, the first modified sugar comprising a chemical handle and the second modified sugar comprising a chemical handle are the same. In certain embodiments, the first and second chemical handles are the same. In certain embodiments, the first and second chemical handles are different. In certain embodiments, the chemical handle is selected from an alkyne-reactive group, an azide-reactive group, a Diels-Alder diene, a Diels-Alder dienophile, a straight chain or branched $C_1$-$C_{12}$ carbon chain bearing a carbonyl group, a —$NR^1NH_2$ (hydrazide), —$NR^1(C═O)NR^2NH_2$ (semicarbazide), —$NR^1(C═S)NR^2NH_2$ (thiosemicarbazide), —$(C═O)NR^1NH_2$ (carbonylhydrazide), —$(C═S)NR^1NH_2$ (thiocarbonylhydrazide), —$(SO_2)NR^1NH_2$ (sulfonylhydrazide), —$NR^1NR^2(C═O)NR^3NH_2$ (carbazide), —$NR^1NR^2(C═S)NR^3NH_2$ (thiocarbazide), or —$ONH_2$ (aminooxy), wherein each $R^1$, $R^2$, and $R^3$ is independently H or alkyl having 1-6 carbons. In certain embodiments, the chemical handle of the first modified sugar and/or the second modified sugar comprises an azide group, an alkyne group, a ketone group, an oxime group or a nitrile oxide group. In certain embodiments, the first modified sugar and/or the second modified sugar is UDP-GalNAz, UDP-GalKyne, UDP-Gal-Cyclopropene, UDP-GalKetone, UDP-Gal-Oxime or UDP-Gal-Nitrile oxide. In certain embodiments, the first and/or second modified sugar comprising a chemical handle is UDP-GalNAz.

In certain embodiments, the chemical handle comprises an azide group, and the reactive group comprises a terminal triarylphosphine, terminal alkyne, or activated alkyne group; or the chemical handle comprises a terminal triarylphosphine, terminal alkyne or activated alkyne group, and the reactive group comprises an azide group. In certain embodiments, the activated alkyne comprises a dibenzocyclooctyne group.

In certain embodiments, the chemical handle comprises an oxime group or a nitrile oxide group and the reactive group comprises an activated alkyne group. In certain embodiments, the chemical handle comprises an activated alkyne group and the chemical handle comprises an oxime group or a nitrile oxide group. In certain embodiments, the activated alkyne group is a dibenzocyclooctyne group.

In certain embodiments, the chemical handle comprises a Diels-Alder diene and the reactive group comprises a Diels-Alder dienophile; or the chemical handle comprises a Diels-Alder dienophile and the reactive group comprises a Diels-Alder diene.

In certain embodiments, the chemical handle comprises a straight chain or branched $C_1$-$C_{12}$ carbon chain bearing a carbonyl group, and the reactive group comprises a —$NR^1NH_2$ (hydrazide), —$NR^1(C═O)NR^2NH_2$ (semicarbazide), —$NR^1(C═S)NR^2NH_2$ (thiosemicarbazide), —$(C═O)NR^1NH_2$ (carbonylhydrazide), —$(C═S)NR^1NH_2$ (thiocarbonylhydrazide), —$(SO_2)NR^1NH_2$ (sulfonylhydrazide), —$NR^1NR^2(C═O)NR^3NH_2$ (carbazide), —$NR^1NR^2(C═S)NR^3NH_2$ (thiocarbazide), or —$ONH_2$ (aminooxy), wherein each $R^1$, $R^2$, and $R^3$ is independently H or alkyl having 1-6 carbons.

In certain embodiments, the chemical handle comprises a cycloalkene and the reactive group comprises a tetrazine.

In certain embodiments, the first reactive group of the first activating molecule is selected from a dibenzocyclooctyne, a difluorocyclooctyne, an aza-dibenzocyclooctyne, or a cyclononyne. In certain embodiments, the first reactive group is 4-dibenzocyclooctynol.

In certain embodiments, the first crosslinking group of the first activating molecule is a cycloalkene or a tetrazine. In certain embodiments, the first crosslinking group of the first activating molecule is a trans-cyclooctene (TCO), a cyclopropene, or a tetrazine.

In certain embodiments, the first activating molecule comprises a trans-cyclooctene and a dibenzocyclooctyne.

In certain embodiments, the second reactive group of the second activating molecule is selected from a dibenzocyclooctyne, a difluorocyclooctyne, an aza-dibenzocyclooctyne, or a cyclononyne. In certain embodiments, the second reactive group is 4-dibenzocyclooctynol. In certain embodiments, the second crosslinking group of the second activating molecule is a trans-cyclooctene (TCO), a cyclopropene, or a tetrazine.

In certain embodiments, the first crosslinking group comprises a trans-cyclooctene or a cyclopropene and the second crosslinking group comprises a tetrazine. In certain embodiments, the first crosslinking group comprises a tetrazine and the second crosslinking group comprises a trans-cyclooctene or a cyclopropene.

In certain embodiments, the first or second activating molecule comprises a linker. In certain embodiments, the first and second activating molecule comprises a linker. In certain embodiments, the linkers of the first and second activating molecule are the same. In certain embodiments, the linkers of the first and second activating molecule are different. In certain embodiments, the linker comprises one or more polyethylene glycol (PEG) groups. In certain embodiments, the linker comprises 1 to 300 PEG groups. In certain embodiments, the linker comprises 1 to 250 PEG groups. In certain embodiments, the linker comprises 1 to 200 PEG groups. In certain embodiments, the linker comprises 1 to 150 PEG groups. In certain embodiments, the linker comprises 1 to 100 PEG groups. In certain embodiments, the linker comprises 1 to 75 PEG groups. In certain embodiments, the linker comprises 1 to 50 PEG groups. In certain embodiments, the linker comprises 1 to 40 PEG groups. In certain embodiments, the linker comprises 1 to 30 PEG groups. In certain embodiments, the linker comprises 1 to 25 PEG groups. In certain embodiment, the linker comprises 1 to 20 PEG groups. In certain embodiments, the linker comprises 1 to 15 PEG groups. In certain embodiments, the linker comprises 1 to 10 PEG groups. In certain embodiments, the linker comprises 1 to 5 PEG groups. In certain embodiments, the linker comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45 46, 47, 48, 49 or 50 PEG groups.

In another aspect, kits are provided for use in the methods provided herein. In certain embodiments, kits are provided for cross-linking one, two, three, four, or more antibodies or antibody fragments, preferably two, that comprise a modified sugar comprising a chemical handle, and an activating molecule comprising a cross-linking group and a reactive group. In certain embodiments, the kits further comprise instructions for using the components in any of the methods as described herein. In certain embodiments, kits are provided for making bispecific antibodies that comprise a modified sugar comprising a chemical handle, and an activating molecule comprising a cross-linking group and a reactive group. In certain embodiments, the kits further include instructions for using the components in any of the methods as described herein. In certain embodiments, kits are provided for making an antibody conjugates, for example antibody-Fc protein scaffold conjugates, that include a modified sugar comprising a chemical handle and an activating molecule comprising a cross-linking group and a reactive group. In certain embodiments, the kits further include instructions for using the components in any of the methods as described herein. In certain embodiments, kits are provided for making antibody-conjugated liposomes that include a modified sugar comprising a chemical handle and an activating molecule comprising a cross-linking group and a reactive group. In certain embodiments, the kits further include instructions for using the components in any of the methods as described herein. In certain embodiments, kits are provided for making antibody-conjugated mRNAs or antibody-conjugated siRNAs that comprise a modified sugar comprising a chemical handle, and an activating molecule comprising a cross-linking group and a reactive group. In certain embodiments, the kits further include instructions for using the components in any of the methods described herein.

In certain embodiments, the kits may further include one or more of the following: an endoglycosidase, a sialidase, a β-galactosidase, a galactosyl transferase, a mutant galactosyl transferase, a Y289L mutant galactosyl transferase and an antibody. In certain embodiments, the kits may further include one or more of the following: one or more buffers, detergents and/or solvents.

The kits disclosed herein may also comprise one or more of the components in any number of separate containers, packets, tubes, vials, microtiter plates and the like, or the components may be combined in various combinations in such containers. For the kits disclosed herein, for example, the modified sugar comprising the chemical handle may be provided in a separate container than the labeling molecules.

The kits disclosed herein may also comprise instructions for performing one or more methods described herein and/or a description of one or more compositions or reagents described herein. Instructions and/or descriptions may be in printed form and may be included in a kit insert. A kit also may include a written description of an Internet location that provides such instructions or descriptions.

Methods of Use:

In certain embodiments, a method for screening bispecific antibodies and antibody conjugates is provided, the method comprising:
a) providing:
  i) a first antibody comprising a terminal GlcNAc residue,
  ii) a first antibody fragment comprising a terminal GlcNAc residue, or
  iii) a first Fc-fusion protein comprising a terminal GlcNAc residue;
b) providing a first modified sugar comprising a first chemical handle;
c) contacting the first antibody, first antibody fragment or first Fc-fusion protein with the first modified sugar and a glycosyl transferase enzyme, wherein the glycosyl transferase enzyme catalyzes the attachment of the first modified sugar to the terminal GlcNAc residue of the first antibody, first antibody fragment, or first Fc-fusion protein thereby forming a first modified antibody, a first modified antibody fragment, or a first modified Fc-fusion protein;
d) providing a first activating molecule comprising a first crosslinking group, a first reactive group, and optionally a linker;
e) contacting the first modified antibody, first modified antibody fragment, or first modified Fc-fusion protein with the first activating molecule, wherein the first activating molecule attaches to the first modified antibody, first modified antibody fragment, or first Fc-fusion protein at the first chemical handle, thereby forming a first activated antibody, first activated antibody fragment or first activated Fc-fusion protein;
f) providing:
  iv) a second antibody comprising a terminal GlcNAc residue,
  v) a second antibody fragment comprising a terminal GlcNAc residue, or
  vi) a second Fc-fusion protein comprising a terminal GlcNAc residue;
g) providing a second modified sugar comprising a second chemical handle;
h) contacting the second antibody, second antibody fragment or second Fc-fusion protein with the second modified sugar and the glycosyl transferase enzyme, wherein the glycosyl transferase enzyme catalyzes the attachment of the second modified sugar to the terminal GlcNAc residue of the second antibody thereby forming a second modified antibody, a second modified antibody fragment, or a second modified Fc-fusion protein;
i) providing a second activating molecule comprising a second crosslinking group, a second reactive group and optionally, a linker;
j) contacting the second modified antibody, second modified antibody fragment, or second modified Fc-fusion protein with the second activating molecule, wherein the second activating molecule attaches to the second modified antibody, second modified antibody fragment, or second modified Fc-fusion protein at the second chemical handle, thereby forming a second activated antibody, a second activated antibody fragment, or a second modified Fc-fusion protein;
k) contacting the first activated antibody, first activated antibody fragment, or first activated Fc-fusion protein with the second activated antibody, second activated antibody fragment, or second activated Fc-fusion protein, wherein the first crosslinking group of the first activated antibody, first activated antibody fragment, or first activated Fc-fusion protein reacts with the second crosslinking group of the second activated antibody, second activated antibody fragment, or second activated Fc-fusion protein, thereby forming the bispecific antibody or antibody conjugate; and
l) analyzing the bispecific antibodies or antibody conjugates for functionality.

In certain embodiments, methods are provided for making bispecific antibodies or antibody conjugates, the methods comprising:
a) providing a first activated antibody, first activated antibody fragment, or first activated Fc-fusion protein comprising a first activating molecule comprising a first crosslinking group, a first reactive group and optionally, a linker;
b) providing a second activated antibody, second activated antibody fragment, or second activated Fc-fusion protein comprising a second activating molecule comprising a second crosslinking group, a second reactive group and optionally, a linker;
c) contacting the first activated antibody, first activated antibody fragment, or first activated Fc-fusion protein with the second activated antibody, second activated antibody fragment, or second activated Fc-fusion protein, wherein the first crosslinking group of the first activated antibody, first activated antibody fragment, or first activated Fc-fusion protein reacts with the second crosslinking group of the second activated antibody, second activated antibody fragment, or second activated Fc-fusion protein, thereby forming the bispecific antibody or antibody conjugate; and
d) analyzing the bispecific antibodies or antibody conjugates for functionality.

In certain embodiments, the bispecific antibodies or antibody conjugates are analyzed by gel electrophoresis. In certain embodiments, the bispecific antibodies or antibody conjugates are analyzed by fluorescence microscopy. In certain embodiments, the bispecific antibodies or antibody conjugates are analyzed by mass spectroscopy.

Certain embodiments provide for methods of treating a disease, disorder or condition in a subject in need thereof comprising administering the bispecific antibodies provided herein, the antibody conjugates provided herein, the pharmaceutical compositions provided herein, the antibody-conjugated liposomes provided herein, the antibody-conjugated mRNAs or antibody-conjugated siRNAs provided herein. In certain embodiments, the bispecific antibody, antibody conjugate, pharmaceutical composition, antibody-conjugated liposome, antibody-conjugated mRNA or antibody-conjugated siRNA is administered by parenteral administration comprising intravenous administration, subcutaneous administration, intraperitoneal administration, intramuscular administration, intravascular administration, intrathecal administration, intravitreal administration, or infusion. In certain embodiments, the bispecific antibody, antibody conjugate, pharmaceutical composition, antibody-conjugated liposome, antibody-conjugated mRNA or antibody-conjugated siRNA is administered by a microneedle device. In certain embodiments, the bispecific antibody, antibody conjugate, pharmaceutical composition, antibody-conjugated liposome, antibody-conjugated mRNA or antibody-conjugated siRNA is administered by topical, oral or nasal administration. In certain embodiments, the disease is a cancer, a pathogenic infection, an inflammatory disease, an autoimmune disease or a metabolic disease. In certain embodiments, the subject is a mammal. In certain embodiments, the antibody conjugate is an antibody-Fc protein scaffold conjugate.

Certain embodiments provide for methods of diagnosing a disease, disorder or condition using the bispecific antibodies, antibody conjugate, pharmaceutical compositions, antibody-conjugated liposomes, antibody-conjugated mRNA or antibody-conjugated siRNA provided herein. In certain embodiments, the antibody conjugate is an antibody-Fc protein scaffold conjugate.

In certain embodiments, methods for diagnosing a disease, disorder or condition in a subject are provided, the methods comprising:
 (a) contacting a sample obtained from a subject suspected of having the disease with a bispecific antibody provided herein, an antibody conjugate provided herein, a pharmaceutical composition provided herein, an antibody-conjugated liposome provided herein, an antibody-conjugated mRNA or an antibody-conjugated siRNA provided herein to form a contacted sample;
 (b) incubating the contacted sample for an appropriate amount of time to form an incubated sample;
 (c) illuminating the incubated sample with an appropriate wavelength to form an illuminated sample; and
 (d) detecting fluorescent emissions from the illuminated sample;
 wherein the fluorescent emissions are used to diagnose or detect the disease.

Certain embodiments provide for the use of any of the methods, compositions or kits disclosed herein for the diagnosis of diseases, for example, cancer, including but not limited to breast cancer, prostate cancer, lung cancer, skin cancer, cancers of the reproductive tract, brain cancer, liver cancer, pancreatic cancer, stomach cancer, blood cancers (e.g., leukemia and lymphoma), sarcomas, melanomas, and the like.

Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis.

In some instances, the cancer is a lung cancer. Lung cancer may start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

In some instances, the cancer is a breast cancer. In some instances, the breast cancer is estrogen receptor positive, progesterone receptor positive and Her2 positive (triple positive). In some instances, the breast cancer is estrogen receptor negative, progesterone receptor negative and Her2 negative (triple negative). In some instances, the breast cancer is estrogen receptor positive and Her2 positive. In some instances, the breast cancer is estrogen receptor positive and Her 2 negative. In some instances, the breast cancer is estrogen receptor negative and Her2 positive. In some instances, the breast cancer is metastatic.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma.

Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The leukemia may be an acute lymphocytic leukemia, acute lymphoblastic leukemia, acute myelocytic leukemia, chronic lymphocytic leukemia, or chronic myelocytic leukemia. Additional types of leukemias include hairy cell leukemia, chronic myelomonocytic leukemia, B-cell chronic lymphocytic leukemia and juvenile myelomonocytic leukemia.

Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenstrom macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

The one or more diseases or conditions may be a pathogenic infection. Pathogenic infections may be caused by one or more pathogens. In some instances, the pathogen is a bacterium, fungi, virus, or protozoan.

Exemplary pathogens include but are not limited to: *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* or *Yersinia*. In some cases, the disease or condition caused by the pathogen is tuberculosis and the heterogeneous sample comprises foreign molecules derived from the bacterium *Mycobacterium tuberculosis* and molecules derived from the subject. In some instances, the disease or condition is caused by a bacterium is tuberculosis, pneumonia, which may be caused by bacteria such as *Streptococcus* and *Pseudomonas*, a foodborne illness, which may be caused by bacteria such as *Shigella, Campylobacter* and *Salmonella*, and an infection such as tetanus, typhoid fever, diphtheria, syphilis and leprosy. The disease or condition may be bacterial vaginosis, a disease of the vagina caused by an imbalance of naturally occurring bacterial flora. Alternatively, the disease or condition is a bacterial meningitis, a bacterial inflammation of the meninges (e.g., the protective membranes covering the brain and spinal cord). Other diseases or conditions caused by bacteria include, but are not limited to, bacterial pneumonia, a urinary tract infection, bacterial gastroenteritis, and bacterial skin infection. Examples of bacterial skin infections include, but are not limited to, impetigo which may be caused by *Staphylococcus aureus* or *Streptococcus pyrogenes*; erysipelas which may be caused by a *streptococcus* bacterial infection of the deep epidermis with lymphatic spread; and cellulitis which may be caused by normal skin flora or by exogenous bacteria.

The pathogen may be a fungus, such as, *Candida, Aspergillus, Cryptococcus, Histoplasma, Pneumocystis,* and *Stachybotrys*. Examples of diseases or conditions caused by a fungus include, but are not limited to, jock itch, yeast infection, ringworm, and athlete's foot.

The pathogen may be a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The pathogen may be a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B. connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), *Giardia* (e.g., *G. lamblia*), *Isospora* (e.g., *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

The disease or condition may be an autoimmune disease or autoimmune related disease. An autoimmune disorder may be a malfunction of the body's immune system that causes the body to attack its own tissues. Examples of autoimmune diseases and autoimmune related diseases include, but are not limited to, Addison's disease, alopecia areata, ankylosing spondylitis, antiphospholipid syndrome (APS), autoimmune aplastic anemia, autoimmune hemolytic anemia, autoimmune hepatitis, autoimmune myocarditis, Behcet's disease, celiac sprue, Crohn's disease, dermatomyositis, eosinophilic fasciitis, erythema nodosum, giant cell arteritis (temporal arteritis), Goodpasture's syndrome, Graves' disease, Hashimoto's disease, idiopathic thrombocytopenic purpura (ITP), IgA nephropathy, juvenile arthritis, diabetes, juvenile diabetes, Kawasaki syndrome, Lambert-Eaton syndrome, lupus (SLE), mixed connective tissue disease (MCTD), multiple sclerosis, myasthenia gravis, pemphigus, polyarteritis *nodosa*, type I, II, & III autoimmune polyglandular syndromes, polymyalgia rheumatica, polymyositis, psoriasis, psoriatic arthritis, Reiter's syndrome, relapsing polychondritis, rheumatoid arthritis, sarcoidosis, scleroderma, Sjogren's syndrome, sperm & testicular autoimmunity, stiff person syndrome, Takayasu's arteritis, temporal arteritis/giant cell arteritis, ulcerative colitis, uveitis, vasculitis, vitiligo, and Wegener's granulomatosis.

The disease or condition may be an inflammatory disease. Examples of inflammatory diseases include, but are not limited to, alveolitis, amyloidosis, angiitis, ankylosing spondylitis, avascular necrosis, Basedow's disease, Bell's palsy, bursitis, carpal tunnel syndrome, celiac disease, cholangitis, chondromalacia patella, chronic active hepatitis, chronic fatigue syndrome, Cogan's syndrome, congenital hip dysplasia, costochondritis, Crohn's Disease, cystic fibrosis, De Quervain's tendinitis, diabetes associated arthritis, diffuse idiopathic skeletal hyperostosis, discoid lupus, Ehlers-Danlos syndrome, familial mediterranean fever, fascitis, fibrositis/fibromyalgia, frozen shoulder, ganglion cysts, giant cell arteritis, gout, Graves' Disease, HIV-associated rheumatic disease syndromes, hyperparathyroid associated arthritis, infectious arthritis, inflammatory bowel syndrome/irritable bowel syndrome, juvenile rheumatoid arthritis, Lyme disease, Marfan's Syndrome, Mikulicz's Disease, mixed connective tissue disease, multiple sclerosis, myofascial pain syndrome, osteoarthritis, osteomalacia, osteoporosis and corticosteroid-induced osteoporosis, Paget's Disease, palindromic rheumatism, Parkinson's Disease, Plummer's Disease, polymyalgia rheumatica, polymyositis, pseudogout, psoriatic arthritis, Raynaud's Phenomenon/Syndrome, Reiter's Syndrome, rheumatic fever, rheumatoid arthritis, sarcoidosis, sciatica (lumbar radiculopathy), scleroderma, scurvy, sickle cell arthritis, Sjogren's Syndrome, spinal stenosis, spondyloisthesis, Still's Disease, systemic lupus erythematosis, Takayasu's (Pulseless) Disease, Tendinitis, tennis elbow/golf elbow, thyroid associated arthritis, trigger finger, ulcerative colitis, Wegener's Granulomatosis, and Whipple's Disease.

Certain embodiments provide for the use of bispecific antibodies, antibody conjugates, pharmaceutical compositions, antibody-conjugated liposomes or antibody-conjugated mRNA or siRNA disclosed herein for the manufacture of a diagnostic product, a kit and/or a pharmaceutical preparation for the treatment or diagnosis of a mammal in need thereof. Certain embodiments provide for the use of bispecific antibodies, antibody conjugates, pharmaceutical compositions, antibody-conjugated liposomes, antibody-conjugated mRNA or antibody-conjugated siRNA disclosed herein for the manufacture of a pharmaceutical composition for the treatment of a tumor or infectious disease in a mammal. In certain embodiments, the antibody conjugate is an antibody-Fc protein scaffold conjugate.

A detailed description of the present teachings having been provided above, the following examples are given for the purpose of illustrating the present teachings and shall not be construed as being a limitation on the scope of the invention or claims.

The following examples are intended to illustrate but not limit the present disclosure.

EXAMPLES

Example 1: Crosslinking Two Antibodies

Antibodies were treated with either beta-galactosidase or Endo S to remove terminal galactose residues or to cleave the chitobiose core, respectively. After incubation, GalT (Y289L) enzyme, UDP-GalNAz, and $MnCl_2$ were added. The reaction mixtures were incubated overnight, and the azide-activated antibodies were buffer exchanged in Amicon 50 kD cut-off spin filters to remove excess UDP-GalNAz. The azide-activated antibodies were then reacted with dibenzocyclooctyne (DIBO)-functionalized tetrazine (TZN) or trans-cyclooctene (TCO) in an overnight reaction (TCO-PEG 12-DBCO, and Tetrazine-DBCO purchased from Broadpharm Cat #s BP-22423 and BP-22445). PEG 12 indicates the linker comprises 12 PEG groups. After removal of excess DIBO reagents using the 50 kD spin filters, the antibody pairs with either TCO or tetrazine were combined and allowed to react. Samples were removed at various times to analyze crosslinked products by gel electrophoresis.

Proof-of-principle experiments demonstrated the production of crosslinked antibody pairs which included HERCEPTIN® (trastuzumab) antibody—ERBITUX® (cetuximab) antibody, HERCEPTIN® (trastuzumab) antibody—HERCEPTIN® (trastuzumab) antibody, and ERBITUX® (cetuximab) antibody—ERBITUX® (cetuximab) antibody combinations. Each antibody was labeled with TCO or tetrazine and each was combined with its respective partner moiety and incubated over a time course. Gel analysis results showed the formation of antibody pairs of the expected weights of ~300 kD on non-reducing gels and heavy chain pairs of 100 kD on reducing gels.

Figure 6:
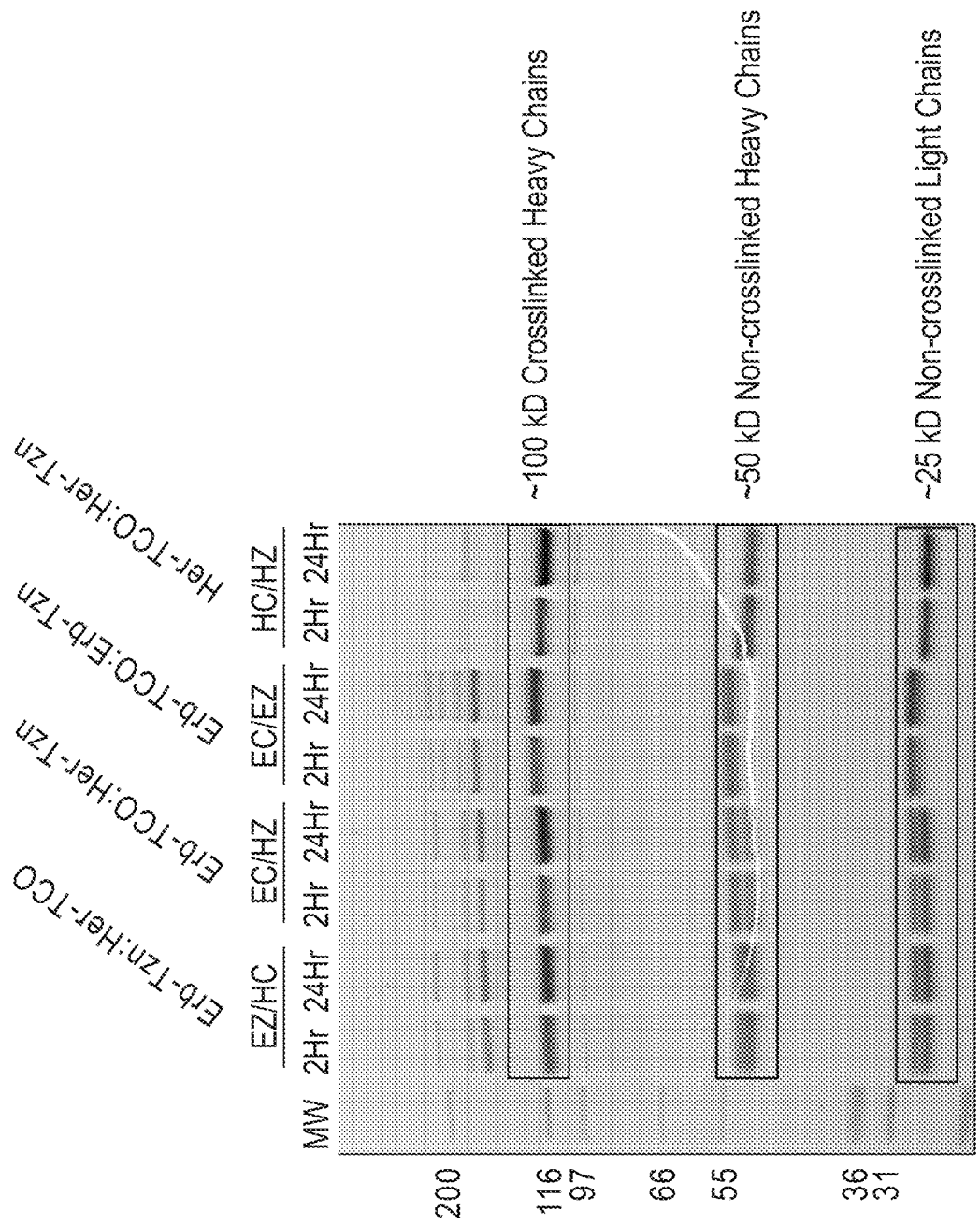
FIG. 6: A reducing gel showing the reaction products for the following crosslinked antibody reactions after 2 hours and 24 hours: 1) tetrazine-activated ERBITUX® (cetuximab) antibody (EZ) with trans-cyclooctene-activated HERCEPTIN® (trastuzumab) antibody (HC) to form the crosslinked antibody Erb-Tzn:Her-TCO; 2) TCO-activated activated ERBITUX® (cetuximab) antibody (EC) with Tzn-activated HERCEPTIN® (trastuzumab) antibody (HZ) to form the crosslinked antibody Erb-TCO:Her-Tzn; 3) TCO-activated ERBITUX® (cetuximab) antibody (EC) with Tzn-activated ERBITUX® (cetuximab) antibody (EZ) to form the crosslinked antibody Erb-TCO:Erb-Tzn; and 4) TCO-activated HERCEPTIN® (trastuzumab) antibody (HC) with Tzn-activated HERCEPTIN® (trastuzumab) antibody (HZ) to form the crosslinked antibody Her-TCO:Her-Tzn. For gel analysis, crosslinked antibodies were dissolved in sample prep buffer with 100 mM DTT as a reducing agent and then heated at 70° C. for 15 mins. Antibodies were applied to NuPAGE 4-12% Bis-Tris gels and run in MOPS buffer. Gels were stained with SYPRO® Ruby total protein gel stain and then imaged on a FUJI FLA9000 fluorescence imager. The bands at ~100 kD represent crosslinked heavy chains, the bands at ~50 kD represent non-crosslinked heavy chains, and the bands at ~25 kD represent non-crosslinked light chains.

FIG. 6 shows a reducing gel showing the reaction products for the following cross-linked antibody reactions after 2 hours and 24 hours: 1) tetrazine-activated ERBITUX® (cetuximab) antibody with trans-cyclooctene-activated HERCEPTIN® (trastuzumab) antibody (Erb-Tzn:Her-TCO); 2) TCO-activated ERBITUX® (cetuximab) antibody with Tzn-activated HERCEPTIN® (trastuzumab) antibody (Erb-TCO:Her-Tzn); 3) TCO-activated ERBITUX® (cetuximab) antibody with Tzn-activated ERBITUX® (cetuximab) antibody (Erb-TCO:Erb-Tzn); and 4) TCO-activated HERCEPTIN® (trastuzumab) antibody with Tzn-activated HERCEPTIN® (trastuzumab) antibody (Her-TCO:Her-Tzn), For gel analysis, cross-linked antibodies were dissolved in sample prep buffer with 100 mM DTT as a reducing agent and then heated at 70° C. for 15 mins. Antibodies were applied to NuPAGE 4-12% Bis-Tris gels and run in MOPS buffer. Gels were stained with SYPRO® Ruby total protein gel stain and then imaged on a FUJI FLA9000 fluorescence imager. The bands at ~100 kD represent crosslinked heavy chains, the bands at ~50 kD represent non-crosslinked heavy chains, and the bands at ~25 kD represent non-crosslinked light chains.

Figure 7:
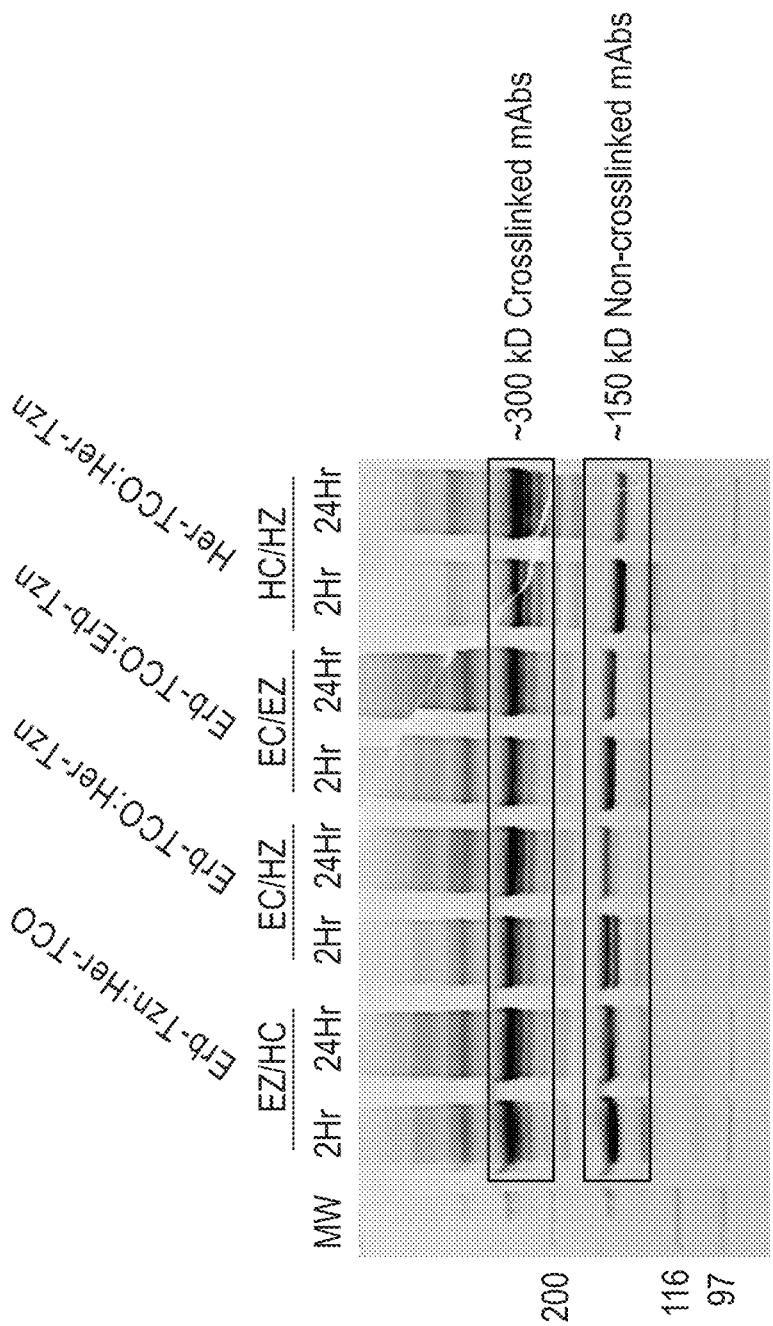
FIG. 7: A non-reducing gel showing the reaction products for the following crosslinked antibody reactions after 2 hours and 24 hours: 1) tetrazine-activated ERBITUX® (cetuximab) antibody with trans-cyclooctene-activated HERCEPTIN® (trastuzumab) antibody (Erb-Tzn:Her-TCO); 2) TCO-activated ERBITUX® (cetuximab) antibody with Tzn-activated HERCEPTIN® (trastuzumab) antibody (Erb-TCO:Her-Tzn); 3) TCO-activated ERBITUX® (cetuximab) antibody with Tzn-activated ERBITUX® (cetuximab) antibody (Erb-TCO:Erb-Tzn); and 4) TCO-activated HERCEPTIN® (trastuzumab) antibody with Tzn-activated HERCEPTIN® (trastuzumab) antibody (Her-TCO:Her-Tzn). For gel analysis, cross-linked antibodies were dissolved in sample prep buffer without DTT and then heated at 70° C. for 15 mins. Antibodies were applied to NuPAGE 4-12% Bis-Tris gels and run in MOPS buffer. Gels were stained with SYPRO® Ruby total protein gel stain and then imaged on a FUJI FLA9000 fluorescence imager. The bands at ~300 kD represent crosslinked antibodies (mAbs) and the bands at ~150 kD represent non-crosslinked antibodies (mAbs).

FIG. 7 shows a non-reducing gel showing the reaction products for the following cross-linked antibody reactions after 2 hours and 24 hours: 1) tetrazine-activated ERBITUX® (cetuximab) antibody with trans-cyclooctene-activated HERCEPTIN® (trastuzumab) antibody (Erb-Tzn:Her-TCO); 2) TCO-activated ERBITUX® (cetuximab) antibody with Tzn-activated HERCEPTIN® (trastuzumab) antibody (Erb-TCO:Her-Tzn); 3) TCO-activated ERBITUX® (cetuximab) antibody with Tzn-activated ERBITUX® (cetuximab) antibody (Erb-TCO:Erb-Tzn); and 4) TCO-activated HERCEPTIN® (trastuzumab) antibody with Tzn-activated HERCEPTIN® (trastuzumab) antibody (Her-TCO:Her-Tzn), For gel analysis, cross-linked antibodies were dissolved in sample prep buffer without DTT and then heated at 70° C. for 15 mins. Antibodies were applied to NuPAGE 4-12% Bis-Tris gels and run in MOPS buffer. Gels were stained with SYPRO® Ruby total protein gel stain and then imaged on a FUJI FLA9000 fluorescence imager. The bands at ~300 kD represent crosslinked antibodies (mAbs) and the bands at ~150 kD represent non-crosslinked antibodies (mAbs).

Example 2: Crosslinking Four Antibodies

Antibodies were prepared as described previously in Example 1.

Figure 8:
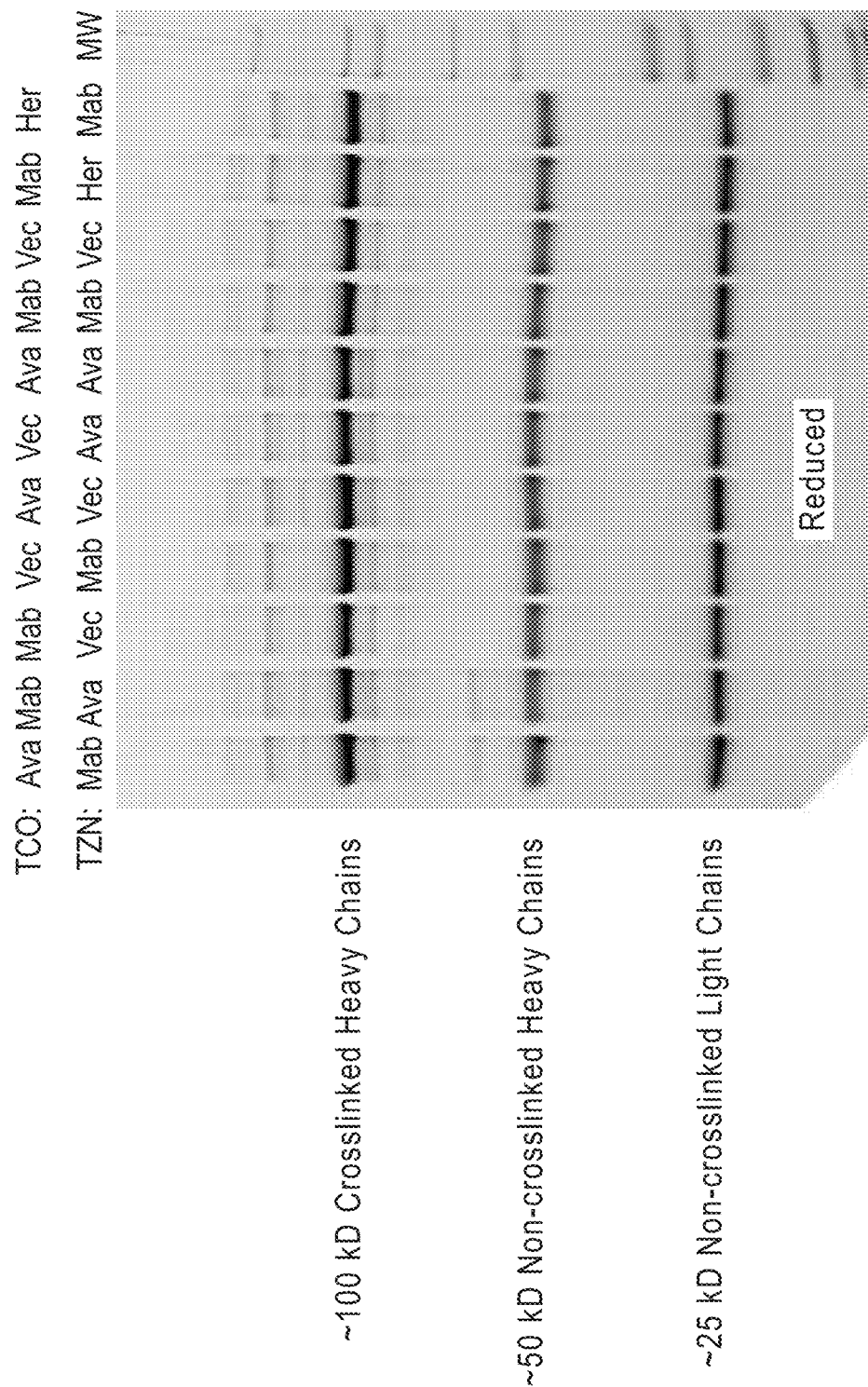
FIG. 8: A reducing gel showing the reaction products from crosslinked antibody reactions after an 18 hour incubation. The antibodies, AVASTIN® (bevacizumab) antibody (Ava), MABTHERA® (rituximab) antibody (Mab), VECTIBIX® (panitumumab) antibody (Vec), and HERCEPTIN® (trastuzumab) antibody (Her) were treated with Endo S2 enzyme and then azide-activated with GalT(Y289L) and UDP-GalNAz substrate. All antibodies were then labeled with either DIBO-PEG12-TCO or DIBO-tetrazine and then combined for conjugation in the combinations shown (PEG12 indicates a linker comprising 12 PEG groups). For gel analysis, crosslinked antibodies were dissolved in sample prep buffer with 100 mM DTT as a reducing agent and then heated at 70° C. for 15 mins. Antibodies were applied to NuPAGE 4-12% Bis-Tris gels and run in MOPS buffer. Gels were stained with SYPRO® Ruby total protein gel stain and then imaged on a FUJI FLA9000 fluorescence imager. The bands at ~100 kD represent crosslinked heavy chains, the bands at ~50 kD represent non-crosslinked heavy chains, and the bands at ~25 kD represent non-crosslinked light chains.

FIG. 8 is a reducing gel showing the reaction products from cross-linked antibody reactions after an 18 hour incubation. The antibodies, AVASTIN® (bevacizumab) antibody (Ava), MABTHERA® (rituximab) antibody (Mab), VECTIBIX® (panitumumab) antibody (Vec), and HERCEPTIN® (trastuzumab) antibody (Her) were treated with Endo S2 enzyme and then azide-activated with GalT (Y289L) and UDP-GalNAz substrate. All antibodies were then labeled with either DIBO-PEG12-TCO or DIBO-tetrazine and then combined for conjugation in the combinations shown. For gel analysis, cross-linked antibodies were dissolved in sample prep buffer with 100 mM DTT as a reducing agent and then heated at 70° C. for 15 mins. Antibodies were applied to NuPAGE 4-12% Bis-Tris gels and run in MOPS buffer. Gels were stained with SYPRO® Ruby total protein gel stain and then imaged on a FUJI FLA9000 fluorescence imager. The bands at ~100 kD represent crosslinked heavy chains, the bands at ~50 kD represent non-crosslinked heavy chains, and the bands at ~25 kD represent non-crosslinked light chains.

Figure 9:
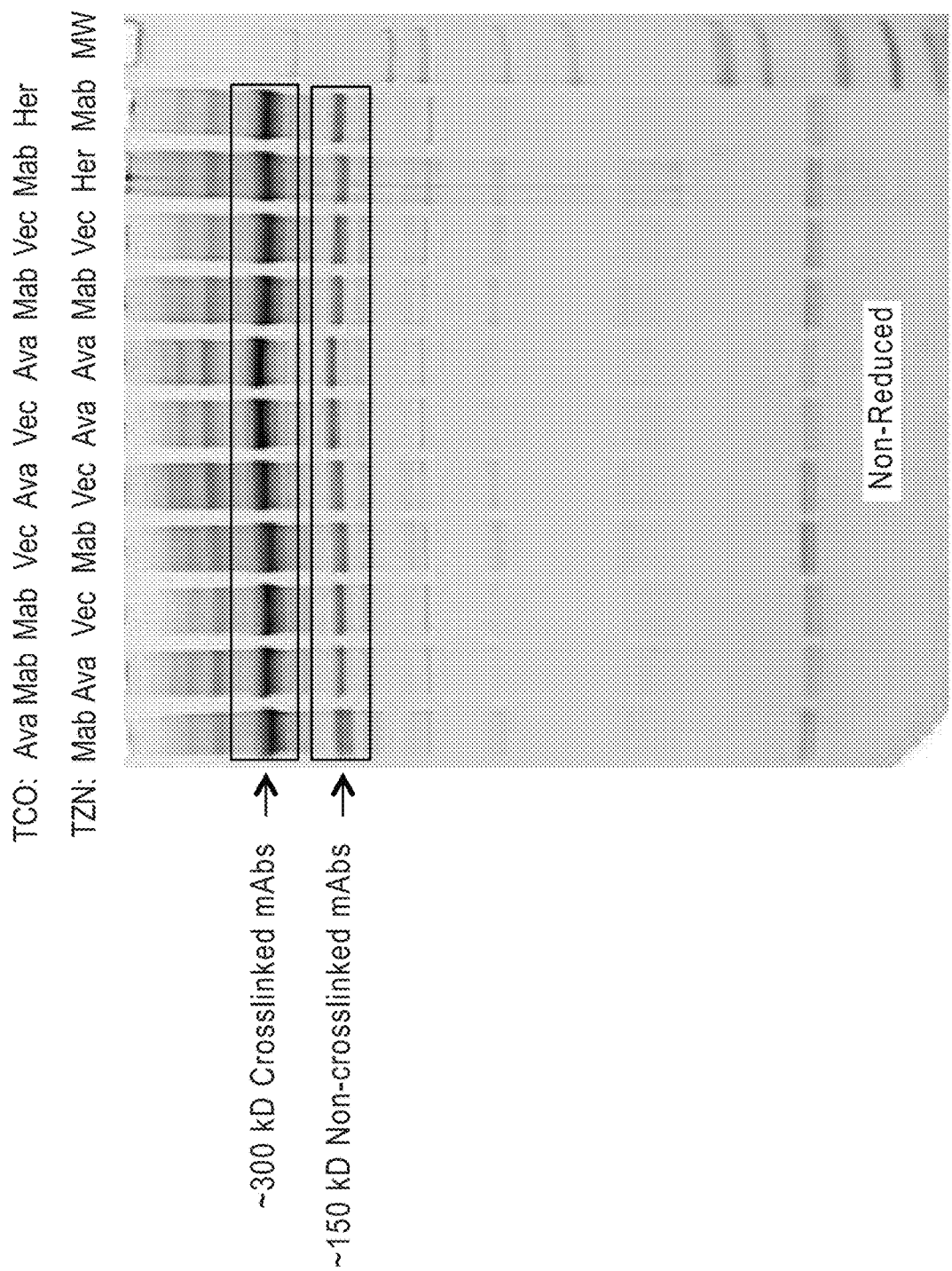
FIG. 9: A non-reducing gel showing the reaction products from crosslinked antibody reactions after an 18 hour incubation. The antibodies, AVASTIN® (bevacizumab) antibody (Ava), MABTHERA® (rituximab) antibody (Mab), VECTIBIX® (panitumumab) antibody (Vec), and HERCEPTIN® (trastuzumab) antibody (Her) were treated with Endo S2 enzyme and then azide-activated with GalT (Y289L) and UDP-GalNAz substrate. All antibodies were then labeled with either DIBO-PEG12-TCO or DIBO-tetrazine and then combined for conjugation in the combinations shown. For gel analysis, cross-linked antibodies were dissolved in sample prep buffer without DTT as a reducing agent and then heated at 70° C. for 15 mins. Antibodies were applied to NuPAGE 4-12% Bis-Tris gels and run in MOPS buffer. Gels were stained with SYPRO® Ruby total protein gel stain and then imaged on a FUJI FLA9000 fluorescence imager. The bands at ~300 kD represent crosslinked antibodies (mAbs) and the bands at ~150 kD represent non-crosslinked antibodies (mAbs).

FIG. 9 is a non-reducing gel showing the reaction products from cross-linked antibody reactions after an 18 hour incubation. The antibodies, AVASTIN® (bevacizumab) antibody (Ava), MABTHERA® (rituximab) antibody (Mab), VECTIBIX® (panitumumab) antibody (Vec), and HERCEPTIN® (trastuzumab) antibody (Her) were treated with Endo S2 enzyme and then azide-activated with GalT (Y289L) and UDP-GalNAz substrate. All antibodies were then labeled with either DIBO-PEG12-TCO or DIBO-tetrazine and then combined for conjugation in the combinations shown. For gel analysis, cross-linked antibodies were dissolved in sample prep buffer without DTT as a reducing agent and then heated at 70° C. for 15 mins. Antibodies were applied to NuPAGE 4-12% Bis-Tris gels and run in MOPS buffer. Gels were stained with SYPRO® Ruby total protein gel stain and then imaged on a FUJI FLA9000 fluorescence imager. The bands at ~300 kD represent crosslinked antibodies (mAbs) and the bands at ~150 kD represent non-crosslinked antibodies (mAbs).

Example 3: Reproducibility of Antibody Modification without Optimization of Labeling Using the Method Outlined in FIG. 1

The antibodies listed in Table 2 were labeled over a period of 3 years by multiple different operators. In all cases, the β-galactosidase-cleaved azide-activated antibodies were labeled with DIBO-Dye-488 and the DOLs were quantitated as described in the "Materials and Methods" section of Example 4. The average DOL without any optimization of labeling was 3.4 dyes per antibody with less than 10% variability (Average DOL=3.4+/−0.3).

TABLE 2

| Antibody Species | Isotype | Target | DOL |
| --- | --- | --- | --- |
| human monoclonal/Erbitux | IgG1 | EGFR | 3.6 n = 10 |
| human monoclonal/Trastuzumab | IgG1 | HER2/neu | 3.5 n = 12 |
| human monoclonal/6C12-H10 | IgG3 | Lymphoma cell | 3.1 |
| human monoclonal | IgG1 | sLea | 3.0 |
| human monoclonal | IgG1 | GD2 | 3.2 |
| human monoclonal | IgG1 | GD2 | 4.8 |
| human monoclonal | IgG1 | GD2 | 3.4 |
| human monoclonal | IgG1 | GM2 | 3.3 |
| human monoclonal | IgG3 | GD3 | 3.4 |
| human monoclonal | IgG3 | sLea | 3.3 |
| human monoclonal | IgG3 | f-GM1 | 3.0 |
| human monoclonal | IgG3 | Tn | 3.1 |
| human monoclonal | IgG3 | GD3 | 3.5 |
| human monoclonal | IgG1 | J591 | 2.7 n = 3 |
| mouse monoclonal | IgG1 | GD2 | 3.2 |
| mouse monoclonal S3.5 | IgG2a | CD4 | 3.4 n = 10 |
| mouse monoclonal 2-28-33 | IgG1 | β-tubulin | 3.4 n = 3 |
| mouse monoclonal HIT3a | IgG2a | CD3 | 3.0 |
| mouse monoclonal 3B5 | IgG2a | CD8 | 3.7 |
| mouse monoclonal HIT8a | IgG1 | CD8a | 3.7 |
| mouse monoclonal HI30 | IgG1 | CD45 | 3.2 |

TABLE 2-continued

| Antibody Species | Isotype | Target | DOL |
| --- | --- | --- | --- |
| mouse monoclonal | IgG2a | CD56 | 3.0 |
| mouse monoclonal | IgG1 | C3b, iC3b | 3.8 |
| mouse monoclonal | IgG2a | C3b, iC3b, C3dg | 3.6 |
| mouse monoclonal | IgG1 | Interferon-γ | 3.4 |
| goat polyclonal IgG | polyclonal | Apolipoprotein-A2 | 3.4 |

Example 4: Crosslinking of Antibodies and Antibody Fragments

Described herein is a rapid and efficient method for the site-specific, directional, crosslinking of essentially any two existing antibodies or antibody fragments yielding the desired tetravalent bispecific species. The directional, site-specific method disclosed herein preserves antigen binding affinity and ensures the directionality of conjugation. The method described in this example involves three main steps. First, the Fc domain antibody glycans were cleaved with endoglycosidase S2 (EndoS2) leaving single core GlcNAc residues at the core mAb glycosylation sites. Second, the core GlcNAcs were azide-modified with a mutant GalT (Y289L) enzyme that efficiently transferred a galactose-azide sugar onto the GlcNAc residues. This step imparts site-selectivity to the crosslinking process. Third, each of the antibodies in a pair was activated with one of two Diels Alder orthogonal reactive-pair functional groups, transcyclooctyne (TCO) or methytetrazine (Tzn). This step imparts directionality to the mAb crosslinking process preventing the formation of highly cross-linked and unwanted high molecular weight species. Once the antibodies were activated, the TCO/Tzn mAb pairs were mixed and matched in equal molar amounts to yield site-specific, directionally conjugated, tetrameric bispecific pairs.

Materials and Methods:
Enzymatic Labeling:

In a one-pot activation reaction, antibodies were incubated for 5 hours at 37° C. with β-(1-4) galactosidase (Prozyme) or for 1 hour at 37° C. with immobilized-EndoS2 (GlycINATOR, Genovis), then UDP-GalNAz substrate, β-Gal-T1(Y289L) enzyme, and $MnCl_2$ were added, and the mixture was incubated overnight (ON) in non-phosphate buffer (pH 7.4) at 30° C. Excess UDP-GalNAz and β-Gal-T 1(Y289L) were removed using 50 kD MW cut-off Amicon ULTRA spin filters. The purified azide-activated antibodies were labeled with dibenzocyclooctyne (DIBO)-Alexa Fluor™ 488 (Dye-488), DIBO-Biotin, DIBO-vc-MMAE, or DIBO-DFO, for ON (16 hrs) at 20° C. For bispecific antibody production, the azide-activated antibodies were incubated with DBCO-PEG-transcyclooctyne (TCO) or DBCO-PEG-methyltetrazine (Tzn) (Click Chemistry Tools, Broadpharm; PEG12 or PEG4 versions) ON for 12 hours at 24° C. The antibodies were purified and site-specific cross-linking was performed by combining equal amounts of each TCO-Tzn pair and incubating ON at 30° C.

Generation of Fluorescent-Activated Human IgG1 (hIgG1) Fc Protein: The hIgG1 Fc protein (Acro Biosystems) was azide-modified as described above, buffer exchanged into PBS using 10 kD MW cut-off spin columns, and incubated with DBCO-TCO or -Tzn PEG compounds ON at 24° C. After 12 hours, 1M Na Bicarbonate, pH 8.3, was added to the reaction (100 mM final) and Dye-488-succinimidyl ester (Dye-488-SE) (Thermo Fisher) was added in 2 fold excess of protein (m/m) and incubated at RT for 1 hour. The reaction was stopped by buffer exchange into TBS using 10 kD cut-off filters with 5 washes.

Generation of F(Ab')₂ and scFc Fragments: Antibodies were cleaved using FragIT MicroSpin columns (Genovis) to generate F(ab')₂ and scFc fragments. All antibody samples, cleaved and non-cleaved, were exhaustively dialyzed into 50 mM ammonium acetate buffer (pH 6.0) and then dried in the speed vac for downstream mass spectroscopic (MS) analyses.

Gel and Spectroscopic Analyses: For gel analyses, antibodies were applied to NuPAGE 4-12% Bis-Tris gels and run in MOPS buffer. Gels were imaged on the FUJI FLA9000 imager and then post-stained with SYPRO® Ruby total protein gel stain and imaged again on the FUJI FLA9000 imager. The degree of labeling (DOL) of the antibodies was determined by absorbance calculations of the final purified fluorescent conjugates using protein concentrations and molar extinction coefficients, or by fluorometric gel image analysis of the conjugates using known fluorescent standards with normalization to total protein.

LC/MS: LC/MS Analysis: Intact and fragment samples were separated and analyzed on Thermo Scientific™ Dionex™ UltiMate™ 3000 BioRS system coupled to Thermo Scientific™ Orbitrap Fusion™ Lumos Tribrid MS instrument, using a Thermo Scientific™ MAbPac™ RP analytical column, 4.0 m, 2.1×50 mm column (p/n 088648) and H₂O/TFA/acetonitrile mobile phase at 80° C. The MS acquisition method was set with a full scan at both 15,000 (FWHM, at m/z 200) and 120,000 resolution in positive mode. The method parameters were: AGC 2e⁵, IT 200 ms, in-source CID 0 ev and 35 ev, scan range: 800-3000, 1000-3500 m/z, spray voltage 3.8 kv, sheath gas 60, aux gas 20, capillary temperature 350C, s-lens 30, probe heater temperature 150° C.

Results:

The results demonstrated the production of multiple bispecific antibody pairs using different preexisting therapeutic antibodies and the NIST monoclonal antibody standard (NIST mAb) as a model for development. Mass spectroscopic and enzymatic analyses of the labeled antibodies confirmed the site specific cross-linking sites were limited to the antibody Fc domain glycosylation sites. Gel analyses demonstrated a high yield of the desired tetravalent bispecific species (greater than 80% yield without purification) that could then be further screened for binding and physiological efficacy. The results also demonstrated the production of a NIST mAb site-specifically crosslinked to an antibody fragment, an IgG1 Fc protein, that was used as a scaffold for site-specific payload attachment.

Figure 10:
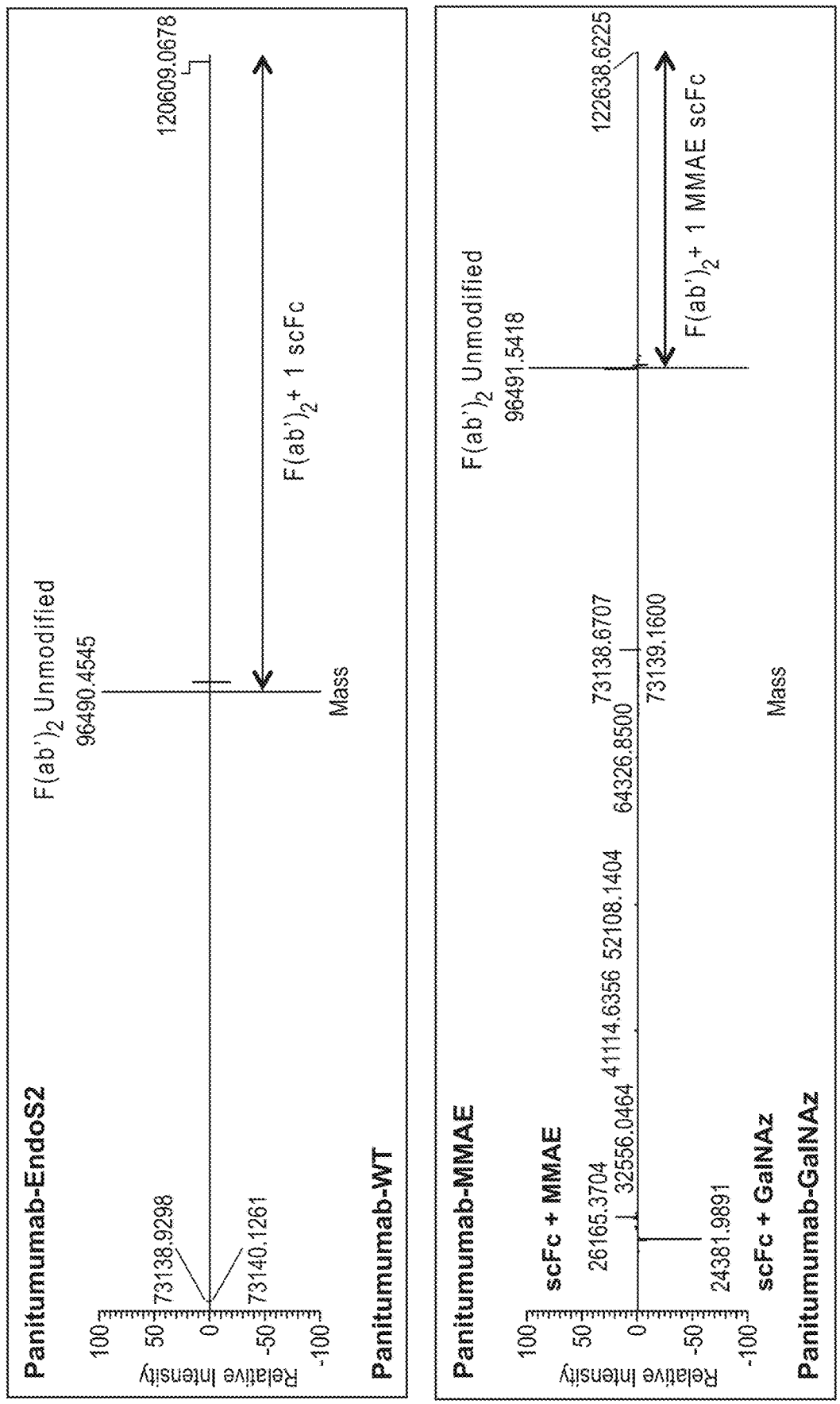
FIG. 10: LCMS analysis of panitumumab F(ab')$_2$ fragments after EndoS2 and site-specific labeling with GalT (Y289L) enzyme demonstrating that the F(ab')$_2$ fragments remain unaltered. Comparison of the wild type (WT) F(ab')$_2$ fragments with the EndoS2-cleaved, azide-activated (top panel), and vc-MMAE-conjugated forms (bottom panel) showed no difference in the respective F(ab')$_2$ fragments masses, demonstrating that the conjugation method leaves the antigen binding domains unaltered.

As shown in FIG. 10, after EndoS2 cleavage and site-specific labeling with GalT(Y298L) enzyme, panitumumab F(ab')₂ fragments remained completely unaltered. Comparison of the Wild Type (WT) F(ab')₂ fragments with the EndoS2-cleaved, azide-activated (top), and vc-MMAE-conjugated forms (bottom) showed no difference in the respective F(ab')₂ fragments masses, demonstrating that the conjugation method leaves the antigen binding domains unaltered.

Figure 11:
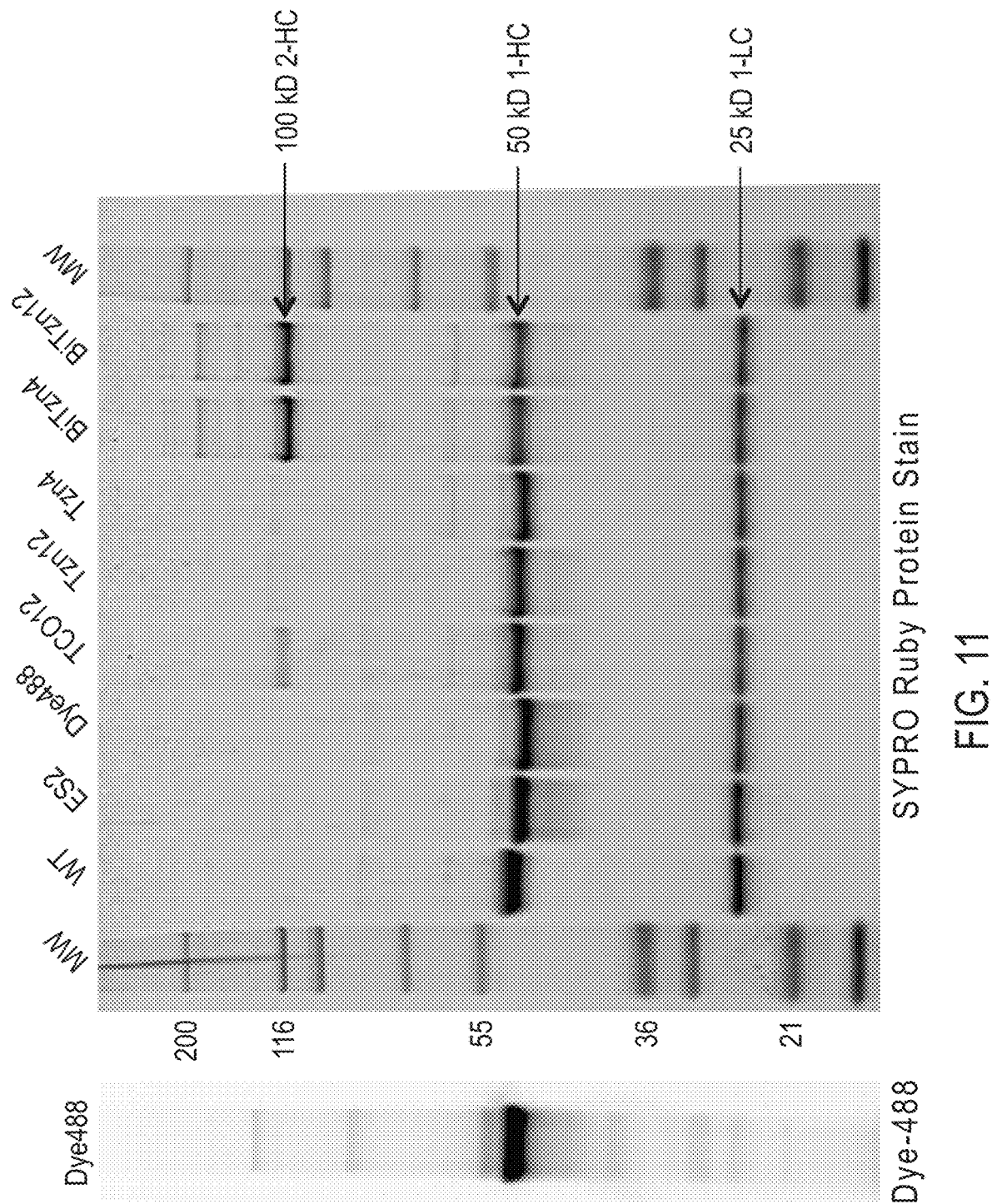
FIG. 11: A reducing gel demonstrating functionalization and conjugation of NIST monoclonal antibody reference material 8671 for production of a model bispecific antibody. NIST mAb (NIST monoclonal antibody reference material 8671) was cleaved with EndoS2 (ES2), azide-modified, and activated with TCO or Tzn-PEG-DBCOs as described in Example 4. The degree of labeling (DOL) of azide-modified NIST mAb was determined to be 2.0 as determined by labeling with DIBO-Dye488. The Dye-488 fluorescence image is shown in the left panel and corresponds to lane 4 in the gel in the right panel. The gel was post-stained in SYPRO Ruby (right panel) and re-imaged for total protein staining. In the right panel, Lane 1: MW Markers, Lane 2: Wild Type NIST mAb (WT), Lane 3: EndoS2-cleaved NIST mAb (ES2), Lane 4: Dye-488 labeled NIST mAb (Dye488), Lanes 5, 6, and 7: TCO-PEG12 (TCO12), Tzn-PEG12 (Tzn12) or Tzn-PEG4 (Tzn4)-functionalized NIST mAb, respectively, Lane 8: Tzn-PEG4/TCO-PEG12 crosslinked NIST mAb (BiTzn4), Lane 9: Tzn-PEG12/TCO-PEG12 crosslinked NIST mAb (BiTzn12). The expected 100 kD crosslinked heavy chains (2-HC), monomeric heavy chain (1-HC) and light chains (1-LC) are shown.

As shown in FIG. 11, NIST mAb (NIST monoclonal antibody reference material 8671) was cleaved with EndoS2 (ES2), azide-activated, and functionalized with TCO or Tzn-PEG-DBCOs as described in the "Materials and Methods" above. The degree of labeling (DOL) of azide-activated NIST mAb was determined to be 2.0 as determined by labeling with DIBO-Dye488. The Dye-488 fluorescence image is shown in the left panel of FIG. 11 and corresponds to lane 4 in the right panel of FIG. 11. The gel was post-stained in SYPRO Ruby (right panel) and re-imaged for total protein staining. In the right panel, Lane 1: MW Markers, Lane 2: Wild Type NIST mAb (WT), Lane 3: EndoS2-cleaved NIST mAb, Lane 4: Dye-488 labeled NIST mAb: Lanes 5, 6, and 7: TCO or Tzn-functionalized NIST mAb, Lane 8: Tzn-PEG4/TCO-PEG12 crosslinked NIST mAb, Lane 9: Tzn-PEG12/TCO-PEG12 crosslinked NIST mAb. The expected 100 kD crosslinked heavy chains (HC), monomeric HC and light chains (LC) are shown.

Figure 12:
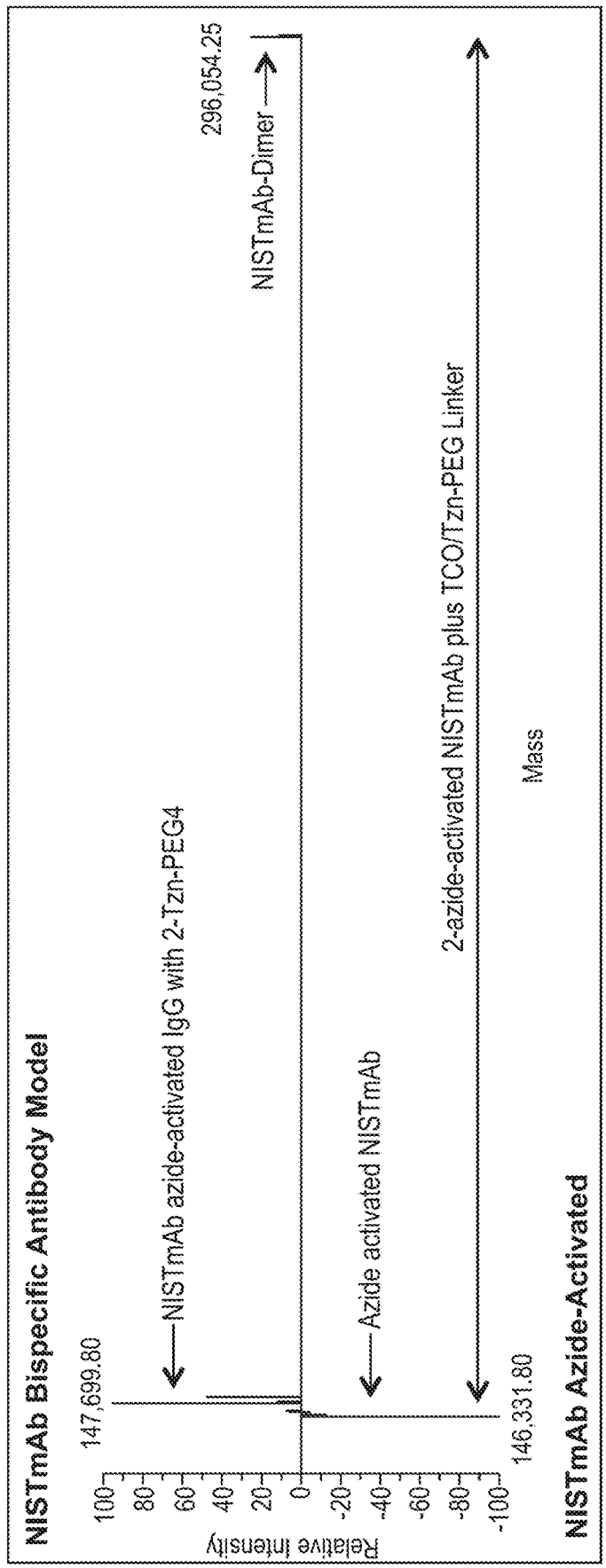
FIG. 12: Mass spectroscopy analysis of the model NIST monoclonal antibody (mAb) bispecific antibody confirms the tetravalent crosslinked form with only a single crosslink between the NIST mAb TCO-Tzn PEG pairs.

FIG. 12 shows mass spectrometry analysis of the site-specifically crosslinked NIST mAb described in FIG. 11 and demonstrated that only a single crosslink was formed between the NIST mAb TCO-Tzn PEG pairs. Although the treatment with endoglycosidase should result in two available sites for conjugating the modified sugar and subsequent crosslinking, it was unexpectedly discovered that only a single site is utilized in the crosslinking reaction and there is no "daisy-chaining" of activated antibodies. This unexpected discovery results in only two (2) antibodies being crosslinked which results in a very high yield of the desired bispecific antibody. Gel analyses demonstrated a high yield of the desired tetravalent bispecific species (greater than 80% yield without purification) that can then be further screened for binding and physiological efficacy.

Figure 13A:
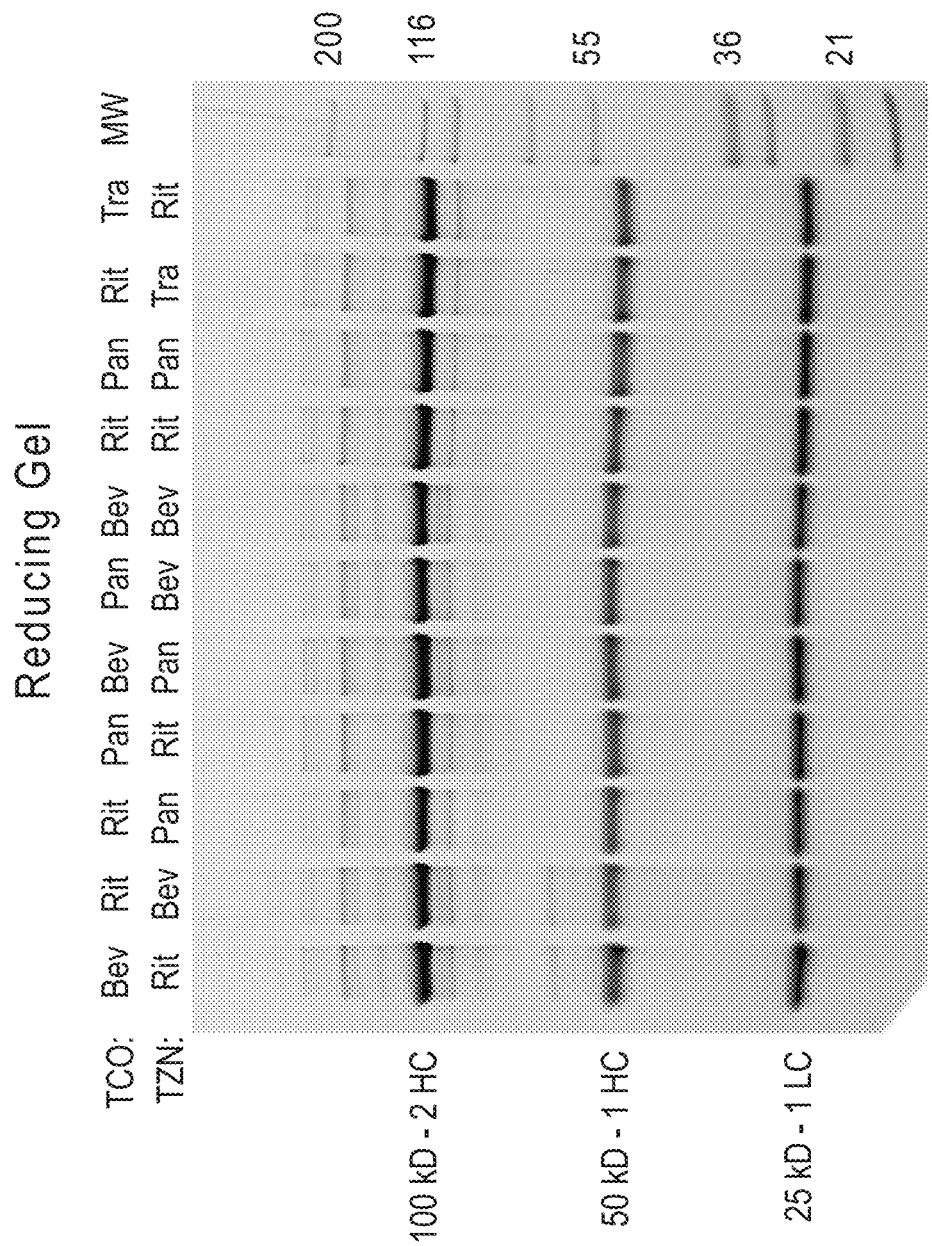
FIG. 13A and FIG. 13B: Reducing and non-reducing gels show rapid production of site-specifically crosslinked therapeutic antibody tetravalent pairs for bispecific antibody screening. Four model therapeutic antibodies, rituximab (Rit), bevacizumab (Bev), panitumumab (Pan), and trastuzumab (Tra), were mixed-and-matched to produce bispecific antibodies using the workflow described in Example 4. Specifically, the azide-activated antibodies were reacted with DBCO-TCO or DBCO-Tzn. After purification, the TCO or Tzn labeled antibodies were combined in equimolar amounts and allowed to react overnight. The antibodies were then analyzed by gel electrophoresis with or without DTT reduction.
Figure 13B:
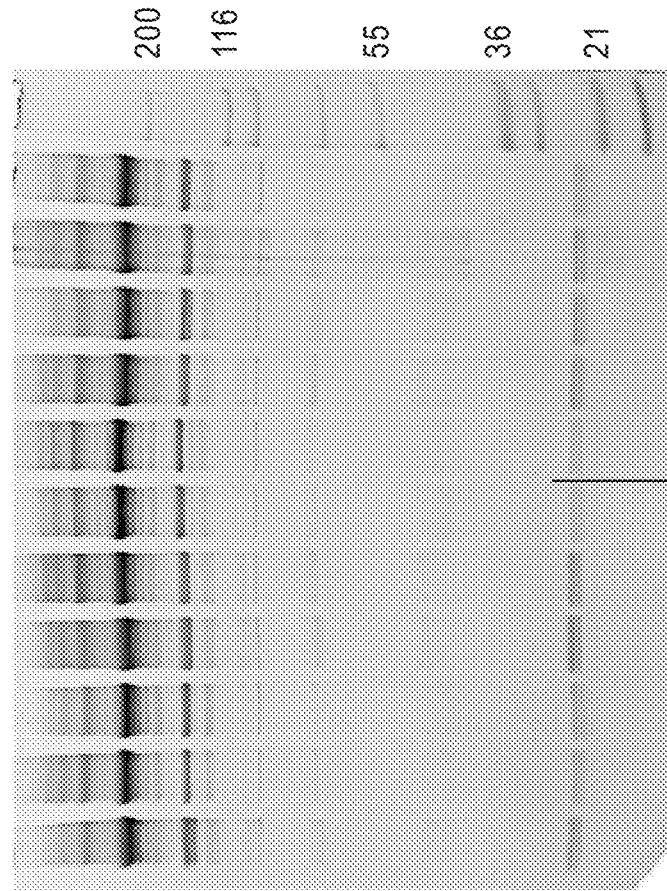
Figure 13B:
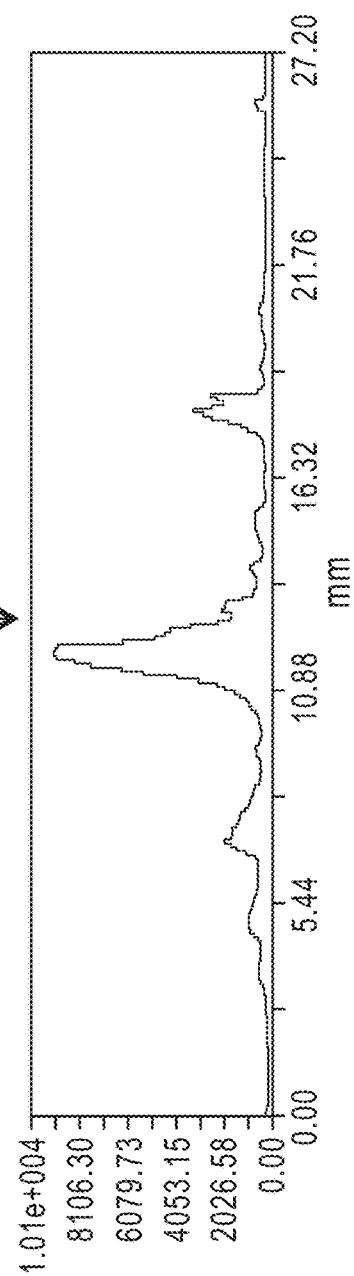

Four model therapeutic antibodies, rituximab (Rit), bevacizumab (Bev), panitumumab (Pan), and trastuzumab (Tra), were mixed-and-matched to produce bispecific antibodies using the workflow described in the "Materials and Methods" above. Specifically, the azide-activated antibodies were reacted with DBCO-TCO or DBCO-Tzn. After purification, the TCO or Tzn labeled antibodies were combined in equimolar amounts and allowed to react overnight. The antibodies were then analyzed by gel electrophoresis with or without DTT reduction. FIG. 13A shows a reducing gel with the predominant formation of 100 kD crosslinked heavy chain species. FIG. 13B shows a non-reducing gel with the predominant formation of the 300 kD tetravalent bispecific antibody species. This site-specific, directional, conjugation method ensures the efficient yield of tetravalent bispecific species leaving the antibody binding domains intact, and preventing the formation of highly-crosslinked undesirable antibody complexes.

Figure 15A:
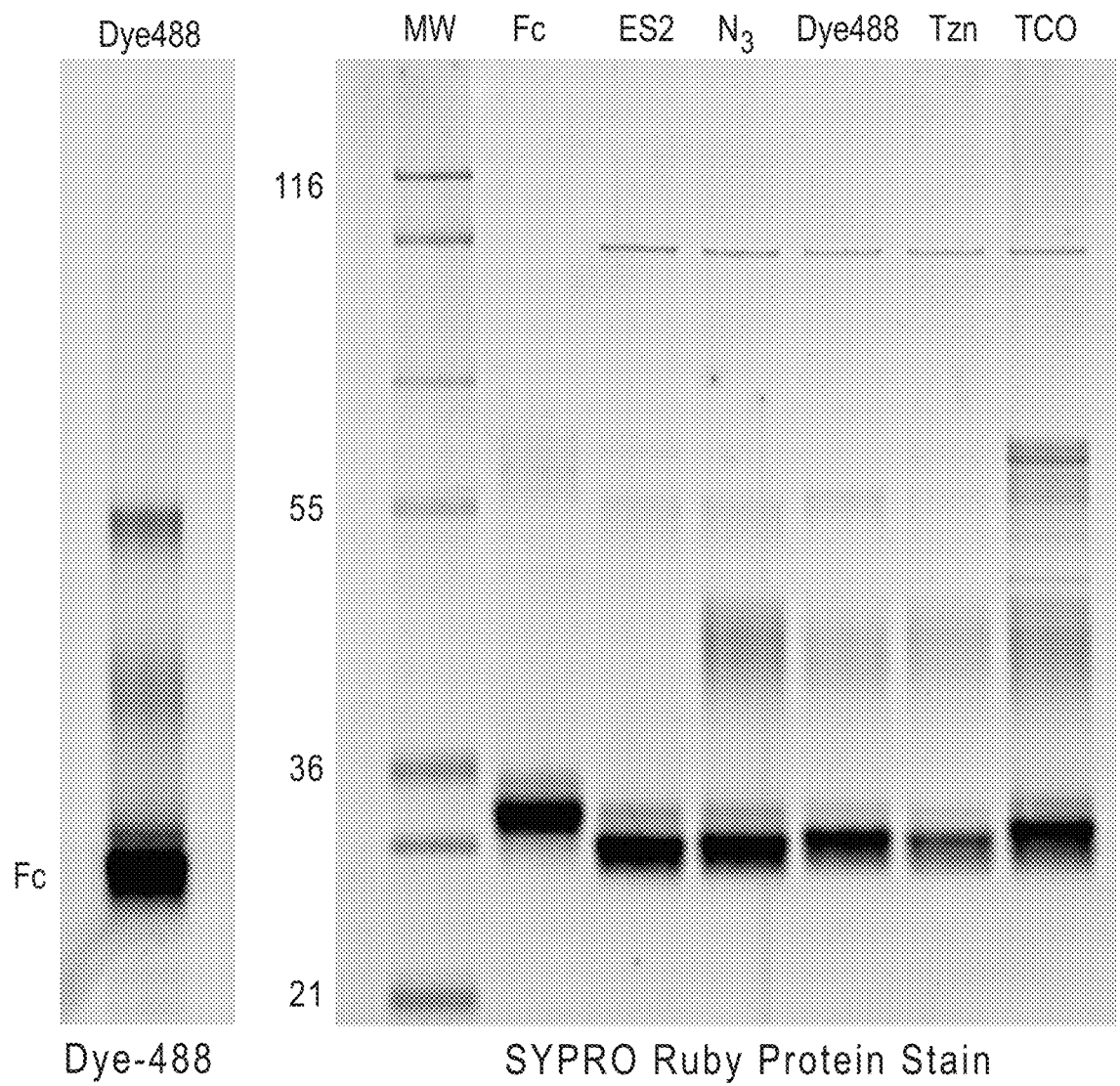
FIGS. 15A, 15B and 15C: Non-reducing gels showing production of Trastuzumab and Rituximab hIgG-Fc protein conjugates.
Figure 15B:
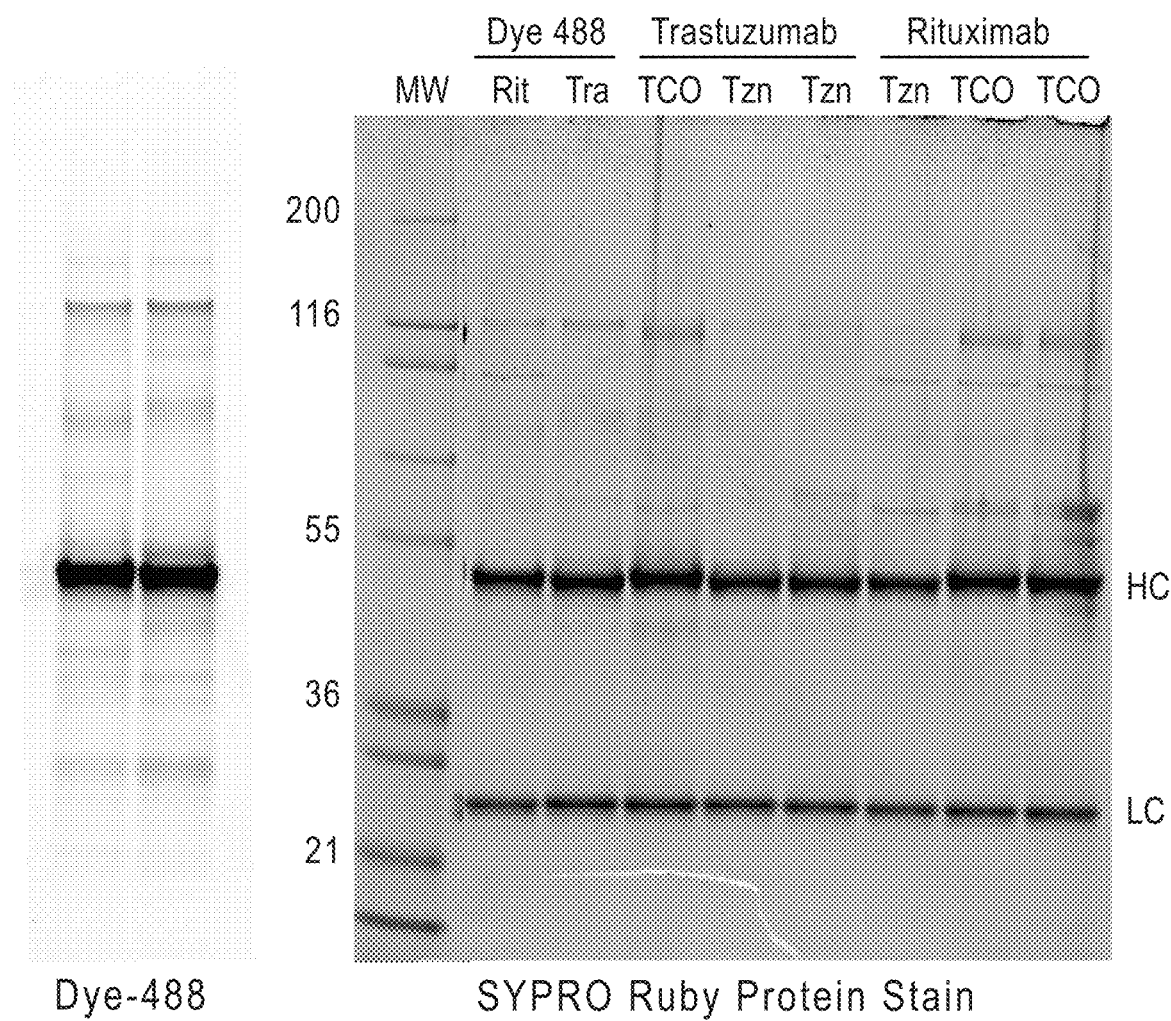
Figure 15C:
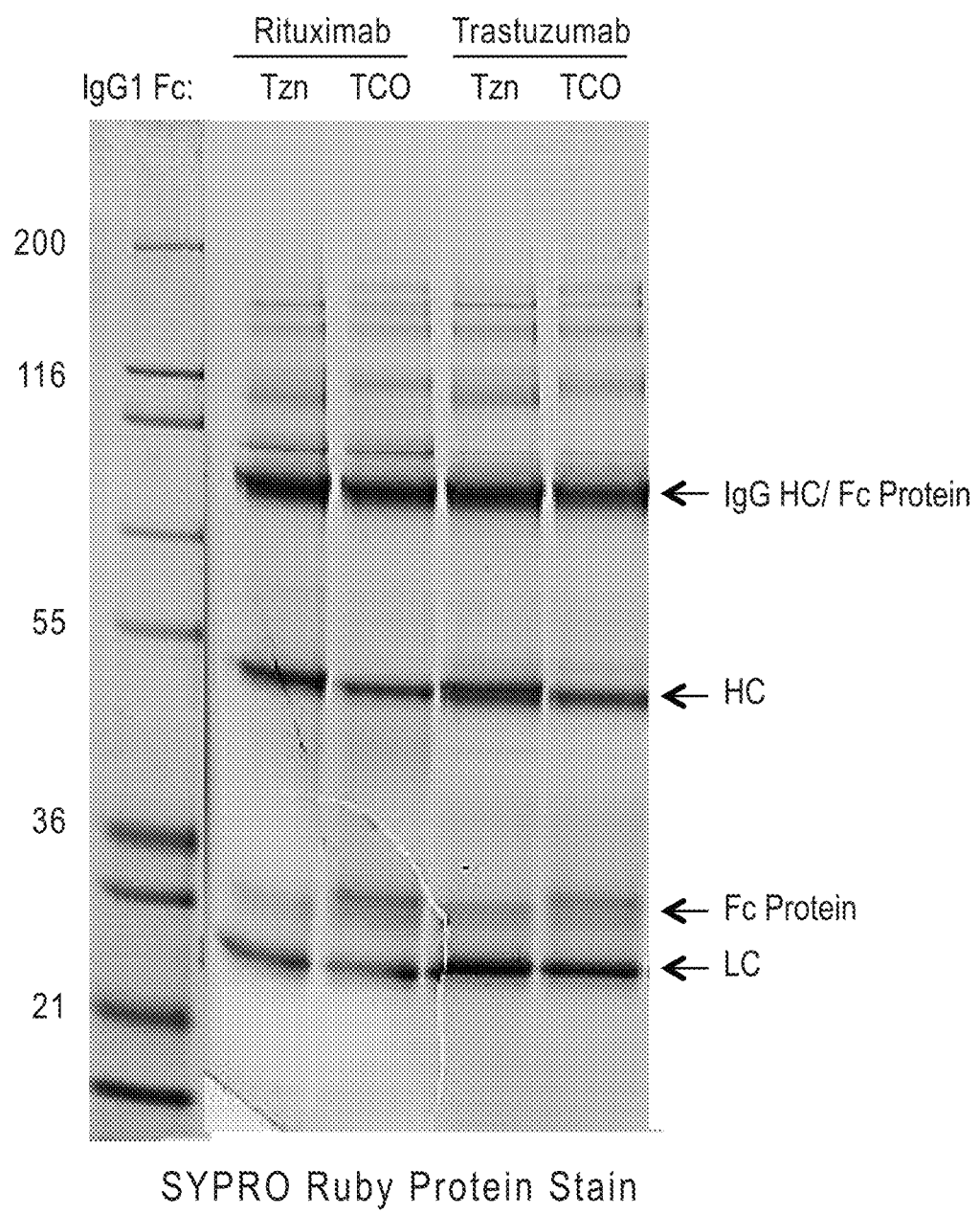

In FIG. 15A and FIG. 15B, the fluorescence scans of the DIBO-Dye-488-labeled proteins are shown in the far left panels and correspond to the Dye-488 Lanes 2 and 3 in the SYPRO Ruby gel. These were used to determine the DOL of the azide-activated proteins. FIG. 15A: Right gel panel, Lane 2 shows the wild type (WT) Fc protein, Lane 3, the EndoS2-cleaved protein (ES-2), Lane 4, the azide-activated protein (N₃), Lane 5, the DIBO-Dye-488 labeled protein, and Lanes 6 and 7 show the TCO and Tzn-activated forms. FIG. 15B: Azide-activated forms of trastuzumab (tra) and rituximab (rit) functionalized with TCO or Tzn are shown in Lanes 4-9. FIG. 15C: Conjugates of human IgG1-Fc protein with trastuzumab and rituximab are shown in Lanes 2-5. The TCO-Tzn pairs were mixed and matched producing the expected 75 kD protein conjugates shown.

Figure 16A:
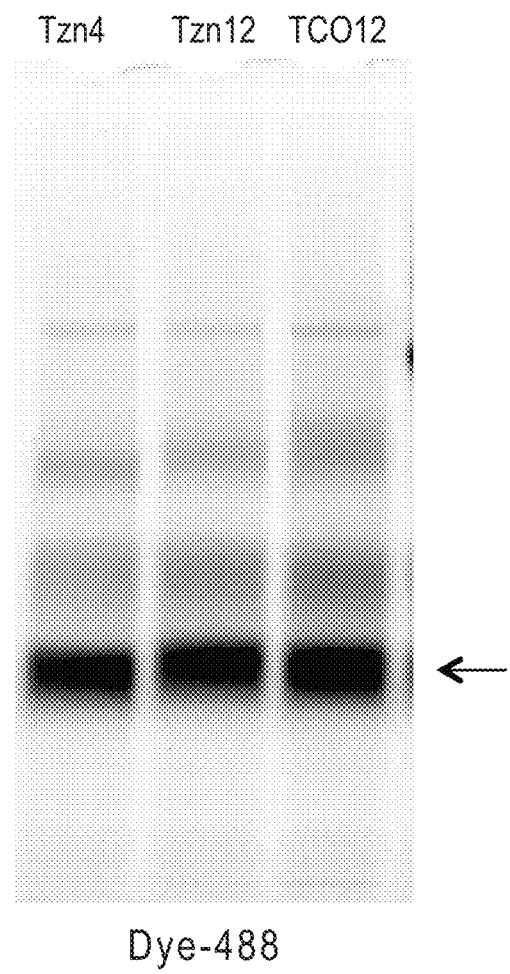
FIGS. 16A, 16B and 16C: Reducing gels showing production of fluorescent-labeled human IgG1 (hIgG1)-Fc protein "payload" for site-specific conjugation to antibodies.
Figure 16B:
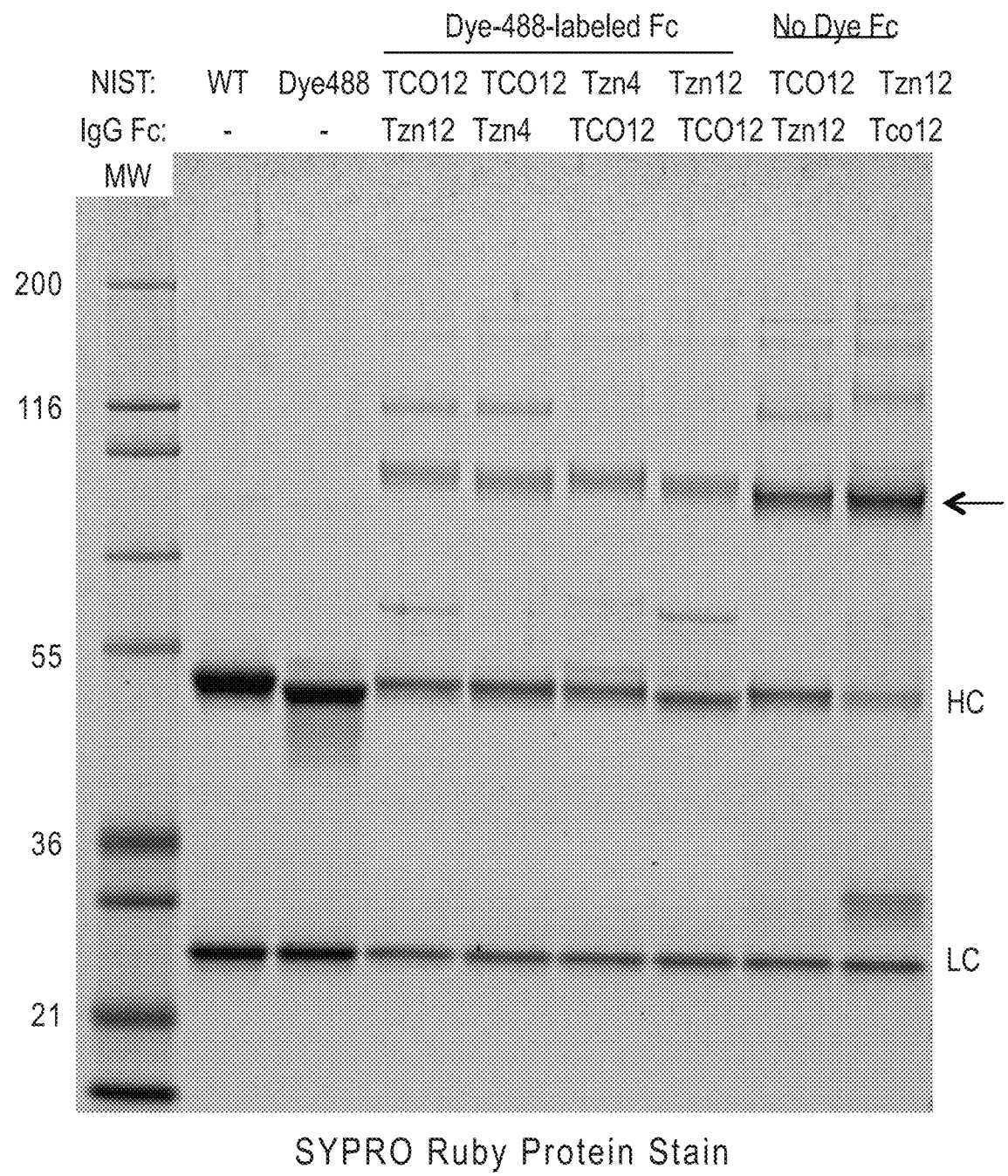
Figure 16C:
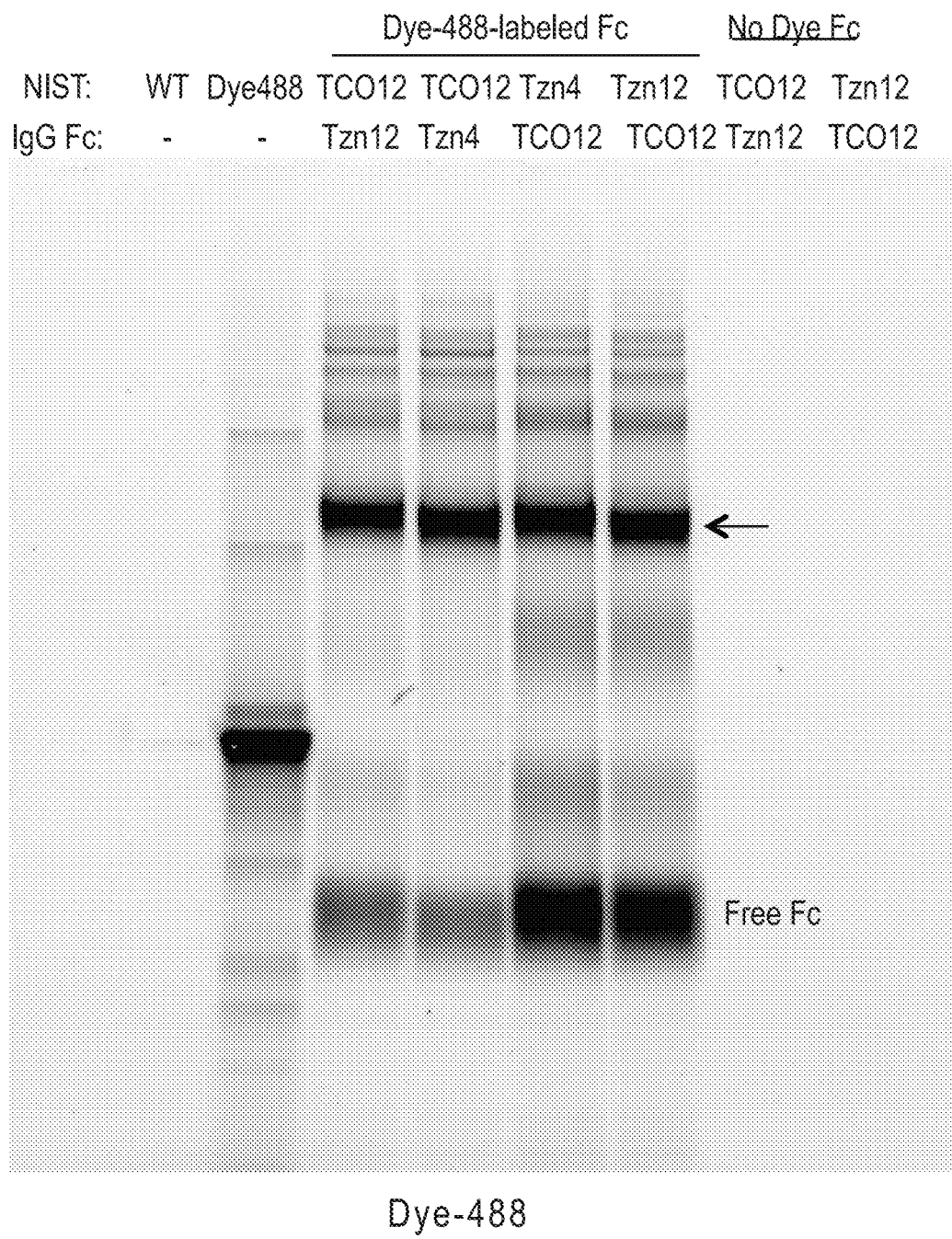

As shown in FIGS. 16A, 16B and 16C, azide-activated hIgG-Fc protein was activated with TCO-PEG-12-DBCO (TCO12), or Tzn-PEG12-DBCO (Tzn12) Tzn-PEG4-DBCO (Tzn4) and post-labeled with Dye-488-SE in a one-pot reaction. The proteins were separated by gel electrophoresis and images acquired as described in the "Materials and Methods" above. The DOL of the final Dye-488 labeled Fc proteins was 5-7 dyes per Fc protein (average). The fluorescence image of the three labeled compounds is shown in FIG. 16A. The arrow indicates the Dye-488- labeled Fc Proteins. The Dye-488 labeled TCO/Tzn-Fc proteins were mixed and matched with the corresponding NIST mAb TCO-Tzn pairs, and the resulting conjugates were resolved by reducing gel electrophoresis. The gel was imaged for Dye488 fluorescence (FIG. 16C) and then post-stained with SYPRO Ruby total protein stain (FIG. 16B). The expected 75 kD fluorescently-tagged NIST mAb conjugates are shown (arrows). The fluorescent NIST mAb-Fc conjugates show marked quenching of the SYPRO Ruby staining in comparison to the non-labeled species (no-Dye Fc), a result of strong Dye-488 labeling. There was little difference between the PEG12 or PEG4 species in conjugation efficiency, and there did not seem to be a preference for TCO or Tzn for either of the proteins.

Discussion:

Described herein are site-specific, directional crosslinking methods for the production of bispecific antibodies and antibody conjugates using essentially any pre-existing antibody or antibody fragment. These methods: a) can be used to simultaneously and rapidly screen multiple antibody pairs without genetic engineering; b) result in predominantly a single crosslinked species with a high yield of the desired tetravalent bispecific products; c) can be used to site-specifically attach "armed" Fc-protein scaffolds to an antibody without disrupting the antigen binding domain; d) can be used to impart a desired Fc-specific functionality to an antibody; and e) allows for the attachment of any Fc protein subtype from any animal species to an antibody.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of making a bispecific antibody or antibody conjugate, the method comprising:
   a) providing a first antibody comprising an oligosaccharide having a GlcNAc-GlcNAc linkage;
   b) contacting the first antibody comprising an oligosaccharide having a GlcNAc-GlcNAc linkage with an endoglycosidase S2 enzyme to provide a first antibody comprising a terminal GlcNAc residue;
   c) providing a first UDP-GalNAz;
   d) contacting the first antibody comprising a terminal GlcNAc residue with the first UDP-GalNAz and a GalT(Y289L) mutant galactosyl transferase enzyme, wherein the GalT(Y289L) mutant galactosyl transferase enzyme catalyzes attachment of the first UDP-GalNAz to the terminal GlcNAc residue of the first antibody thereby forming a first modified antibody;
   e) providing a first activating molecule comprising: i) a first crosslinking group comprising a trans-cyclooctene (TCO), ii) a first reactive group selected from a dibenzocyclooctyne, a difluorocyclooctyne, an aza-dibenzocyclooctyne, or a cyclononyne, and iii) a linker comprising one or more polyethylene glycol (PEG) groups;
   f) contacting the first modified antibody with the first activating molecule, wherein the first activating molecule attaches to the first modified antibody at the azido group from the first UDP-GalNAz, thereby forming a first activated antibody;
   g) providing a second antibody comprising an oligosaccharide having a GlcNAc-GlcNAc linkage;
   h) contacting the second antibody comprising an oligosaccharide having a GlcNAc-GlcNAc linkage with an endoglycosidase S2 enzyme to provide a second antibody comprising a terminal GlcNAc residue;
   i) providing a second UDP-GalNAz;
   j) contacting the second antibody comprising a terminal GlcNAc residue with the second UDP-GalNAz and the GalT(Y289L) mutant galactosyl transferase enzyme, wherein the GalT(Y289L) mutant galactosyl transferase enzyme catalyzes attachment of the second UDP-GalNAz to the terminal GlcNAc residue of the second antibody thereby forming a second modified antibody;
   k) providing a second activating molecule comprising: i) a second crosslinking group comprising a tetrazine, ii) a second reactive group selected from a dibenzocyclooctyne, a difluorocyclooctyne, an aza-dibenzocyclooctyne, or a cyclononyne, and iii) a linker comprising one or more polyethylene glycol (PEG) groups;
   l) Contacting the second modified antibody with the second activating molecule, wherein the second activating molecule attaches to the second modified antibody at the azido group from the second UDP-GalNAz, thereby forming a second activated antibody; and
   m) contacting the first activated antibody with the second activated antibody, wherein the first crosslinking group of the first activated antibody reacts with the second crosslinking group of the second activated antibody forming a single cross-link between the first and second activated antibodies, thereby forming the bispecific antibody or antibody conjugate.

2. The method of claim 1, wherein the first antibody and the second antibody are the same.

3. The method of claim 1, wherein the first antibody and the second antibody are different.

4. The method of claim 1, wherein
   (i) steps (a) through (f) are performed before steps (g) through (m);
   (ii) steps (a) through (f) are performed after steps (g) through (m); or
   (iii) steps (a) through (f) are performed concurrently with steps (g) through (m).

5. The method of claim 1, wherein the linker comprises: one or more polyethylene glycol (PEG) groups.

6. The method of claim 1, wherein the method produces at least about 80% yield of bispecific antibodies or antibody conjugates with a single cross-link between the first and second activated antibodies.

7. The method of claim 5, wherein the one or more PEG groups comprises 1 to 5 PEG groups.

8. The method of claim 5, wherein the one or more PEG groups comprises 1 to 15 PEG groups.

9. The method of claim 5, wherein the one or more PEG groups comprises 1 to 25 PEG groups.

10. The method of claim 5, wherein the one or more PEG groups comprises 1 to 50 PEG groups.

* * * * *

UNITED STATES PATENT AND TRADEMARK OFFICE
CERTIFICATE OF CORRECTION

| | | |
|---|---|---|
| PATENT NO. | : 12,071,487 B2 | Page 1 of 1 |
| APPLICATION NO. | : 16/306610 | |
| DATED | : August 27, 2024 | |
| INVENTOR(S) | : Brian Agnew et al. | |

It is certified that error appears in the above-identified patent and that said Letters Patent is hereby corrected as shown below:

In the Claims

In Column 92, Claim 1, Line 26, delete "Contacting" and insert -- contacting --, therefor.

In Column 92, Claim 5, Line 49, delete "comprises:" and insert -- comprises --, therefor.

Signed and Sealed this
First Day of October, 2024

Katherine Kelly Vidal
*Director of the United States Patent and Trademark Office*